(12) United States Patent
Jung

(10) Patent No.: US 9,847,492 B2
(45) Date of Patent: Dec. 19, 2017

(54) ORGANIC COMPOUND AND ORGANIC LIGHT EMITTING DIODE DEVICE INCLUDING THE SAME

(71) Applicant: SAMSUNG DISPLAY CO., LTD., Yongin, Gyeonggi-Do (KR)

(72) Inventor: Ji Yun Jung, Seoul (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 271 days.

(21) Appl. No.: 14/595,345

(22) Filed: Jan. 13, 2015

(65) Prior Publication Data
US 2016/0013420 A1    Jan. 14, 2016

(30) Foreign Application Priority Data
Jul. 10, 2014 (KR) .................. 10-2014-0086973

(51) Int. Cl.
| | | |
|---|---|---|
| H01L 51/50 | (2006.01) | |
| H01L 51/00 | (2006.01) | |
| C07D 251/24 | (2006.01) | |
| C07D 401/04 | (2006.01) | |
| C07D 239/26 | (2006.01) | |
| C07D 401/14 | (2006.01) | |
| C07D 213/16 | (2006.01) | |
| C07D 471/04 | (2006.01) | |

(52) U.S. Cl.
CPC ........ *H01L 51/0067* (2013.01); *C07D 213/16* (2013.01); *C07D 239/26* (2013.01); *C07D 251/24* (2013.01); *C07D 401/04* (2013.01); *C07D 401/14* (2013.01); *C07D 471/04* (2013.01); *H01L 51/0052* (2013.01); *H01L 51/0055* (2013.01); *H01L 51/0058* (2013.01); *H01L 51/0072* (2013.01); *H01L 51/5072* (2013.01)

(58) Field of Classification Search
None
See application file for complete search history.

(56) References Cited

U.S. PATENT DOCUMENTS

| | | | | |
|---|---|---|---|---|
| 2008/0220285 | A1* | 9/2008 | Vestweber | ............. C07C 13/62 |
| | | | | 428/690 |
| 2013/0053558 | A1* | 2/2013 | Pflumm | ............... C07D 403/10 |
| | | | | 544/180 |

FOREIGN PATENT DOCUMENTS

| | | |
|---|---|---|
| JP | 10-017860 | 1/1998 |
| JP | 11-087067 | 3/1999 |

(Continued)

*Primary Examiner* — Gregory Clark
(74) *Attorney, Agent, or Firm* — Lee & Morse, P.C.

(57) ABSTRACT

An organic compound is represented by Formula 1.

[Formula 1]

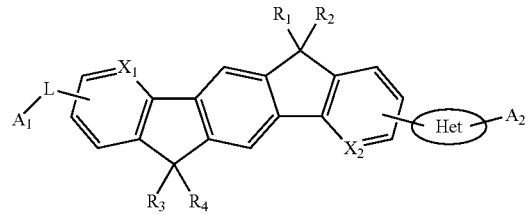

where $X_1$, $X_2$, L, $A_1$, $A_2$, R1, $R_2$, $R_3$, $R_4$, and Het are as defined in the specification.

2 Claims, 1 Drawing Sheet

(56) References Cited

FOREIGN PATENT DOCUMENTS

| | | |
|---|---|---|
| JP | 11-345686 | 12/1999 |
| KR | 10-2011-0122129 | 11/2011 |
| KR | 10-2012-0103551 | 1/2012 |

\* cited by examiner

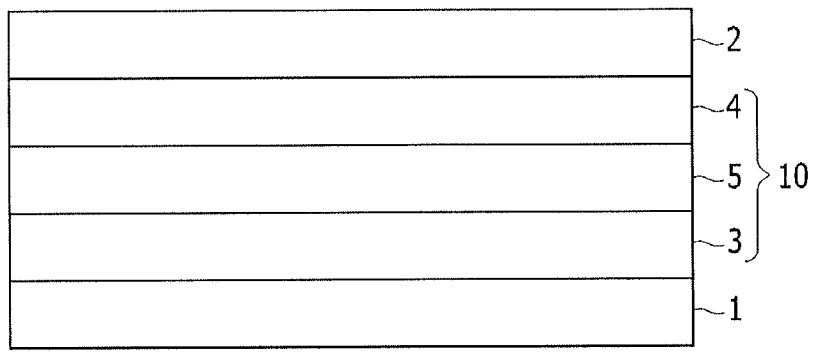

ORGANIC COMPOUND AND ORGANIC LIGHT EMITTING DIODE DEVICE INCLUDING THE SAME

CROSS-REFERENCE TO RELATED APPLICATION

Korean Patent Application No. 10-2014-0086973 filed on Jul. 10, 2014, in the Korean Intellectual Property Office, and entitled: "Organic Compound and Organic Light Emitting Diode Device Including the Same," is incorporated by reference herein in its entirety.

BACKGROUND

1. Field

Embodiments relate to an organic compound and an organic light emitting diode device including the same.

2. Description of the Related Art

Recent trends toward lightweight and thin personal computers and televisions sets also require lightweight and thin display devices, and flat panel displays satisfying such requirements are being substituted for conventional cathode ray tubes (CRTs.)

However, since the LCD is a passive display device, an additional back-light as a light source is needed, and the LCD has various problems such as a slow response time and a narrow viewing angle. In this connection, an organic light emitting diode (OLED) display has recently been spotlighted as a display device that has merits such as a wide viewing angle, outstanding contrast, and a fast response time. In the organic light emitting diode device, electrons injected from one electrode and holes injected from another electrode are combined with each other in an emission layer, thereby generating excitons, and energy is outputted from the excitons to thereby emit light.

SUMMARY

Embodiments are directed to an organic compound represented by Formula 1:

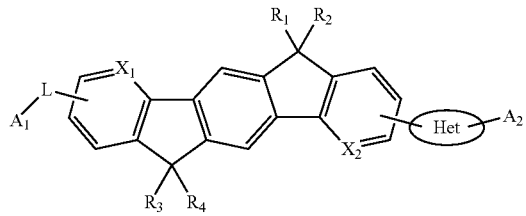

[Formula 1]

Wherein, Formula 1, $X_1$ and $X_2$ are $CR_5$ or N, $R_1$ to $R_5$ are independently hydrogen, deuterium, a halogen, a C1 to C40 alkyl group, a C5 to C40 aryl group, a C5 to C40 heteroaryl group, a C5 to C40 aryloxy group, a C1 to C40 alkyloxy group, a C5 to C40 arylamino group, a C5 to C40 diarylamino group, a C6 to C40 arylalkyl group, a C3 to C40 cycloalkyl group, or a C3 to C40 heterocycloalkyl group, and any of $R_1$ to $R_5$ may form a fused aliphatic ring, a fused aromatic ring, a fused heteroaliphatic ring, or a fused heteroaromatic ring with an adjacent group or a combination thereof, L is a single-bond, a substituted or unsubstituted C5 to C30 arylene group, a substituted or unsubstituted C10 to C30 fused arylene group, a substituted or unsubstituted C2 to C30 heteroarylene group including at least one of N, S, and O, or a substituted or unsubstituted C5 to C30 fused heteroarylene group including at least one of N, S, and O, Het is a substituted or unsubstituted C3 to C20 heteroarylene group including N, and $A_1$ and $A_2$ are hydrogen, a substituted or unsubstituted C5 to C40 aryl group and, or a substituted or unsubstituted C5 to C40 heteroaryl group.

The compound represented by Formula 1 may include at least one of Compounds 1 to 72 (reproduced below).

Embodiments are also directed to an organic light emitting diode device including an anode, a cathode, and an organic layer provided between the anode and the cathode, wherein the organic layer includes an organic compound represented by Formula 1.

The organic layer may include an emission layer. The organic compound represented by Formula 1 may be included in the emission layer.

BRIEF DESCRIPTION OF THE DRAWING

Features will become apparent to those of skill in the art by describing in detail exemplary embodiments with reference to the attached drawing in which:

FIG. 1 illustrates a cross-sectional view of a configuration of an organic light emitting diode device according to an exemplary embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURES, the dimensions of layers and regions may be exaggerated for clarity of illustration. It will also be understood that when a layer or element is referred to as being "on" another layer or substrate, it can be directly on the other layer or substrate, or intervening layers may also be present. In addition, it will also be understood that when a layer is referred to as being "between" two layers, it can be the only layer between the two layers, or one or more intervening layers may also be present. Like reference numerals refer to like elements throughout.

In the present specification, the term "substituted," unless separately defined otherwise, indicates a substitution of at least one hydrogen atom with a substituent selected from deuterium, a C1 to C30 alkyl group, a C6 to C36 aryl group, a C2 to C30 heteroaryl group, a C1 to C30 alkoxy group, a C2 to C30 alkenyl group, a C6 to C30 aryloxy group, a C3 to C40 silyloxy group, a C1 to C30 acyl group, a C2 to C30 acyloxy group, a C2 to C30 heteroacyloxy group, a C1 to C30 sulfonyl group, a C1 to C30 alkylthiol group, a C6 to C30 arylthiol group, a C1 to C30 heterocyclothiol group, a C1 to C30 phosphoric acid amide group, a C3 to C40 silyl group, NRR' (where R and R' are respectively substituents selected from a hydrogen atom, a C1 to C30 alkyl group, and a C6 to C30 aryl group), a carboxylic acid group, a halogen group, a cyano group, a nitro group, an azo group, a fluorene group, and a hydroxyl group.

Further, the C6 to C36 aryl group, the C2 to C30 heteroaryl group, and the fluorene group from among the substituents may be further substituted with deuterium, a halogen, a cyano group, a methyl group, a tri-fluoromethyl group, or a phenyl group.

As used herein, the term "hetero," unless separately defined otherwise, indicates that a single ring contains one to three heteroatoms selected from the group consisting of N, O, S, and P, with carbon atoms as the remainder.

Also in the present specification, the term "organic layer" generally refers to layers including an organic material. Such an organic layer may further include an inorganic material and a metal complex in addition to the organic material. The organic layer may include at least one layer.

Further, among groups used in chemical formulae of the present specification, definition of a representative group is as follows (the number of carbons that limits substituents is not restrictive, and does not limit characteristics of the constituents).

An unsubstituted C1 to C30 alkyl group may be a linear type or a branched type. Examples of the unsubstituted C1 to C30 alkyl include methyl, ethyl, propyl, iso-propyl, sec-butyl, hexyl, iso-amyl, hexyl, heptyl, octyl, nonanyl, dodecyl, and the like.

An unsubstituted C2 to C30 alkenyl group has at least one carbon-carbon bond in the center or at a terminal of the unsubstituted alkyl group. Examples include ethenyl, propenyl, butenyl, or the like.

The term "unsubstituted C2 to C30 alkynyl group" refers to an alkyl group having at least one carbon-carbon triple bond in the center or at a terminal of the alkyl group. Examples of the unsubstituted C2-C30 alkynyl group include acetylene, propylene, phenylacetylene, naphthylacetylene, isopropylacetylene, t-butylacetylene, diphenylacetylene, or the like.

The term "unsubstituted C3 to C30 cycloalkyl group" refers to a C3 to C30 cyclic alkyl group.

The term "unsubstituted C1 to C30 alkoxy group" refers to a group having a structure of —OA (wherein A is an unsubstituted C1 to C30 alkyl group as described above). Examples of the unsubstituted C1 to C30 include a methoxy group, an ethoxy group, a propoxy group, an isopropyloxy group, a butoxy group, and a pentoxy group.

The term "unsubstituted C6 to C30 aryl group" refers to a carbocyclic aromatic system containing at least one ring. At least two rings may be fused to each other or linked to each other by a single bond. The term "aryl" refers to an aromatic system, such as phenyl, naphthyl, or anthracenyl. Examples of the unsubstituted C6 to C30 aryl group include a phenyl group, a tolyl group, a naphthyl group, an anthracenyl group, a terphenyl group, a phenanthrenyl group, a pyrenyl group, a diphenylanthracenyl group, a dinaphthylanthracenyl group, a pentacenyl group, a bromophenyl group, a hydroxyphenyl group, a stilbene group, an azobenzenyl group, or a ferrocenyl group.

An unsubstituted C2 to C30 heteroaryl group includes one, two, or three hetero atoms selected from B, N, O, S, and P. At least two rings may be fused to each other or linked each other by a single bond. Examples of the unsubstituted C2 to C30 heteroaryl group include a pyrazolyl group, an imidazolyl group, an oxazolyl group, a triazolyl group, a triazinyl group, a triazolyl group, a tetrazolyl group, an oxadiazole group, a thiadiazole group, a pyridinyl group, a pyridazinyl group, a pyrimidinyl group, a triazinyl group, a carbazole group, an indolyl group, a quinolyl group, an isoquinolyl group, a thiophene group, a dibenzothiophene group, a dibenzofuran group, and a benzimidazolyl group.

An unsubstituted C6 to C30 aryloxy group is a group represented by —OA$_1$, wherein A$_1$ is the same type of functional group as the C6 to C30 aryl group, having a different number of carbons. Examples of the aryloxy group may include a phenoxy group.

An unsubstituted C6 to C30 arylthio group is a group represented by —SA$_1$, where A$_1$ is the same type of functional group as the C6 to C30 aryl group, having a different number of carbons. Examples of the arylthio group include a benzenethio group, a naphthylthio group, or the like.

An organic compound according to an exemplary embodiment will now be described in detail.

The organic compound may be represented by Formula 1.

[Formula 1]

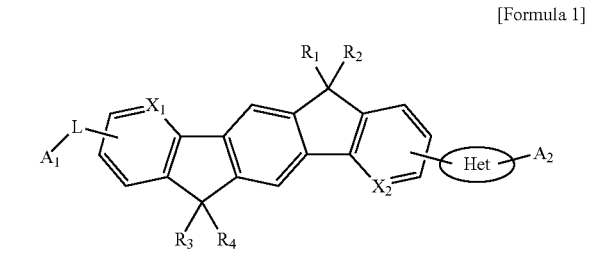

Here,

X$_1$ and X$_2$ are CR$_5$ or N,

R$_1$ to R$_5$ are independently H, D, a halogen, a C1 to C40 alkyl group, a C5 to C40 aryl group, a C5 to C40 heteroaryl group, a C5 to C40 aryloxy group, a C1 to C40 alkyloxy group, a C5 to C40 arylamino group, a C5 to C40 diarylamino group, a C6 to C40 arylalkyl group, a C3 to C40 cycloalkyl group, and a C3 to C40 heterocycloalkyl group, and any of R$_1$ to R$_5$ form a fused aliphatic ring, a fused aromatic ring, a fused heteroaliphatic ring, or a fused heteroaromatic ring with an adjacent group, or a combination thereof, L is a single-bond, a substituted or unsubstituted C5 to C30 arylene group, a substituted or unsubstituted C10 to C30 fused arylene group, a substituted or unsubstituted C2 to C30 heteroarylene group including at least one of N, S, and O, or a substituted or unsubstituted C5 to C30 fused heteroarylene group including at least one of N, S, and O, Het is a substituted or unsubstituted C3 to C20 heteroarylene group including N, and A$_1$ and A$_2$ are H, a substituted or unsubstituted C5 to C40 aryl group, or a substituted or unsubstituted C5 to C40 heteroaryl group.

As a detailed example of the compound represented by Formula 1, at least one of the Compounds 1 to 72 shown below may be provided.

The compounds 1 to 72 shown below may be used independently, at least two may be mixed and used, or they may be mixed with another compound and be used.

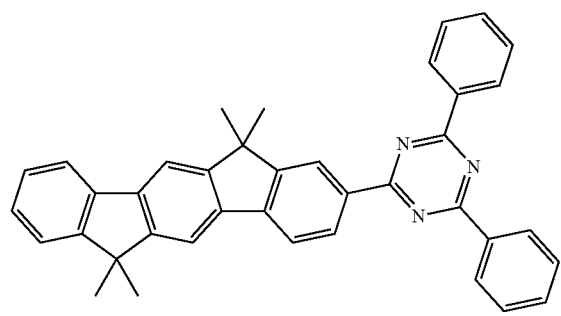
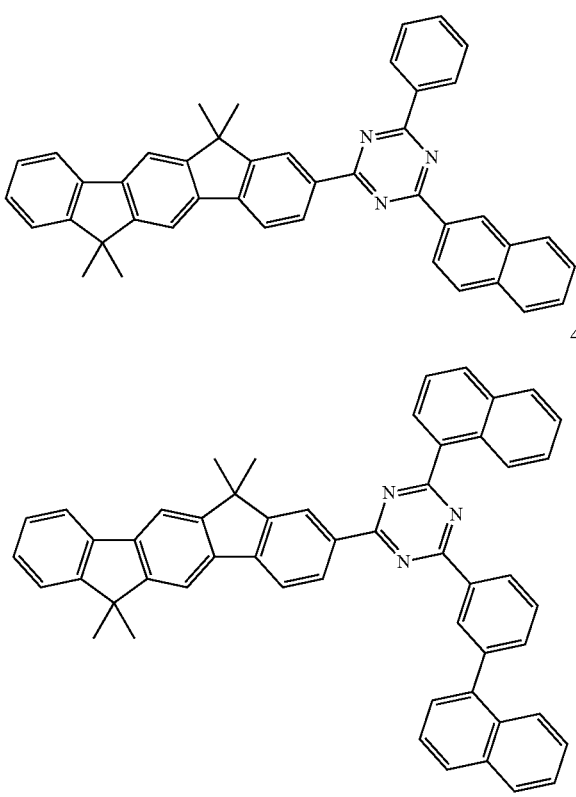
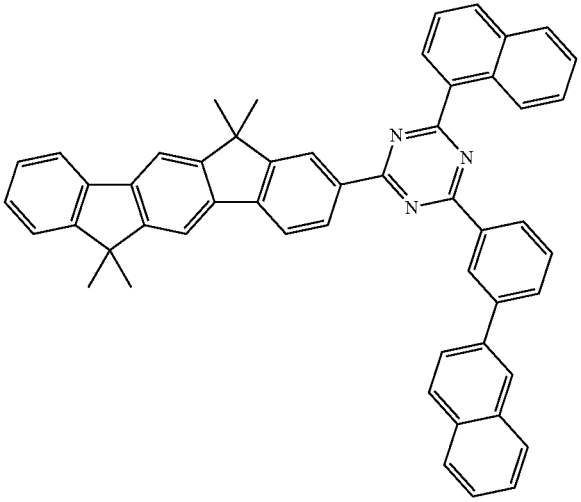

8
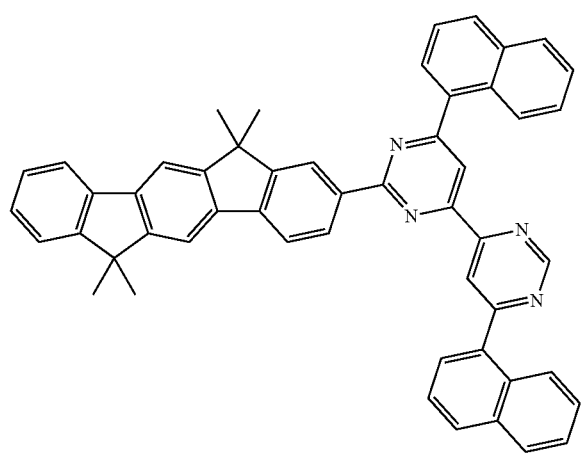
9
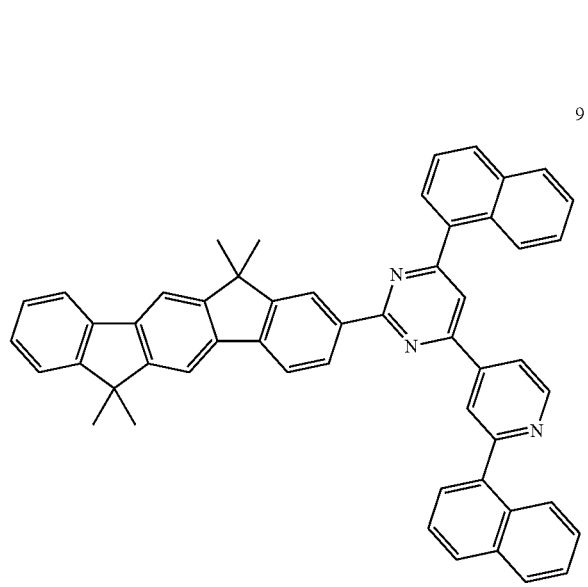
10
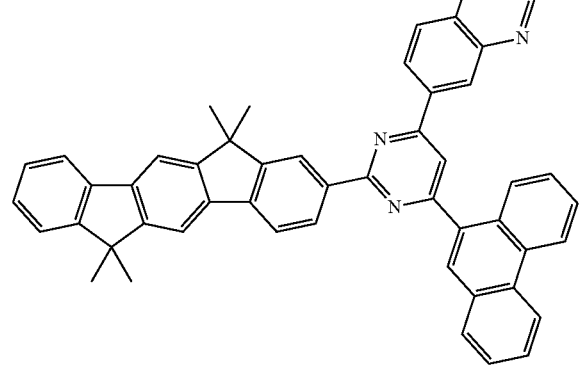
11
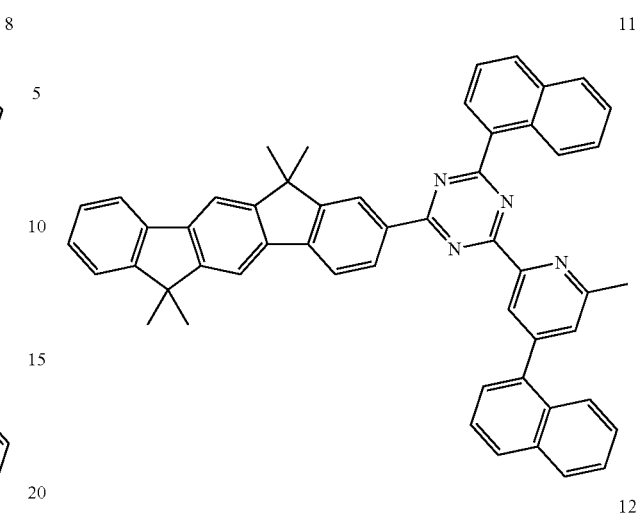
12
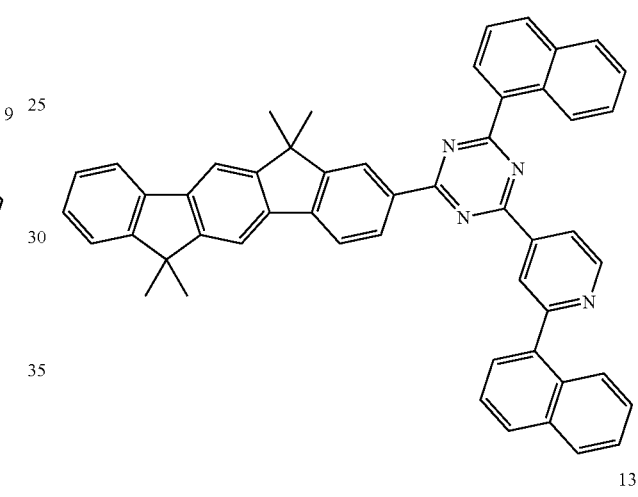
13
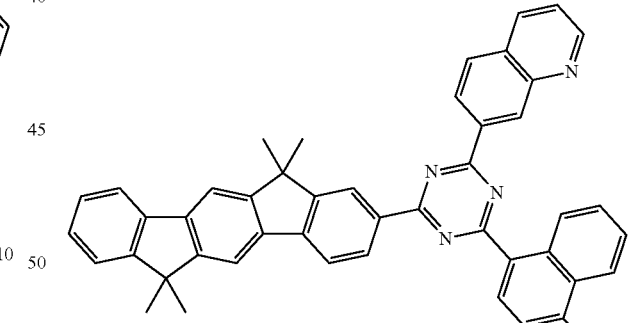

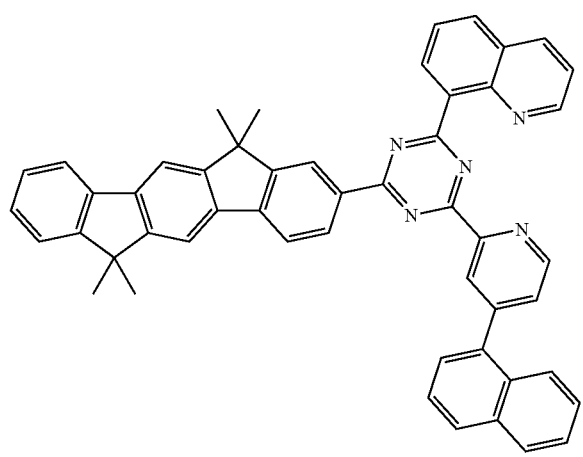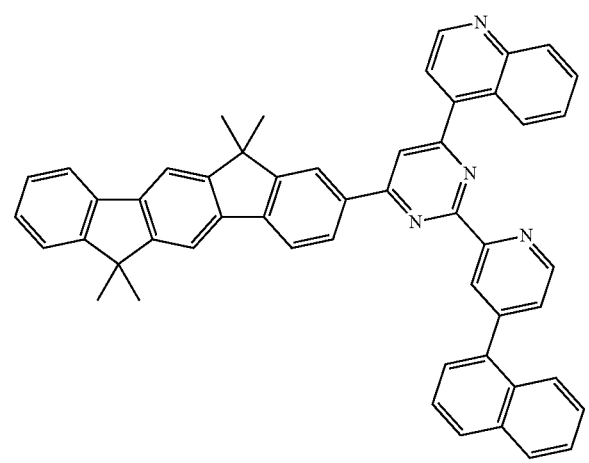

21
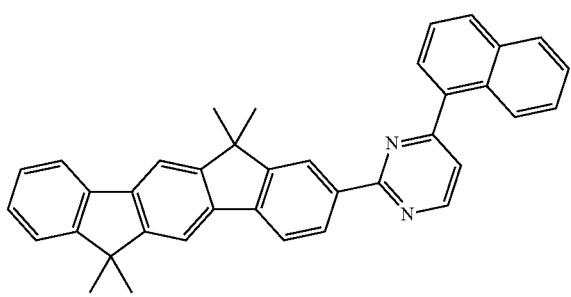
22
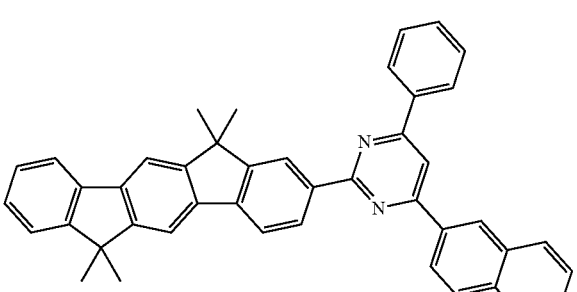
23
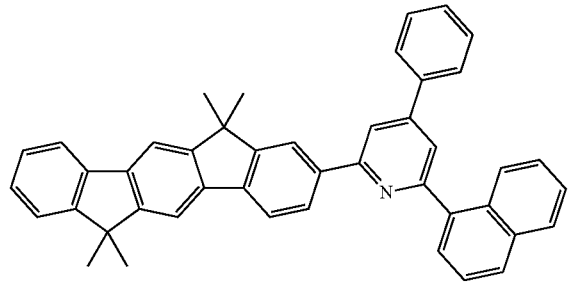
24
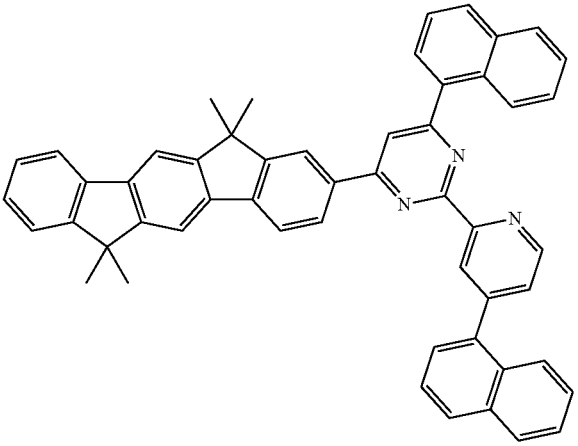
25
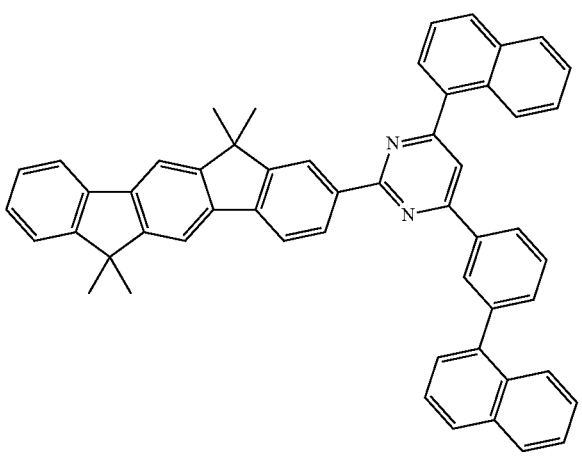
26
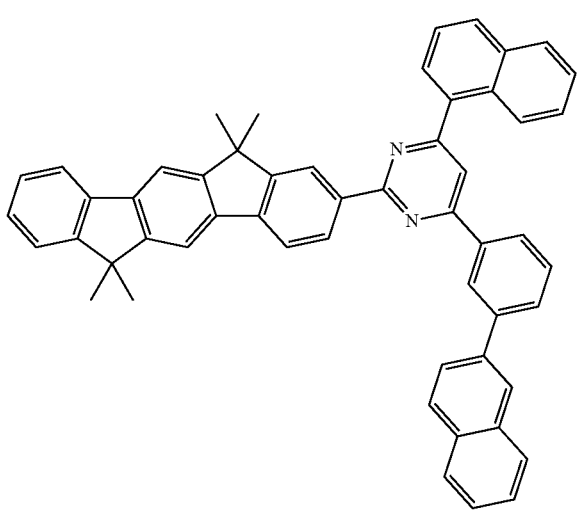
27
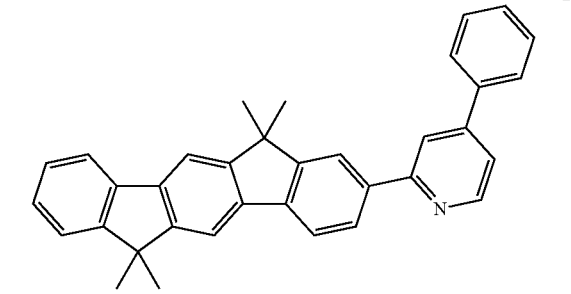
28
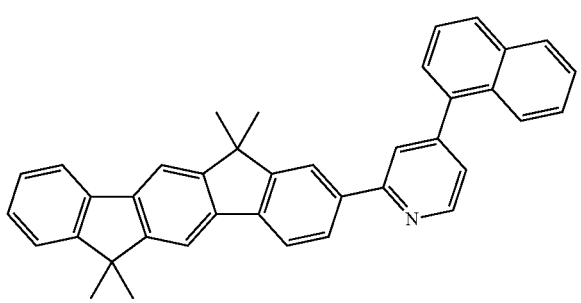

-continued

-continued
35
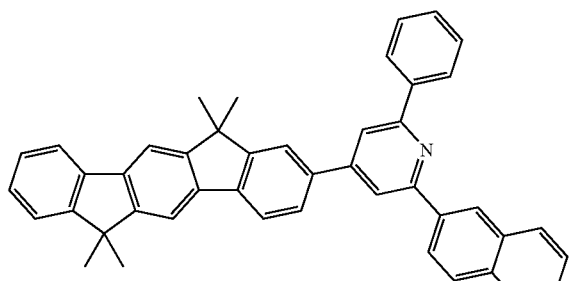
36
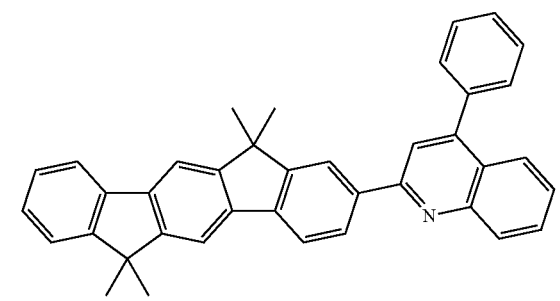
37
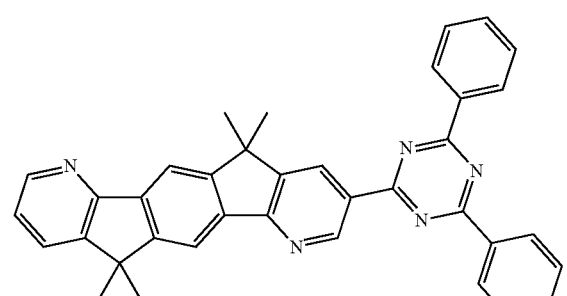
38
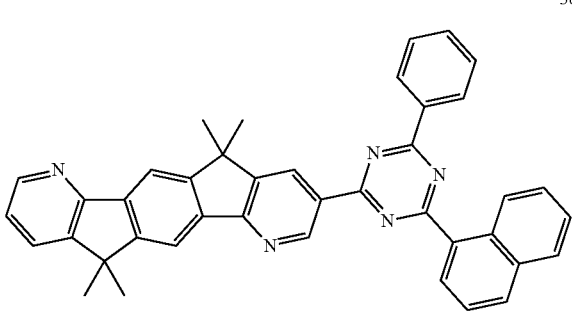
39
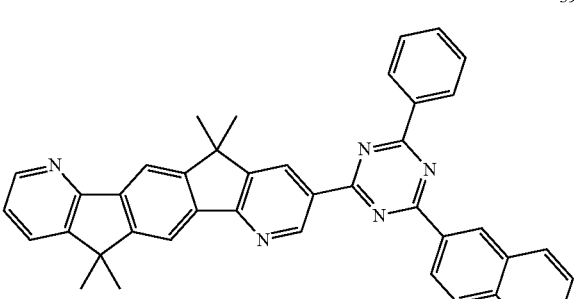
-continued
40
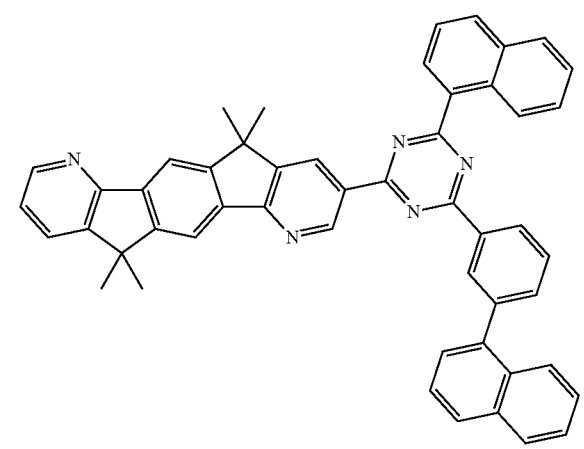
41
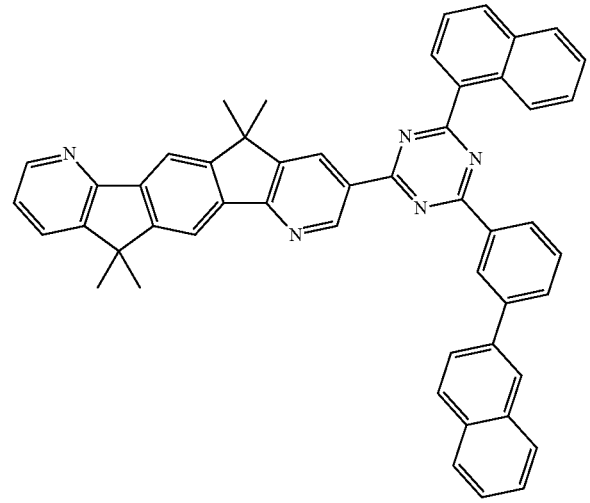
42
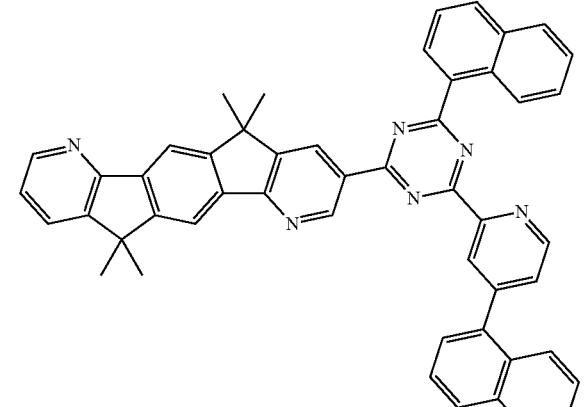

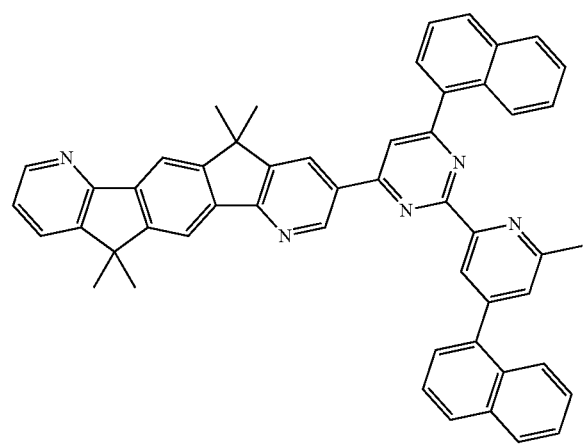
43
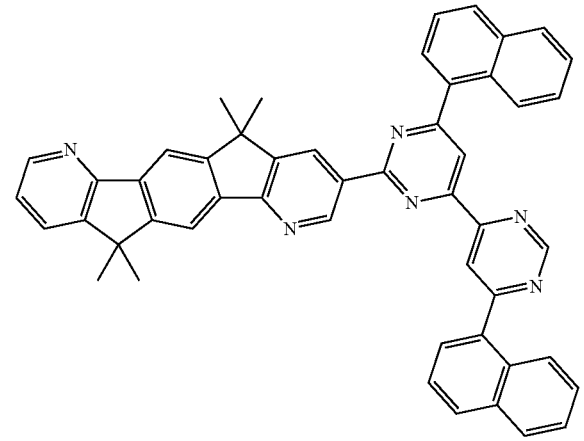
44
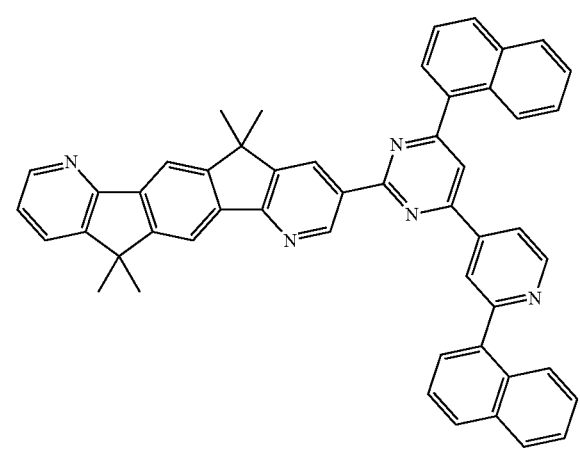
45
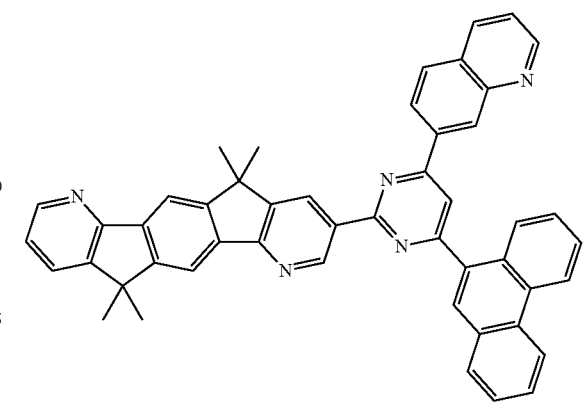
46
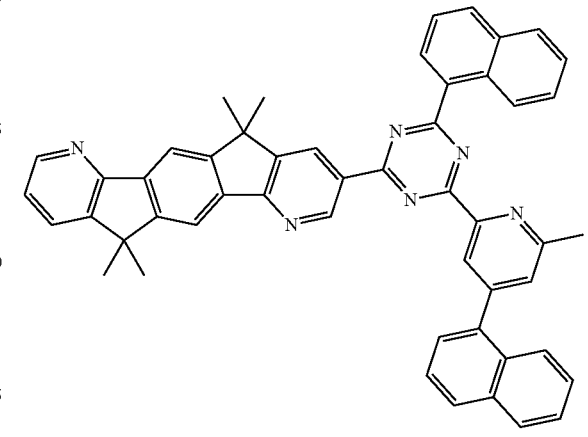
47
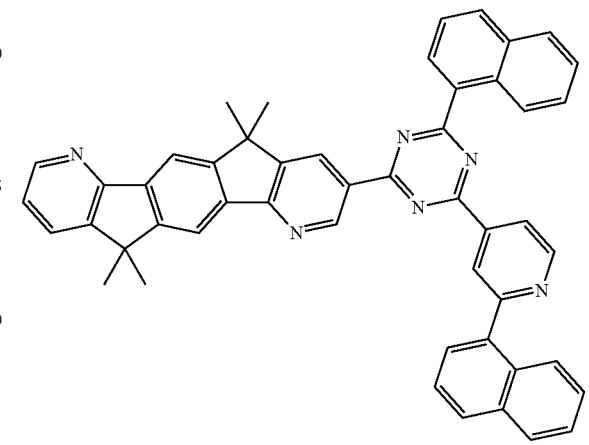
48

49
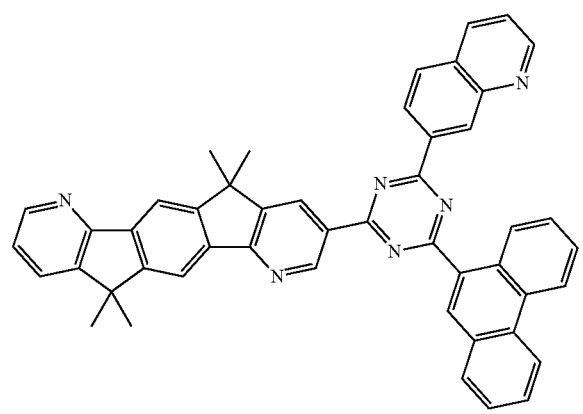
50
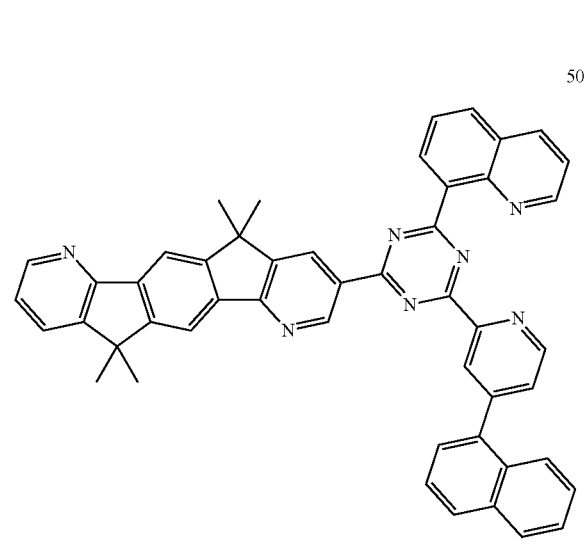
51
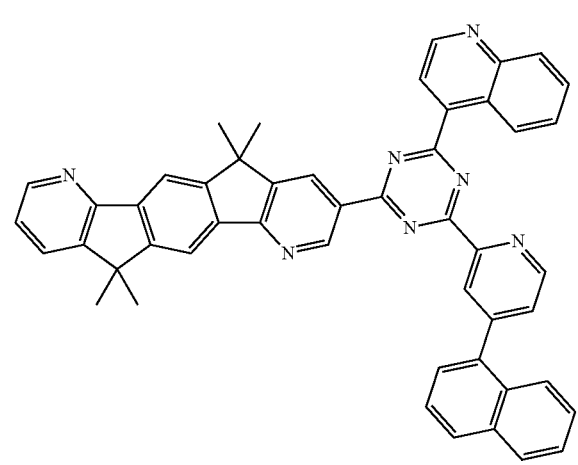
52
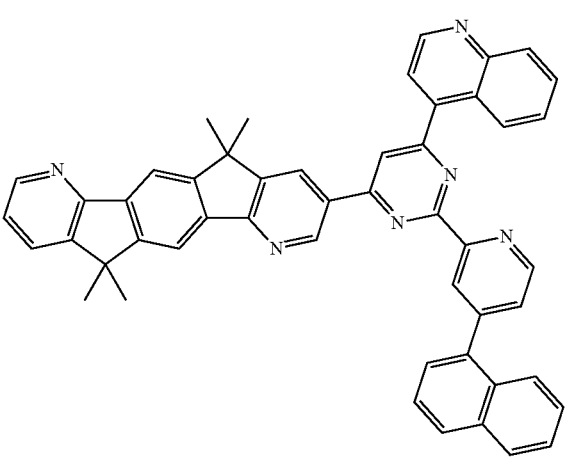
53
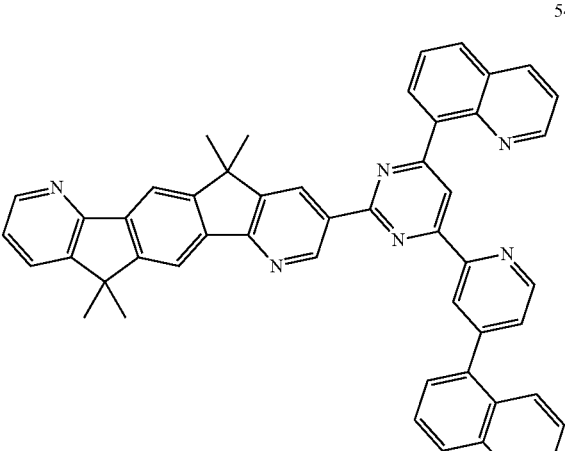
54

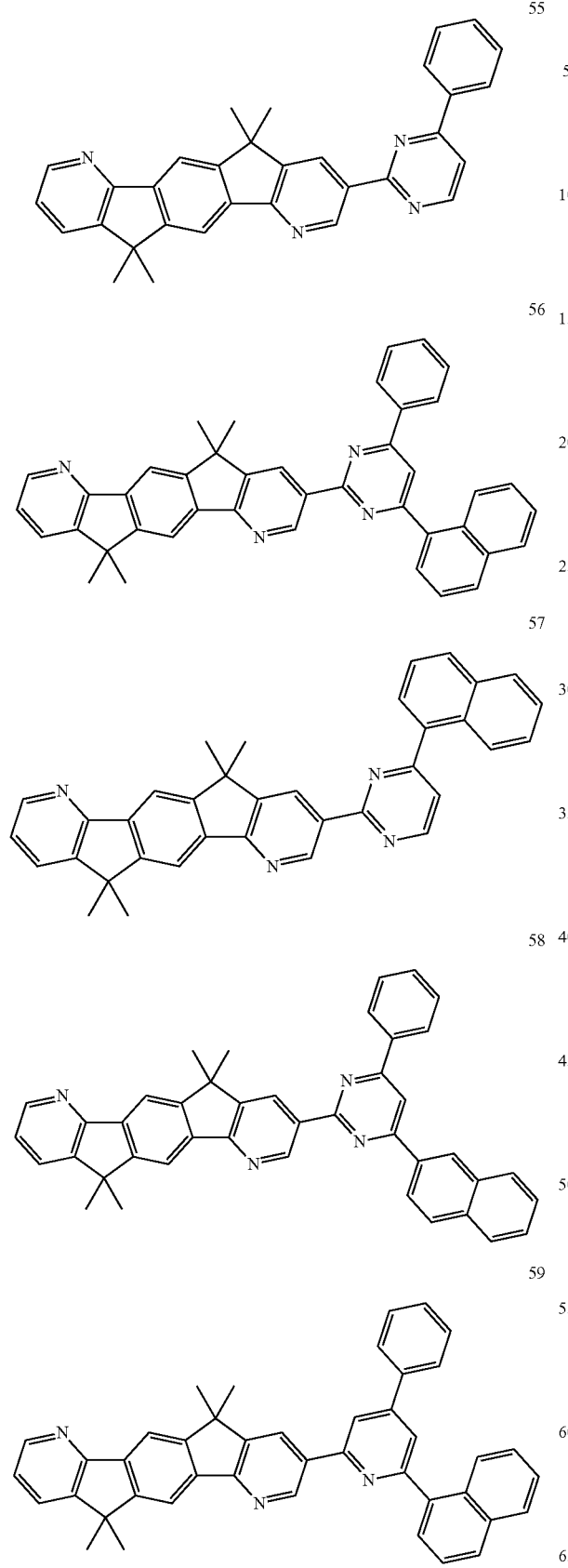
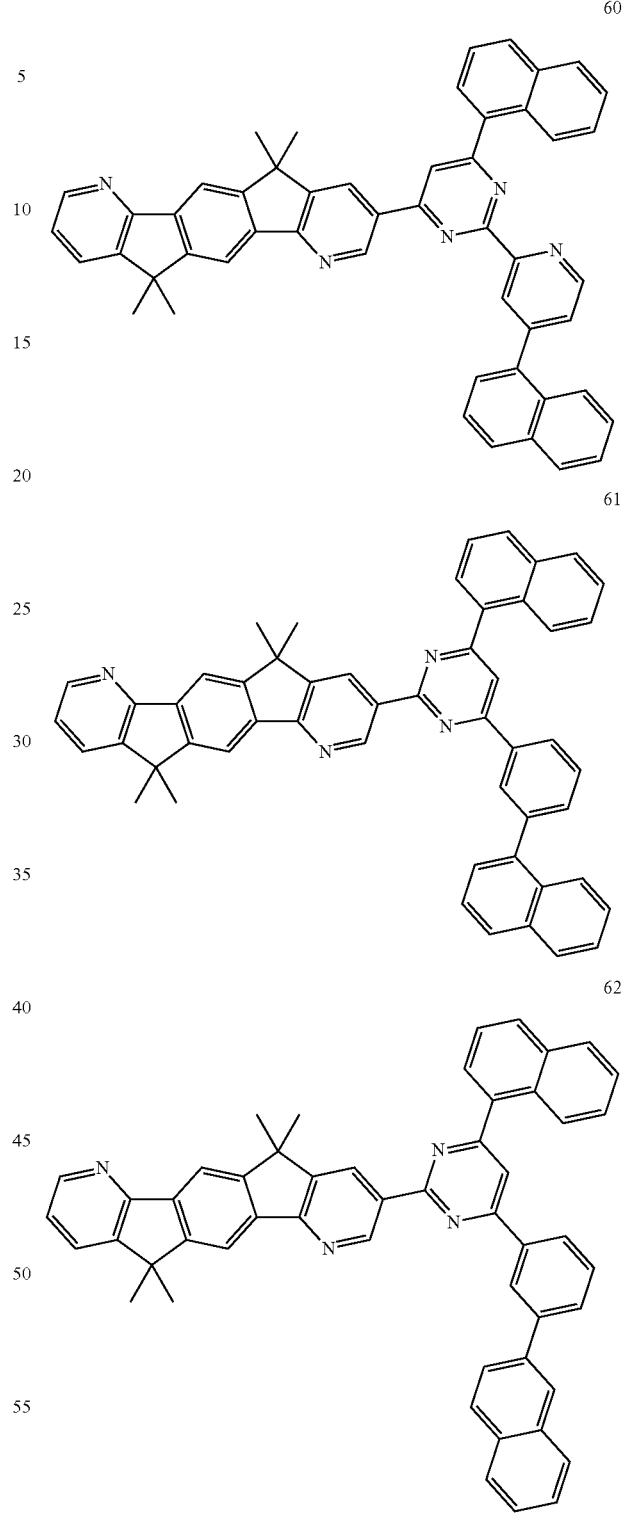

63
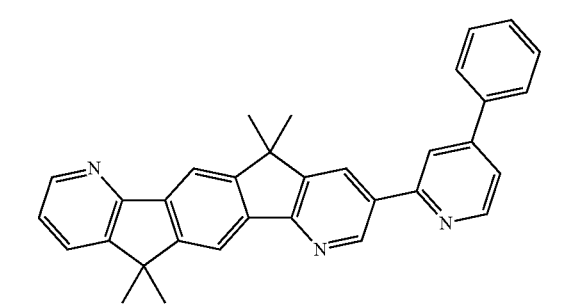
64
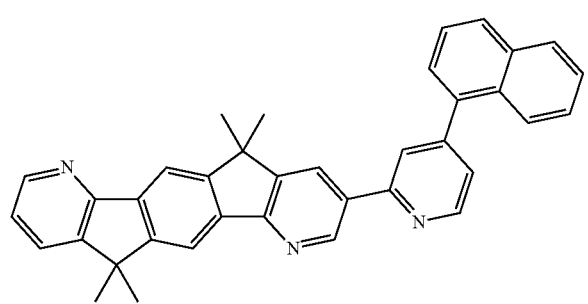
65
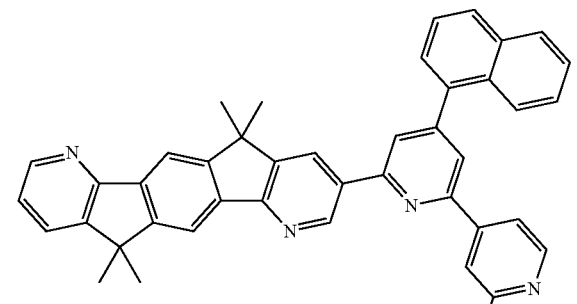
66
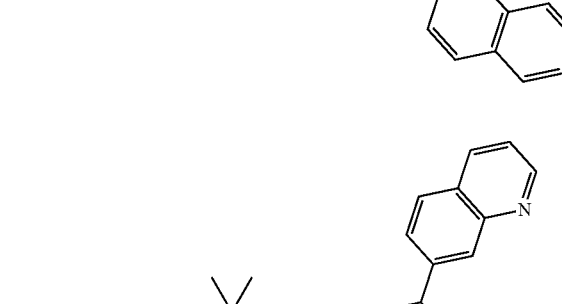
67
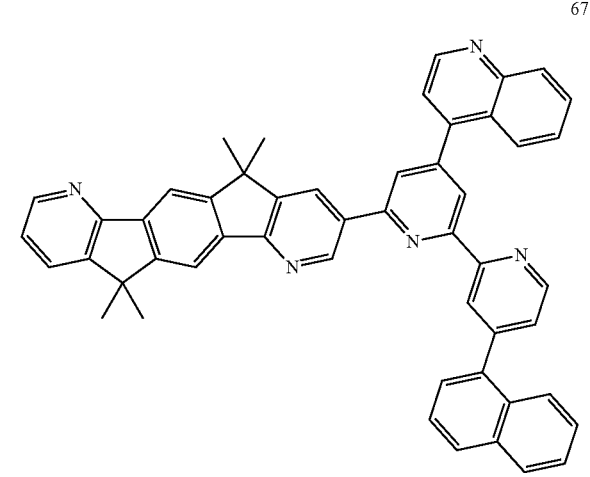
68
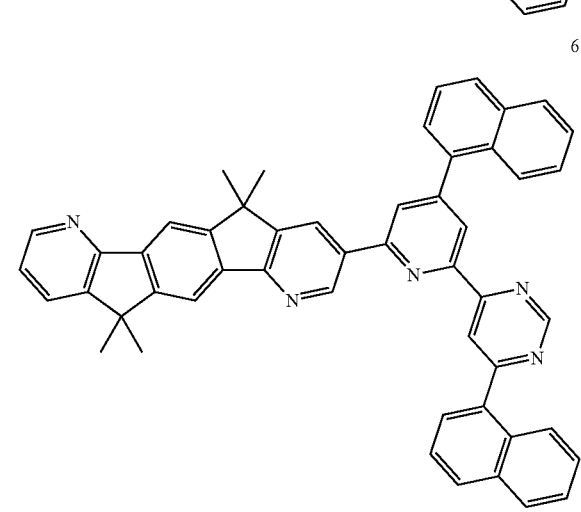
69
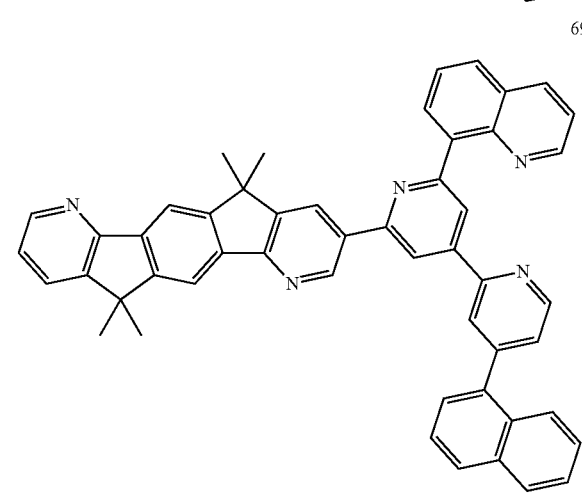

-continued

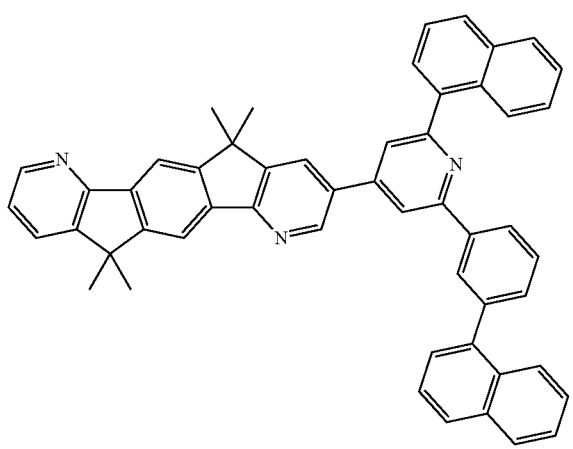
70

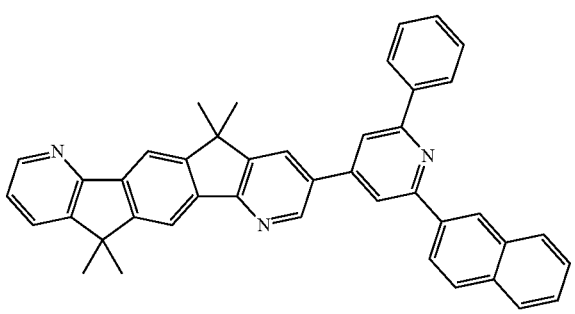
71

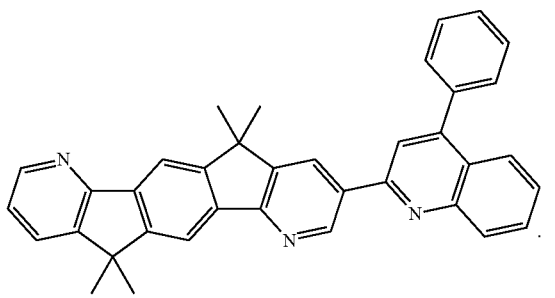
72

An organic light emitting diode device to which the above-described organic compound is applied according to an exemplary embodiment will be described with reference to FIG. 1.

FIG. 1 illustrates a cross-sectional view of an organic light emitting diode device according to an exemplary embodiment.

Referring to FIG. 1, the organic light emitting diode device may include an anode 1, a cathode 2 facing the anode 1, and an organic layer 10 provided between the anode 1 and the cathode 2.

The substrate (not shown) may be disposed on the side of the anode 1 or the cathode 2. The substrate may be made of, e.g., an inorganic material such as glass, an organic material such as polycarbonate, (PC), polymethylmethacrylate (PMMA), polyethylene terephthalate (PET), polyamide (PA), polyethersulfone (PES), or a combination thereof, a silicon wafer, or the like.

At least one of the anode 1 and the cathode 2 may be a transparent electrode formed by processing a conductive oxide such as indium tin oxide (ITO), indium zinc oxide (IZO), tin oxide ($SnO_2$), zinc oxide (ZnO), or a combination thereof, or a metal such as Al, Ag, or Mg to be thin.

The organic layer 10 may include an emission layer 5, a hole auxiliary layer 3 provided between the anode 1 and the emission layer 5, and an electron auxiliary layer 4 provided between the cathode 2 and the emission layer 5. At least one of the hole auxiliary layer 3 and the electron auxiliary layer 4 may be omitted.

The emission layer 5 may include anthracene, arylamine, styryl, a derivative thereof, or a combination thereof. The emission layer 5 may function as a fluorescent or phosphorescent host and may include a suitable dopant.

Examples of a suitable red dopant include PtOEP, $Ir(piq)_3$, $Btp_2Ir(acac)$, DCJTB, or the like.

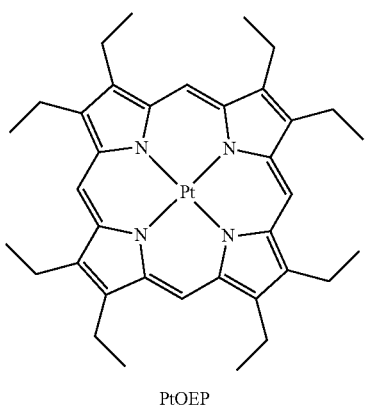
PtOEP

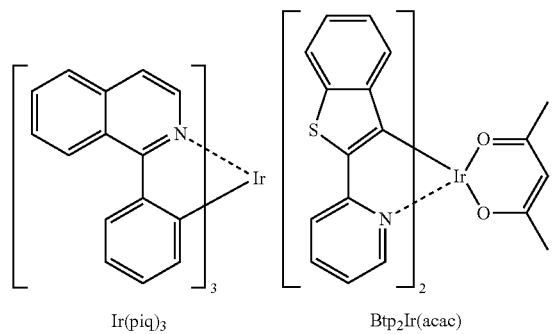
$Ir(piq)_3$    $Btp_2Ir(acac)$

Examples of a suitable green dopant include $Ir(ppy)_3$ (ppy=phenylpyridine), $Ir(ppy)_2(acac)$, $Ir(mpyp)_3$, C545T, or the like.

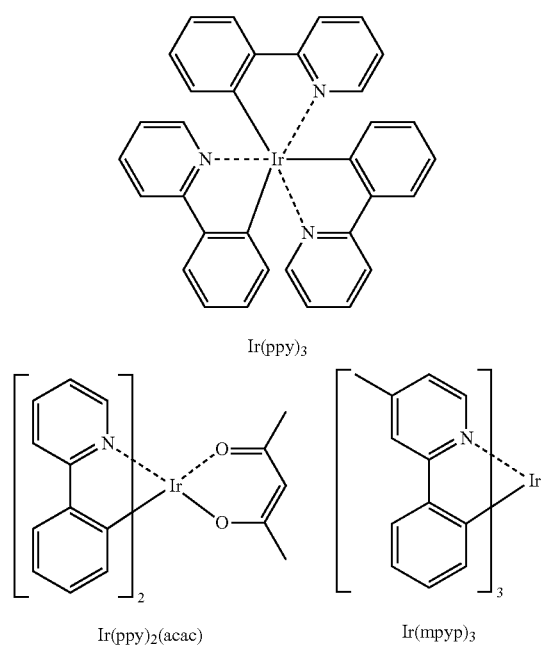
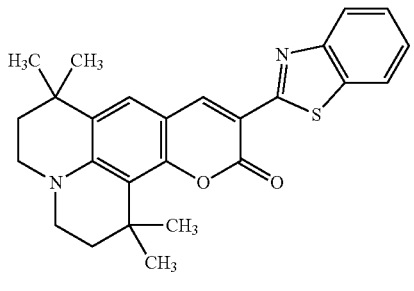
C545T
Examples of a suitable-known blue dopant include F$_2$Irpic, (F$_2$ppy)$_2$Ir(tmd), Ir(dfppz)$_3$, ter-fluorene, 4,4'-bis(4-diphenylaminostyryl) biphenyl (DPAVBi), 2,5,8,11-tetra-tert-butyl perylene (TBP), or the like.
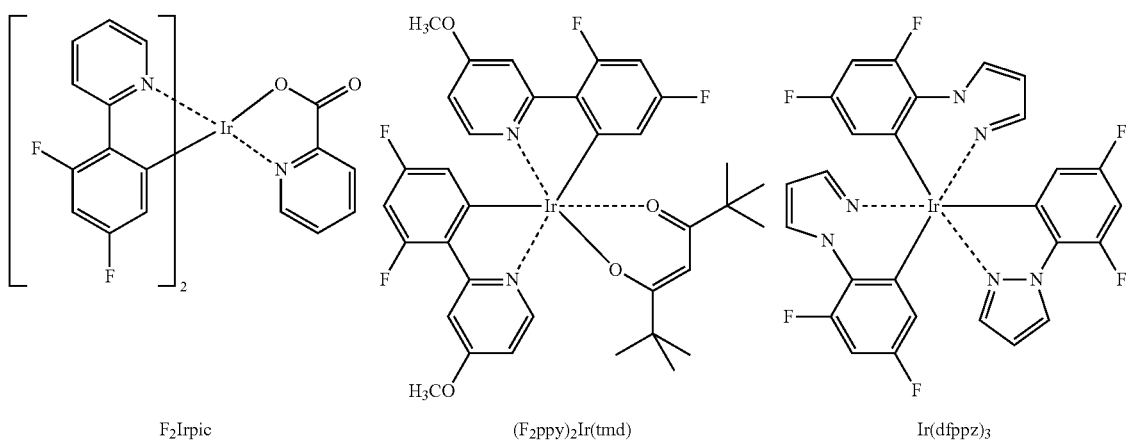
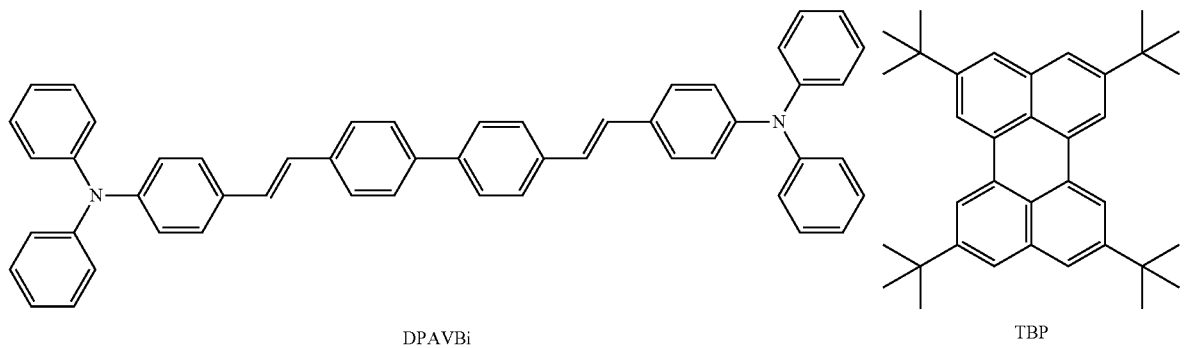

A content of the dopant may be selected, for example, within a range of 0.1 to 15 parts by weight with respect to 100 parts by weight of the emission layer forming material (i.e., the total weight of the host and the dopant is set to be 100 parts by weight).

The emission layer 5 may emit white light by a combination of the primary colors such as three primary colors of red, green, and blue. The white light may be emitted by combining the colors of neighboring subpixels or by combining colors that are deposited in the vertical direction.

The electron auxiliary layer 4 may be provided between the emission layer 5 and the cathode 2. The electron auxiliary layer 4 may increase electron mobility. The electron auxiliary layer 4 may include at least one layer selected from the electron injection layer, the electron transport layer, and the hole blocking layer.

The electron auxiliary layer 4 may include the above-described organic compound.

The hole blocking layer may include any suitable material to form a hole blocking layer. The suitable material used to form the hole blocking layer may be randomly selected. For example, oxadiazole derivatives, triazole derivatives, phenanthroline derivatives, Balq, BCP, or the like may be used.

The electron transport layer may include the organic compound represented by Formula 1.

The hole auxiliary layer 3 may be provided between the emission layer 5 and the anode 1 to increase hole mobility. The hole auxiliary layer 3 may exemplarily include at least one layer selected from among the hole injection layer, the hole transport layer, and the electron blocking layer.

A suitable hole injection material may be for the hole injection layer. For example, the hole injection material may be a phthalocyanine compound such as copper phthalocyanine or the like, m-MTDATA (4,4',4"-tris(3-methylphenyl-phenylamino)triphenylamine), NPB (N,N'-di(1-naphthyl)-N,N-diphenylbenzidine(N,N-di(1-naphthyl)-N,N-diphenylbenzidine)), TDATA, 2T-NATA, Pani/DB SA (polyaniline/dodecylbenzene sulfonic acid:polyaniline/dodecylbenzene sulfonic acid), PEDOT/PSS (poly(3,4-ethylene dioxythiophene)/poly(4-styrene sulfonate):poly(3,4-ethylene dioxythiophene)/poly(4-styrene sulfonate)), Pani/CSA (polyaniline/camphor sulfonic acid:polyaniline/camphor sulfonic acid), or Pani/PSS (((polyaniline)/poly(4-styrene sulfonate):polyaniline)/poly(4-styrene sulfonate)).

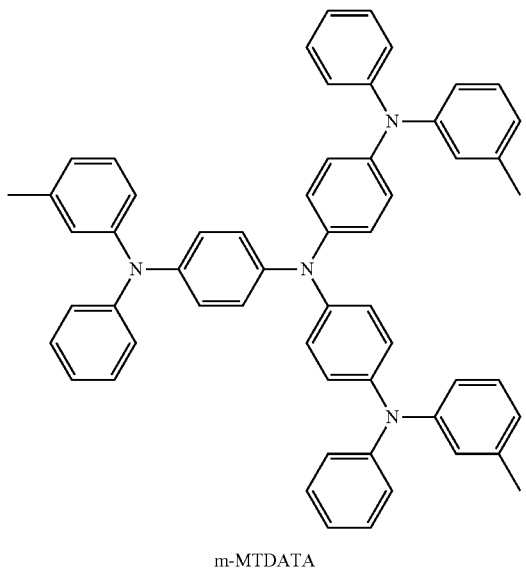

m-MTDATA

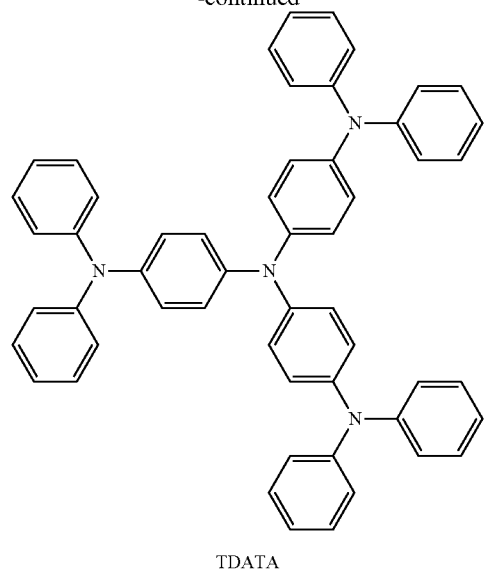

TDATA

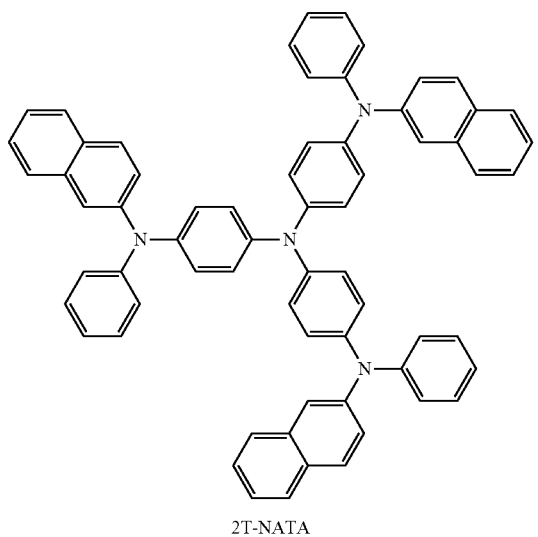

2T-NATA

The hole transport layer may include a suitable hole transport material, for example, a carbazole derivative such as N-phenylcarbazole, polyvinylcarbazole, or the like, and an amine derivative having an aromatic condensed ring such as NPB, N,N'-bis(3-methylphenyl)-N,N'-diphenyl-[1,1-biphenyl]-4,4'-diamine (TPD), or the like. For example, the hole transport material may transport holes and prevent the excitons from spreading from the emission layer.

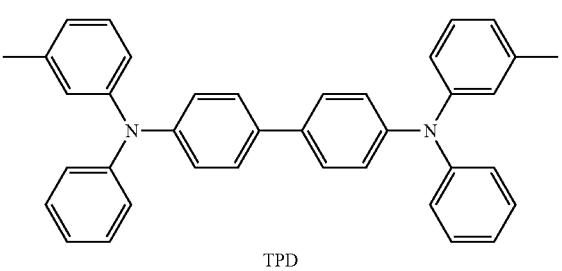

TPD

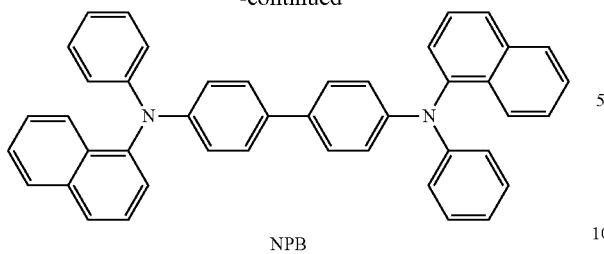

NPB

The organic light emitting diode device may be configured in the form of anode/hole injection layer/emission layer/electron transport layer/cathode, anode/hole injection layer/hole transport layer/emission layer/electron transport layer/cathode, or anode/hole injection layer/hole transport layer/emission layer/electron transport layer/electron injection layer/cathode.

The organic layer 10 may be formed by various methods, for example, a vacuum deposition method, a spin coating method, a cast method, or an LB method.

When the organic layer is formed by the vacuum deposition method, deposition conditions may depend on the compound used as a material of the organic layer, the structure of the target organic layer, and thermal characteristics. For example, deposition conditions may include a deposition temperature 100 to 500° C., a vacuum degree $10^{-8}$ to $10^{-3}$ torr, and a deposition speed 0.01 to 100 Å/sec.

When the organic layer is formed by the spin coating method, coating conditions may depend on the compound used as a material of the organic layer, the structure of the target organic layer, and thermal characteristics. For example, deposition conditions may include a coating speed of about 2,000 rpm to about 5,000 rpm, and a heat treatment temperature for removing a solvent after the coating in a temperature range of about 80° C. to 200° C.

The organic layer 10 may include a first layer including the organic compound represented by Formula 1. The first layer may be the electron transport layer.

The organic layer 10 may further include at least one of the hole injection layer, the hole transport layer, the electron blocking layer, the hole blocking layer, the electron transport layer, and the electron injection layer in addition to the electron transport layer.

The organic light emitting diode device may be electrically connected to a thin film transistor. The thin film transistor may be disposed between the substrate and the electrode.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHESIS EXAMPLES

Synthesis Example 1

Synthesis of Compound 1

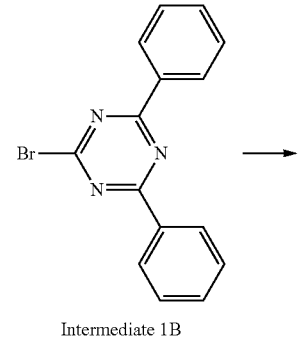

Intermediate 1A

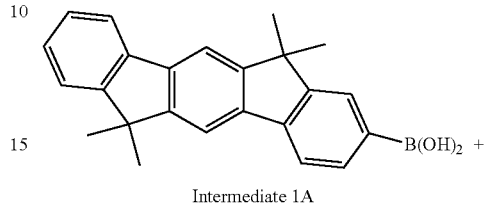

Intermediate 1B

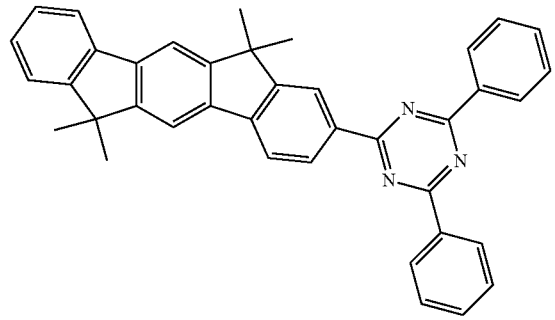

Compound 1

Synthesis of Compound 1

In a nitrogen atmosphere, the intermediate 1A (2.1 g, 6 mmol), the intermediate 1B (1.6 g, 5 mmol), Pd(PPh$_3$)$_4$ (0.23 g, 0.2 mmol), 3 mL of a 2 M K$_2$CO$_3$ aqueous solution, 10 mL of toluene, and 5 mL of ethanol were provided and then refluxed and agitated for twelve hours. A resultant material was rinsed with distilled water, and an organic material was extracted by using ethyl acetate. The extracted organic material was dried with anhydride MgSO$_4$, decompressed, and distilled. 1.1 g (41%) of the intermediate compound 1 was acquired by column-separating the resultant material.

H-NMR (CDCl$_3$, 300 MHz, ppm): 8.4-8.3 (m, 4H), 8.2-8.1 (m, 2H), 7.8-7.9 (m, 3H), 7.7-7.4 (m, 10H), 1.7 (s, 12H).

Synthesis Example 2

Synthesis of Compound 4

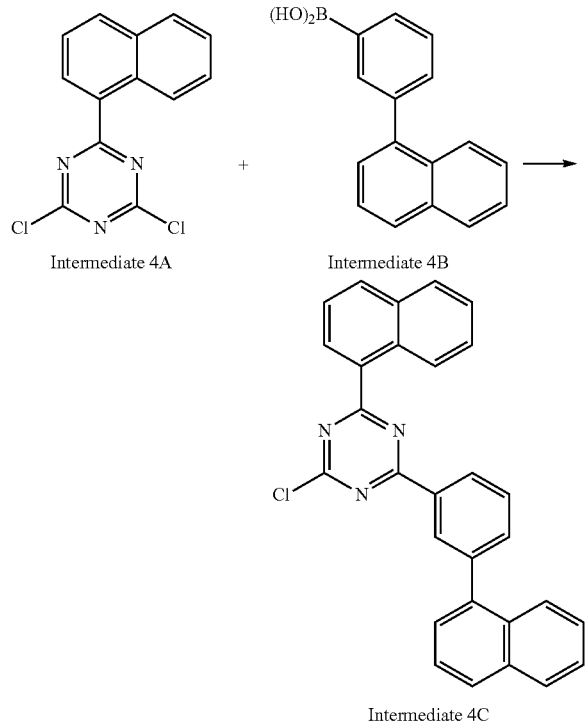

Intermediate 4A    Intermediate 4B

Intermediate 4C

Synthesis of Intermediate 4C

The intermediate 4C (1.4 g, 63%) was synthesized using the same method as the synthesis method of the compound 1, except for the usage of the intermediate 4A instead of the intermediate 1B and usage of the intermediate 4B instead of the intermediate 1A.

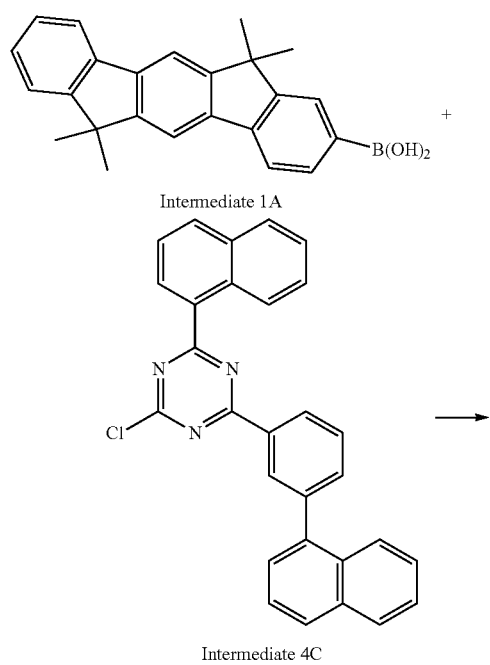

Intermediate 1A

Intermediate 4C

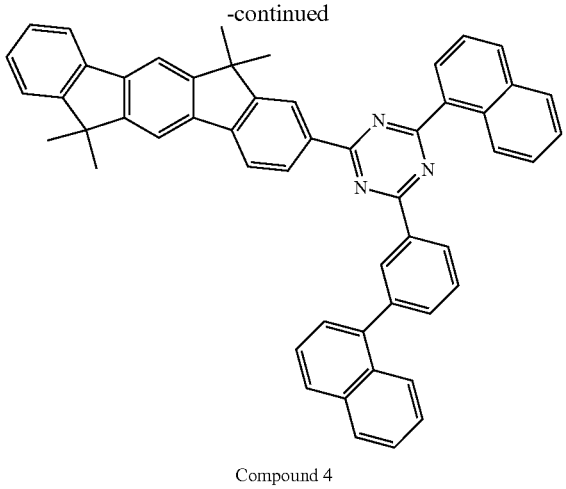

Compound 4

Synthesis of Compound 4

The compound 4 (0.9 g, 58%) was synthesized using the same method as the synthesis method of the compound 1, except for the usage of the intermediate 4C instead of the intermediate 1B.

H-NMR (CDCl$_3$, 300 MHz, ppm): 9.0-8.9 (m, 2H), 8.5-8.1 (m, 9H), 7.9-7.8 (m, 5H), 7.7-7.6 (m, 4H), 7.5-7.4 (m, 7H), 1.7 (s, 12H).

Synthesis Example 3

Synthesis of Compound 7

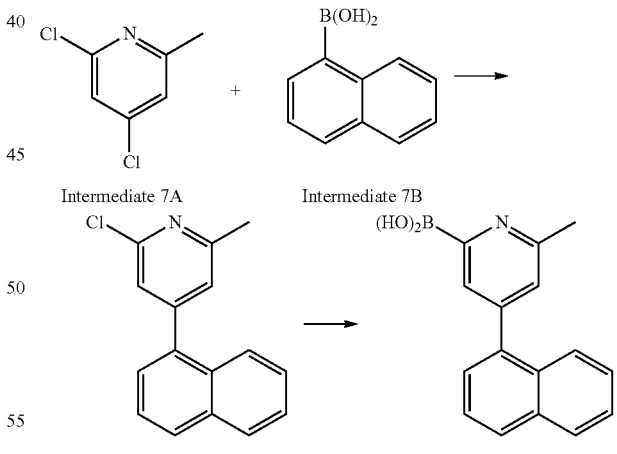

Intermediate 7A    Intermediate 7B

Intermediate 7C    Intermediate 7D

Synthesis of Intermediate 7C

The intermediate 7C (2.7 g, 43%) was synthesized using the same method as the synthesis method of the compound 1, except for the usage of the intermediate 7A instead of the intermediate 1B and usage of the intermediate 7B instead of the intermediate 1A.

Synthesis of Intermediate 7D

At room temperature, the intermediate 7C (5.1 g, 20 mmol) was melted in a flask in which 100 mL tetrahydrofuran was provided. The temperature of the flask was reduced to −78° C., n-butillithium (18 mL, 30.0 mol) was slowly added at the temperature, and triisopropyl borate (5.5 mL, 25.0 mmol) was added at the same temperature. The temperature of the flask was gradually increased to reach room temperature overnight to progress a reaction. When the reaction was finished, a 1N-hydrochloric acid aqueous solution was added to the flask until reaching pH 2 to acidify the reaction solution. The acidified reaction solution was extracted with ethyl acetate and the extracted organic layer was rinsed with purified water. The organic layer was separated from the ethyl acetate to be dried with sulfuric acid anhydride magnesium and filtered. A filtrate was concentrated to recrystallize the same with dichloromethane and n-hexane, such that the intermediate 7D (3.8 g, 74%) was acquired.

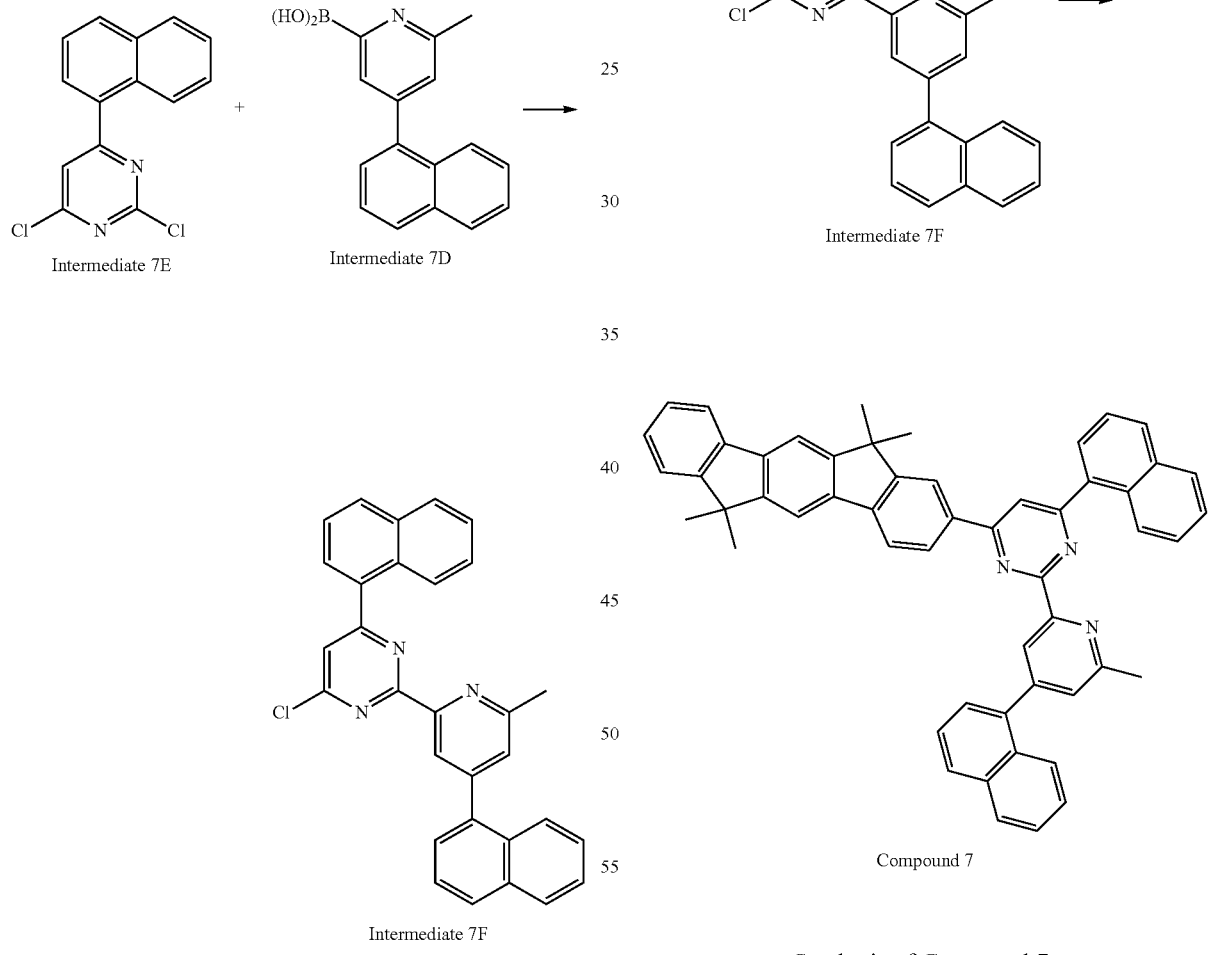

Synthesis of Intermediate 7F

The intermediate 7F (1.2 g, 38%) was synthesized using the same method as the synthesis method of the compound 1, except for the usage of the intermediate 7E instead of the intermediate 1B and usage of the intermediate 7D instead of the intermediate 1A.

Synthesis of Compound 7

The compound 7 (0.8 g, 60%) was synthesized using the same method as the synthesis method of the compound 1, except for the usage of the intermediate 7F instead of the intermediate 1B.

H-NMR (CDCl$_3$, 300 MHz, ppm): 9.0-8.9 (m, 3H), 8.5 (s, 1H), 8.4 (s, 1H), 8.3-8.1 (m, 7H), 7.9-7.8 (m, 6H), 7.7-7.4 (m, 8H), 2.7 (s, 3H), 1.7 (s, 12H).

Synthesis Example 4

Synthesis of Compound 11

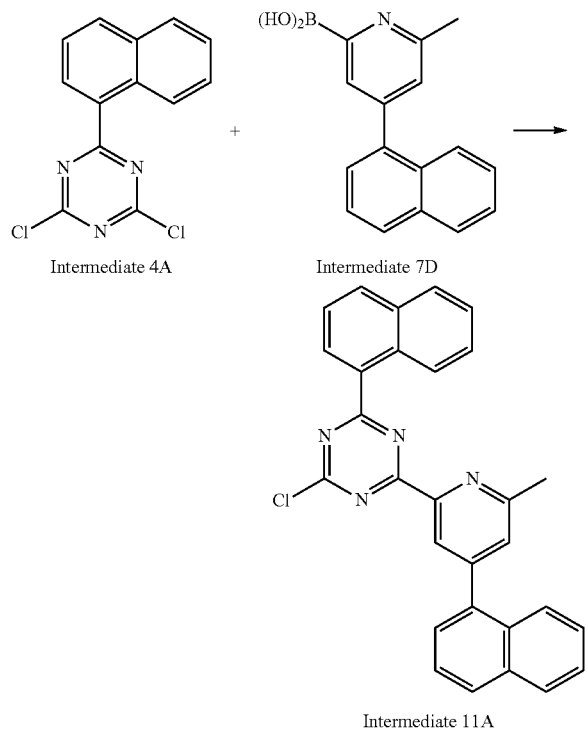

Intermediate 4A    Intermediate 7D

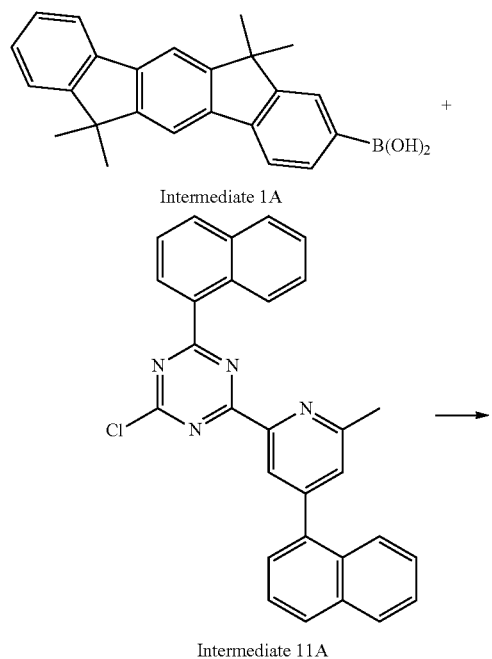

Intermediate 11A

Synthesis of Intermediate 11A

The intermediate 11A (1.8 g, 69%) was synthesized using the same method as the synthesis method of the compound 1, except for the usage of the intermediate 4A instead of the intermediate 1B and usage of the intermediate 7D instead of the intermediate 1A.

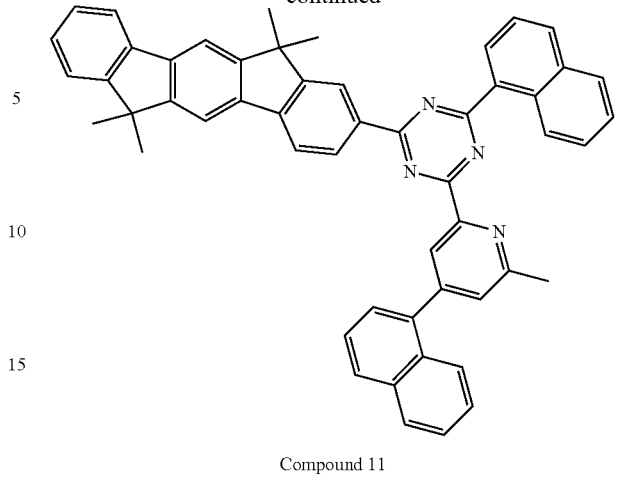

Compound 11

Synthesis of Compound 11

The compound 11 (0.9 g, 64%) was synthesized by using the same method as the synthesis method of the compound 1, except for the usage of the intermediate 11A instead of the intermediate 1B.

H-NMR (CDCl₃, 300 MHz, ppm): 9.0-8.9 (m, 3H), 8.5 (s, 1H), 8.3-8.1 (m, 7H), 7.9-7.8 (m, 6H), 7.7-7.3 (m, 8H), 2.7 (s, 3H), 1.7 (s, 12H).

Synthesis Example 5

Synthesis of Compound 17

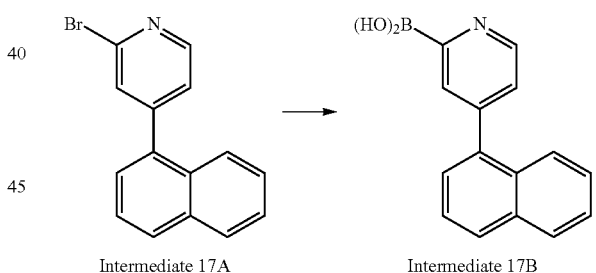

Intermediate 17A    Intermediate 17B

Synthesis of Intermediate 17B

The intermediate 17B (2.3 g, 56%) was synthesized using the same method as the synthesis method of the compound 1, except for the usage of the intermediate 17A instead of the intermediate 7C.

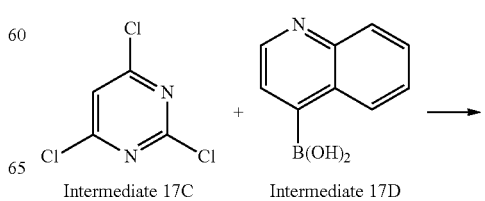

Intermediate 17C    Intermediate 17D

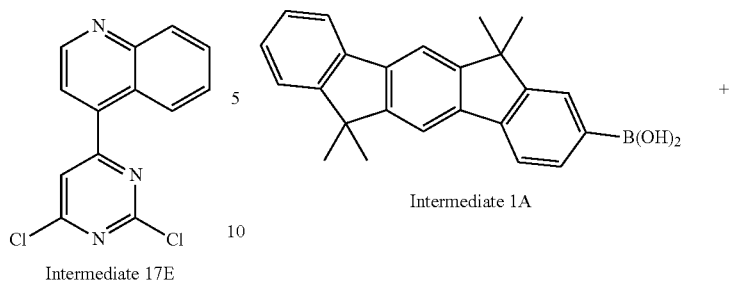

Intermediate 17E

Intermediate 1A

Synthesis of Intermediate 17E

The intermediate 17E (1.1 g, 17%) was synthesized by using the same method as the synthesis method of the compound 1, except for the usage of the intermediate 17C instead of the intermediate 1B and usage of the intermediate 17D instead of the intermediate 1A.

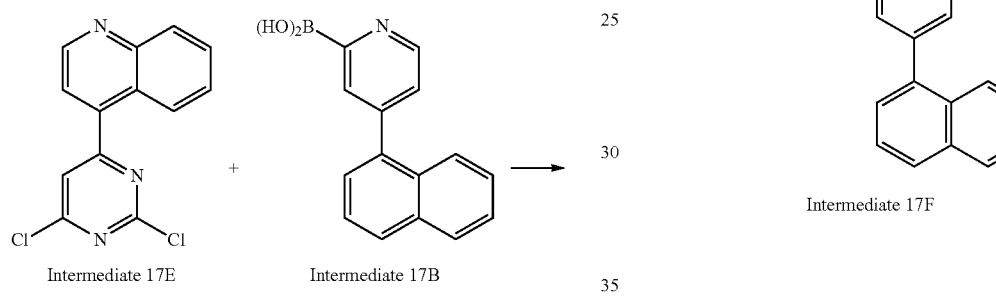

Intermediate 17E + Intermediate 17B → Intermediate 17F

Intermediate 17F

Synthesis of Intermediate 17F

The intermediate 17E (1.2 g, 27%) was synthesized by using the same method as the synthesis method of the compound 1, except for the usage of the intermediate 17E instead of the intermediate 1B and usage of the intermediate 17B instead of the intermediate 1A.

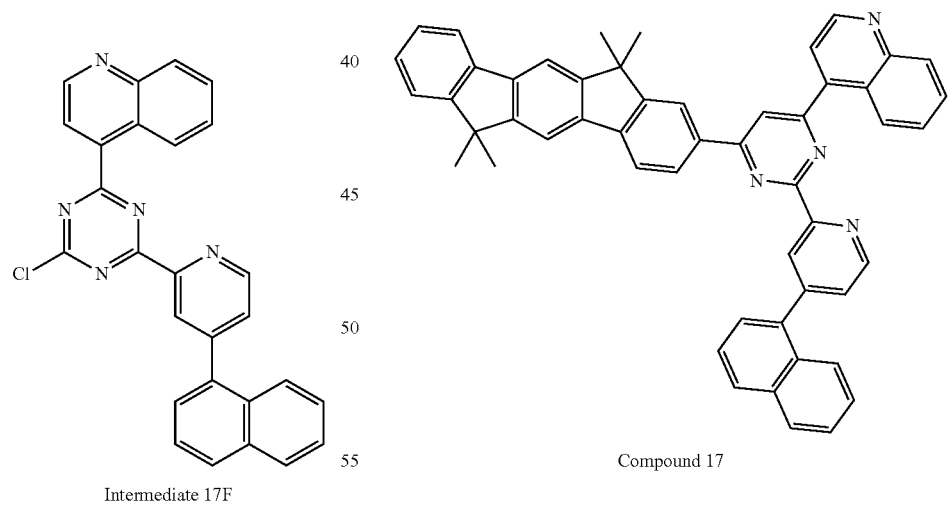

Compound 17

Synthesis of Compound 17

The compound 17 (0.6 g, 51%) was synthesized using the same method as the synthesis method of the compound 1, except for the usage of the intermediate 17F instead of the intermediate 1B.

H-NMR (CDCl$_3$, 300 MHz, ppm): 9.1 (d, 1H), 8.9-8.8 (m, 3H), 8.6-8.5 (m, 3H), 8.3-8.1 (m, 5H), 7.9-7.7 (m, 9H), 7.6-7.4 (m, 5H), 1.7 (s, 12H).

Synthesis Example 6

Synthesis of Compound 22

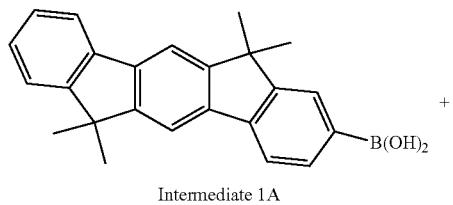

Intermediate 1A

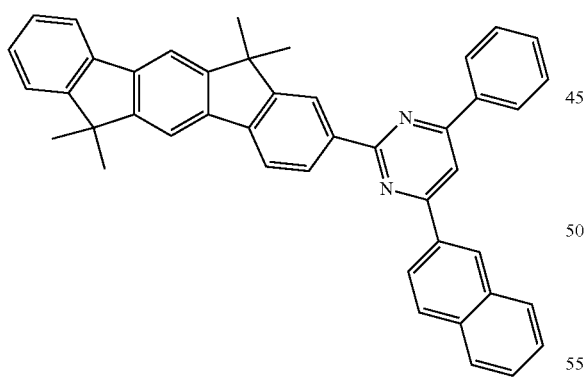

Intermediate 22A

Compound 22

Synthesis of Compound 22

The compound 22 (0.8 g, 42%) was synthesized by using the same method as the synthesis method of the compound 1, except for the usage of the intermediate 22A instead of the intermediate 1B.

H-NMR (CDCl$_3$, 300 MHz, ppm): 8.4-8.2 (m, 3H), 8.1-7.9 (m, 10H), 7.7-7.4 (m, 9H), 1.7 (s, 12H).

Synthesis Example 7

Synthesis of Compound 28

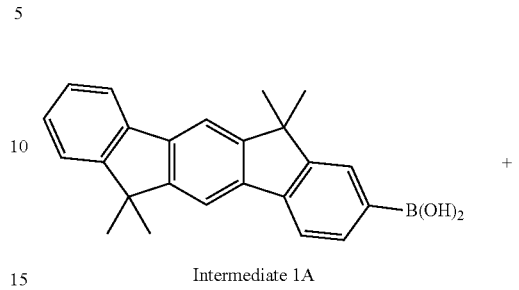

Intermediate 1A

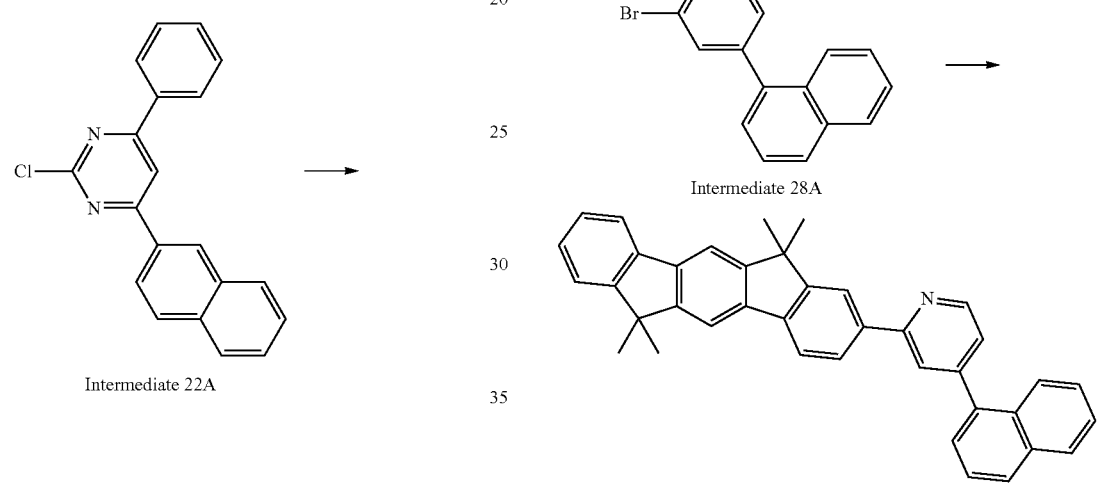

Intermediate 28A

Compound 28

Synthesis of Compound 28

The compound 28 (1.1 g, 65%) was synthesized by using the same method as the synthesis method of the compound 1, except for the usage of the intermediate 28A instead of the intermediate 1B.

H-NMR (CDCl$_3$, 300 MHz, ppm): 8.9-8.6 (m, 4H), 8.3-8.1 (m, 6H), 8.0-7.7 (m, 5H), 7.6-7.4 (m, 4H), 1.7 (s, 12H).

Synthesis Example 8

Synthesis of Compound 39

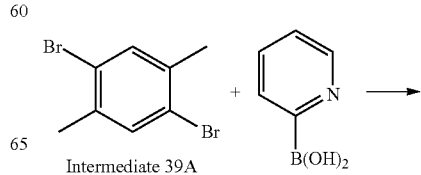

Intermediate 39A

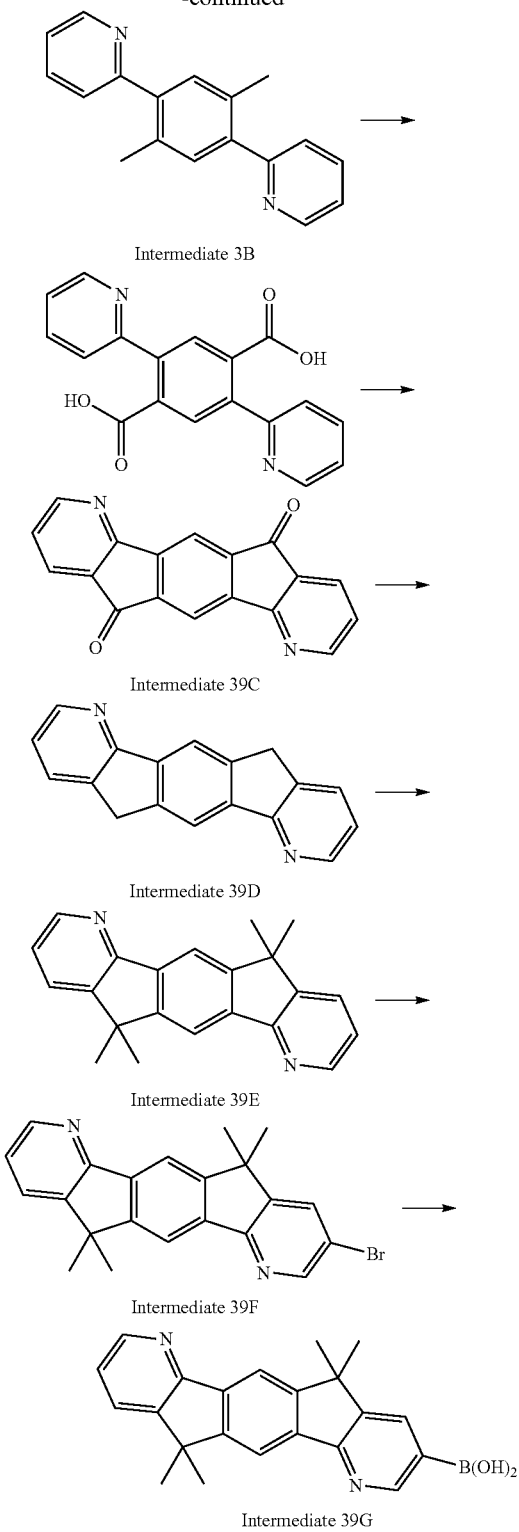

Intermediate 3B

Intermediate 39C

Intermediate 39D

Intermediate 39E

Intermediate 39F

Intermediate 39G

Synthesis of Intermediate 39A

The intermediate 39A was synthesized by using the same method as the synthesis method of the compound 1, except for the usage of 1,4-dibromo-3,5-dimethylbenzene instead of the intermediate 1B and usage of 2-pyridylboronic acid in the 3.0 equivalence instead of the intermediate 1A.

Synthesis of Intermediate 39B

The intermediate 39A (2.60 g, 10.0 mmole), 7.40 g potassium permanganate, and 5 ml water were put into pyridine (50 ml) and refluxed for two hours. After this, 10 ml water and 3.00 g potassium permanganate were added every thirty minutes. After six additions, 50 ml water was added and refluxed for twelve hours. A $MnO_2$ precipitate formed after the reaction was finished was removed using hot water, and celite and activated carbon was used to filter the resultant again. A solid generated by adding heavy HCl was filtered, taken, and dried with an oven, such that the intermediate 39B (2.90 g, and a 90% yield) was acquired.

Synthesis of Intermediate 39C

The intermediate 39B (2.90 g, 9.0 mmole) was melted in 100 ml $H_2SO_4$ and was agitated for two hours at room temperature. The flask was moved to an ice bath after the reaction was finished, a formed solid was neutralized by using a potassium carbonate aqueous solution, and the solid was filtered and gathered, so that the intermediate 39C (2.07 g, a 81% yield) was acquired.

Synthesis of Intermediate 39D

The intermediate 39C (2.07 g, 7.3 mmole) and hydrazine monohydrate (98%, 10 ml) were put into 150 ml ethylene glycol, and 8.6 g KOH was added thereto, and the reaction solution was refluxed for 24 hours. A hot reaction solution was poured into an ice-added HCl solution and a formed solid was filtered. The acquired solid was recrystallized to provide the intermediate 39D (1.65 g, a 90% yield).

Synthesis of Intermediate 39E

In a nitrogen atmosphere, the intermediate 39D (1.65 g, 6.44 mmole) was put into a flask including 200 mL THF, and cooled at −78° C. N-BuLi (1.6 M in Hex.) (9.0 ml, 14.4 mmole) was slowly added and the solution was agitated for one hour at −78° C. $CH_3I$ (1.08 ml, 17.3 mmole) was added, the temperature was slowly controlled to reach room temperature, and the solution was then agitated for one and a half hours, Then, the solution was cooled down again to −78° C., n-BuLi (1.6 M in Hex.) (10.8 ml, 17.3 mmole) was slowly added, the solution was agitated for one hour at −78° C., and $CH_3I$ (1.25 ml, 20.1 mmole) was added, the solution was controlled to reach room temperature, and agitated for an hour. When the reaction was finished, the resultant was rinsed with distilled water, extracted with $CH_2Cl_2$, dried with anhydride $MgSO_4$, decompressed, and distilled. The acquired solid was put into the flask with 200 mL hexane which was agitated and boiled. In this instance, materials that were not melted after the hexane was boiled were filtered and dried, such that the intermediate 39E (1.13 g, a 56% yield) was acquired.

Synthesis of Intermediate 39F

The intermediate 39E (1.13 g, 3.6 mmol) was put into a 30 mL round-bottomed flask, which was vacuum-dried and filled with nitrogen gas. 10 mL chloroform was put into the flask and the flask was then wrapped with foil to exclude light. The flask was cooled to 0° C., 10 mg $FeCl_3$ (58 μmol)

was put into the flask, and 3 mL chloroform and 0.7 g (4.0 mmol) bromine were melted and provided for half an hour. The temperature was raised to reach room temperature and the flask was agitated for five hours. When the reaction was finished, the above-noted mixture was poured into a 15 mL saturated sodium thiosulfate aqueous solution, which was agitated until a red color disappeared. The resultant was extracted with chloroform, dried with anhydride MgSO$_4$, decompressed, and distilled. The acquired material was put into a flask with 200 mL hexane, agitated and boiled. In this instance, after the hexane was heated, the materials that were not melted were filtered and dried, such that the intermediate 39F (0.7 g, a 51% yield) was acquired.

Synthesis of Intermediate 39G

The intermediate 39G (0.5 g, 76%) was synthesized by using the same method as the synthesis method of the compound 7D, except for the usage of the intermediate 39F instead of the intermediate 7C.

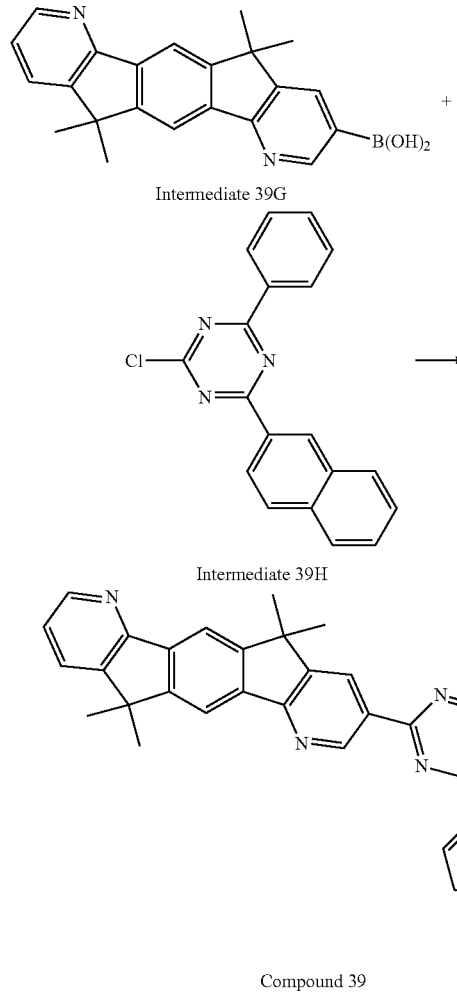

1, except for the usage of the intermediate 39G instead of the intermediate 1A and usage of the intermediate 39H instead of the intermediate 1B.

H-NMR (CDCl$_3$, 300 MHz, ppm): 9.1-8.9 (m, 2H), 8.5-8.3 (m, 6H), 8.2-8.0 (m, 3H), 7.8-7.3 (m, 7H), 6.8 (t, 1H), 1.7 (s, 12H).

Synthesis Example 9

Synthesis of Compound 43

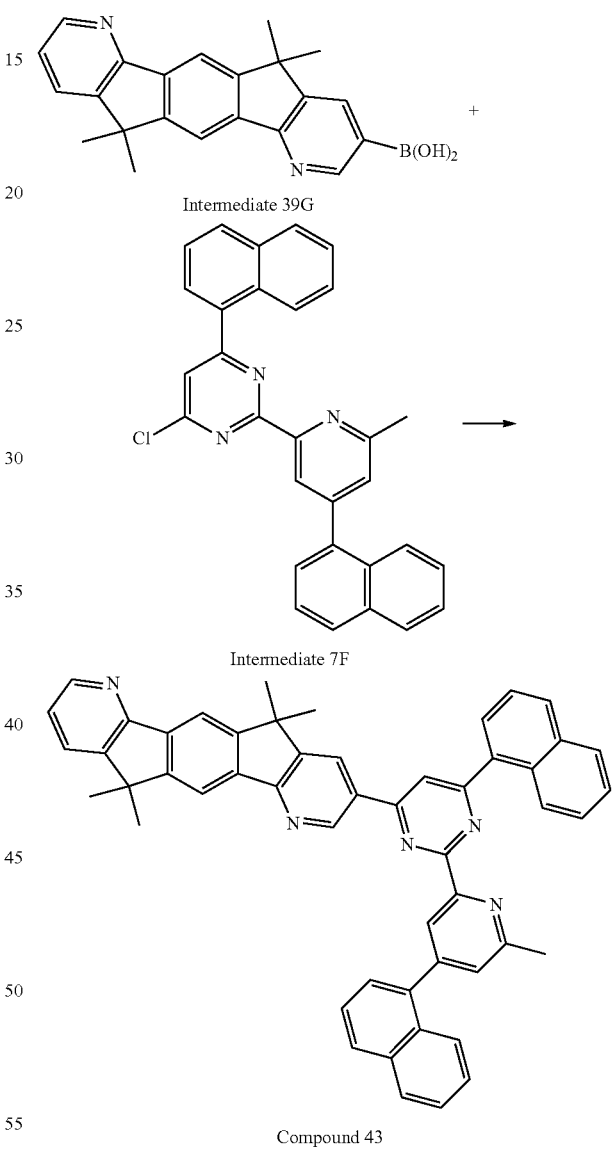

Synthesis of Compound 43

The compound 43 (0.5 g, 34%) was synthesized by using the same method as the synthesis method of the compound 39, except for the usage of the intermediate 7F instead of the intermediate 39H.

H-NMR (CDCl$_3$, 300 MHz, ppm): 9.0-8.9 (m, 4H), 8.5-8.3 (m, 7H), 8.2-8.0 (m, 6H), 7.8-7.3 (m, 6H), 6.7 (t, 1H), 2.7 (s, 3H), 1.7 (s, 12H).

Synthesis of Compound 39

The compound 39 (0.8 g, 48%) was synthesized by using the same method as the synthesis method of the compound

Synthesis Example 10

Synthesis of Compound 47

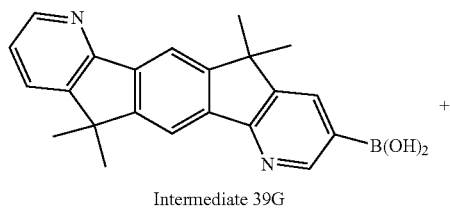

Intermediate 39G

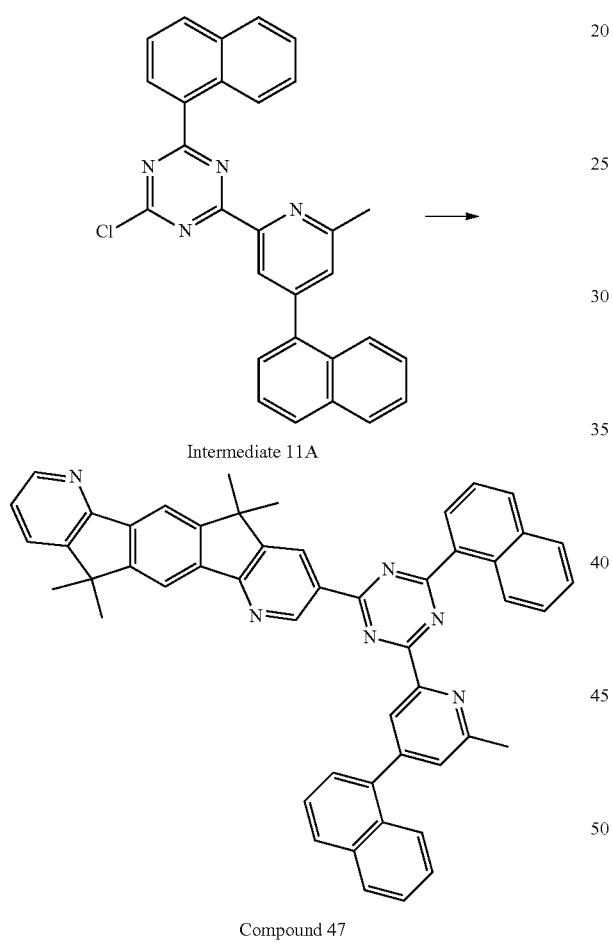

Compound 47

Synthesis of Compound 47

The compound 47 (0.6 g, 41%) was synthesized by using the same method as the synthesis method of the compound 39, except for the usage of the intermediate 11A instead of the intermediate 39H.

H-NMR (CDCl$_3$, 300 MHz, ppm): 9.0-8.9 (m, 4H), 8.5-8.0 (m, 12H), 7.8-7.3 (m, 6H), 6.7 (t, 1H), 2.7 (s, 3H), 1.7 (s, 12H).

Synthesis Example 11

Synthesis of Compound 51

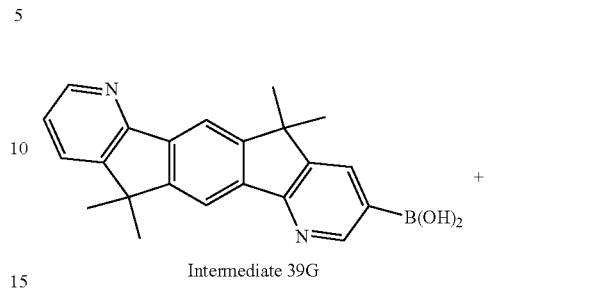

Intermediate 39G

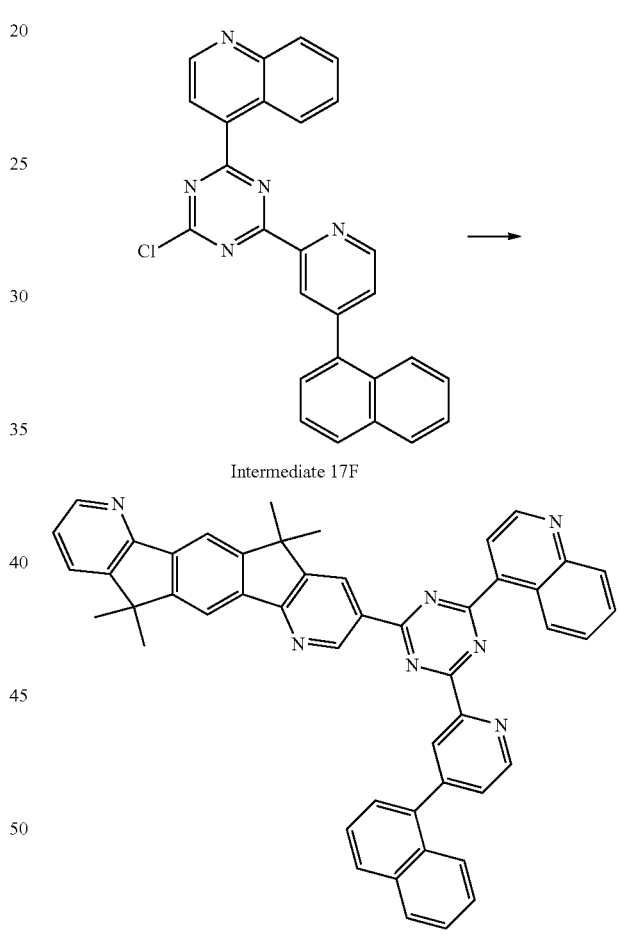

Compound 51

Synthesis of Compound 51

The compound 51 (0.5 g, 37%) was synthesized by using the same method as the synthesis method of the compound 39, except for the usage of the intermediate 17F instead of the intermediate 39H.

H-NMR (CDCl$_3$, 300 MHz, ppm): 9.1-8.5 (m, 7H), 8.4-8.1 (m, 6H), 8.0-7.3 (m, 9H), 6.7 (t, 1H), 1.7 (s, 12H).

Synthesis Example 12

Synthesis of Compound 57

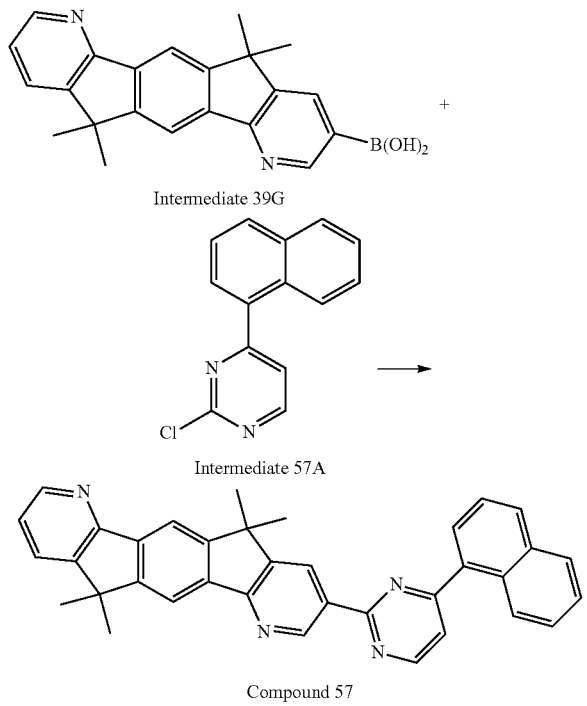

Synthesis of Compound 57

The compound 57 (0.9 g, 67%) was synthesized by using the same method as the synthesis method of the compound 39, except for the usage of the intermediate 57A instead of the intermediate 39H.

H-NMR (CDCl$_3$, 300 MHz, ppm): 9.0-8.8 (m, 3H), 8.4*8.0 (m, 8H), 7.7-7.3 (m, 4H), 6.7 (t, 1H), 1.7 (s, 12H).

Synthesis Example 13

Synthesis of Compound 72

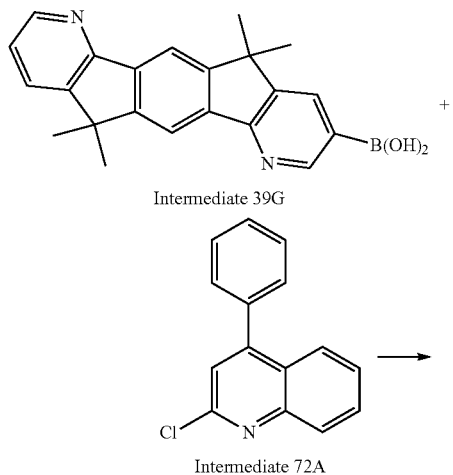

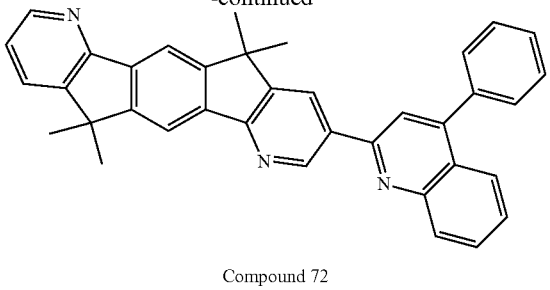

Compound 72

Synthesis of Compound 72

The compound 72 (1.1 g, 72%) was synthesized by using the same method as the synthesis method of the compound 39, except for the usage of the intermediate 72A instead of the intermediate 39H.

H-NMR (CDCl$_3$, 300 MHz, ppm): 9.3 (s, 1H), 8.4-8.3 (m, 3H), 8.1-8.0 (m, 3H), 7.8-7.3 (m, 9H), 6.7 (t, 1H), 1.7 (s, 12H).

EXEMPLARY EMBODIMENTS

Exemplary Embodiment 1

A 15 Ω/cm$^2$ 500 Å ITO glass substrate (manufactured by Corning) was incised to the size of 50 mm×50 mm×0.5 mm, an ultrasonic wave cleaning process was performed for ten minutes by using isopropyl alcohol and pure water, ultraviolet rays were irradiated thereto for ten minutes. Then, the substrate was exposed to ozone to be cleaned, and was installed in a vacuum deposition device. Then, 2-TNATA (4,4',4''-tris(N-(2-naphthyl)-N-phenyl-amino)-triphenylamine) was vacuum-deposited on an upper portion of the ITO glass substrate to form a 600 Å thick hole injection layer, and NPB (4,4'-bis(naphthalene-1-yl)-N—N'-bis(phenyl)-benzidine) was vacuum-deposited with a 300 Å thickness with a hole transporting compound to form a hole transport layer.

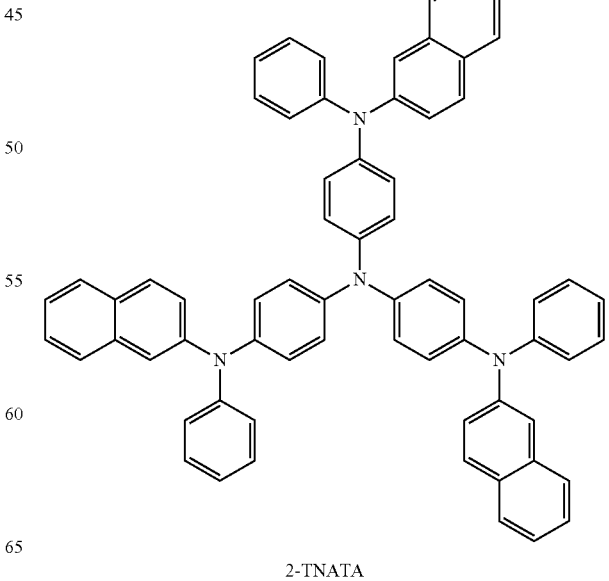

2-TNATA

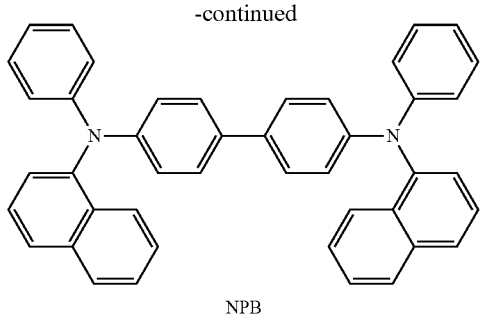

NPB

Sequentially, ADN (9,10-di(naphth-2-yl)anthracene) and DNTPD (N1,N1'-(biphenyl-4,4'-diyl)bis(N1-phenyl-N4,N4-di-m-tolylbenzene-1,4-diamine) as a blue fluorescent host were simultaneously deposited with a weight ratio 96:4 at an upper portion of the hole transport layer, such that a 300 Å thick emission layer was formed. Compound 1 was deposited to be 300 Å thick, forming an electron transport layer, and Al was vacuum-deposited to be 1,200 Å (cathode electrode) thick, forming an Al electrode, such that an organic light emitting diode device was manufactured.

Exemplary Embodiment 2

1

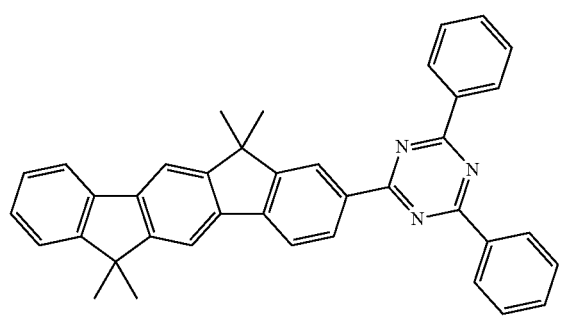

The organic light emitting diode device was manufactured in a like manner as exemplary embodiment 1, except for formation of the electron transport layer by use of compound 4 instead of compound 1.

Exemplary Embodiment 3

4

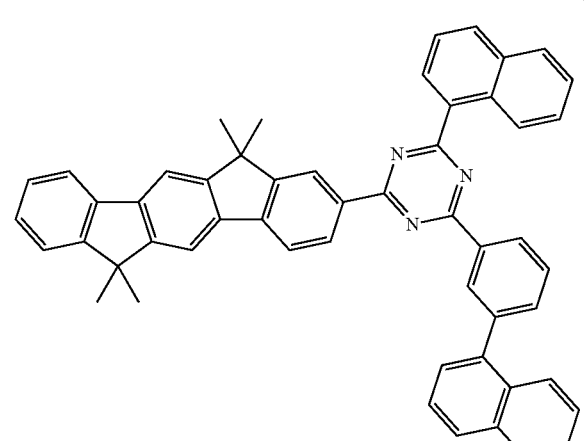

The organic light emitting diode device was manufactured in a like manner as exemplary embodiment 1, except for formation of the electron transport layer by use of compound 7 instead of compound 1.

Exemplary Embodiment 4

7

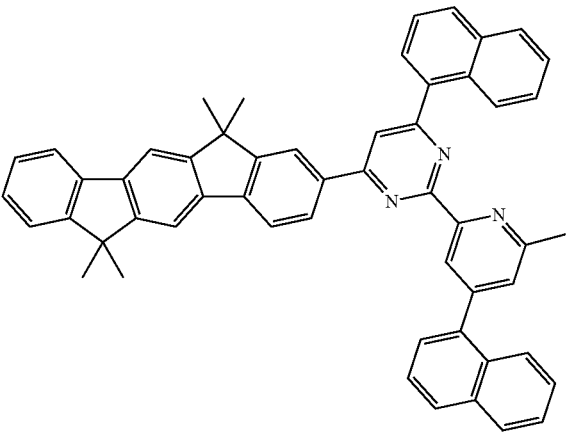

The organic light emitting diode device was manufactured in a like manner as exemplary embodiment 1, except for formation of the electron transport layer by use of compound 11 instead of compound 1.

Exemplary Embodiment 5

11

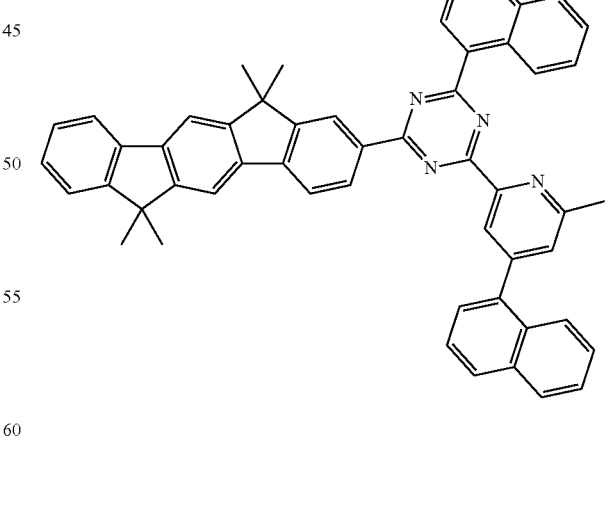

The organic light emitting diode device was manufactured in a like manner as exemplary embodiment 1, except for formation of the electron transport layer by use of compound 17 instead of compound 1.

Exemplary Embodiment 6

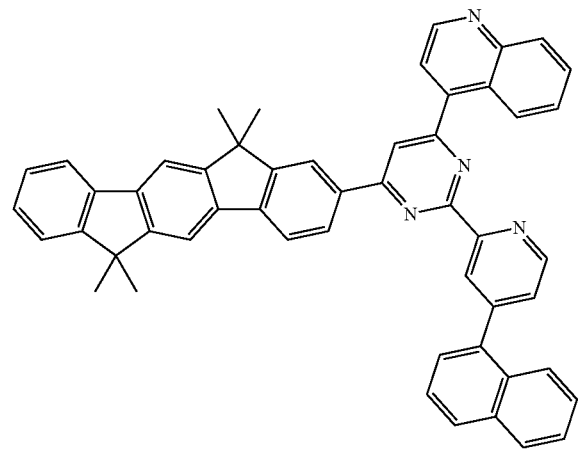

17

The organic light emitting diode device was manufactured in a like manner as the exemplary embodiment 1, except for formation of the electron transport layer by use of compound 22 instead of compound 1.

Exemplary Embodiment 7

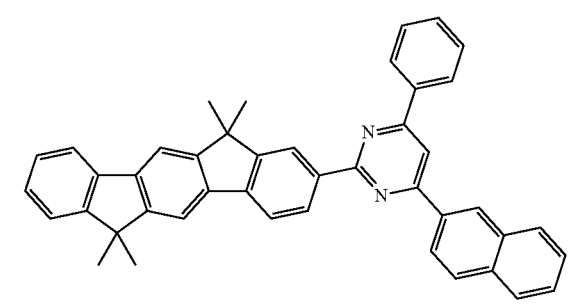

22

The organic light emitting diode device was manufactured in a like manner as exemplary embodiment 1, except for formation of the electron transport layer by use of compound 28 instead of compound 1.

Exemplary Embodiment 8

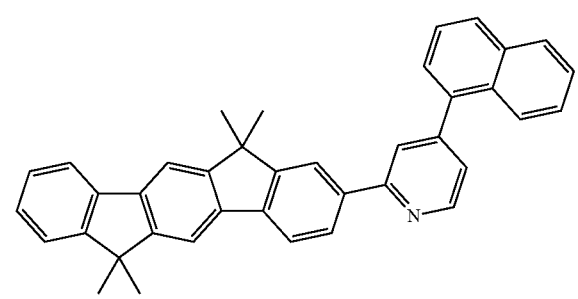

28

The organic light emitting diode device was manufactured in a like manner as exemplary embodiment 1, except for formation of the electron transport layer by use of compound 39 instead of compound 1.

Exemplary Embodiment 9

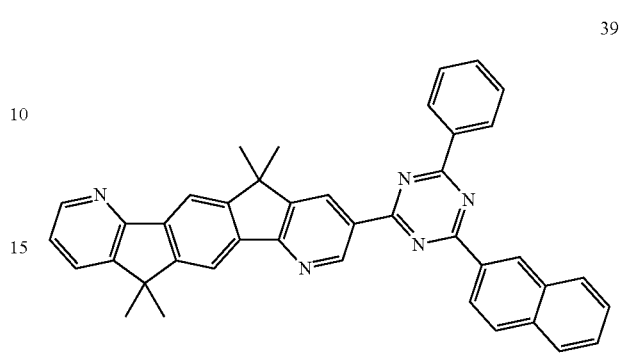

39

The organic light emitting diode device was manufactured in a like manner as exemplary embodiment 1, except for formation of the electron transport layer by use of compound 43 instead of compound 1.

Exemplary Embodiment 10

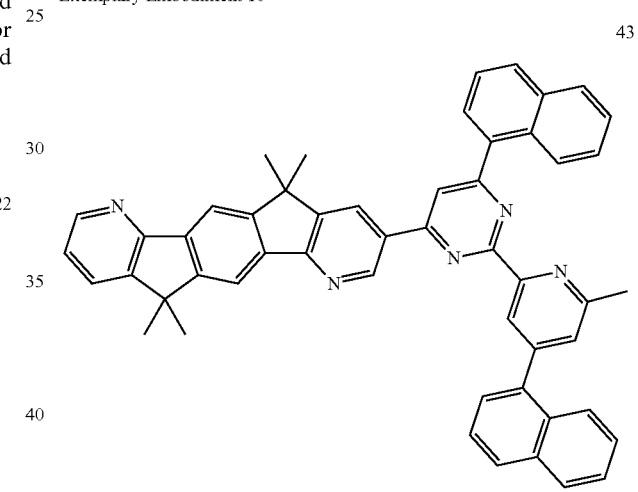

43

The organic light emitting diode device was manufactured in a like manner as exemplary embodiment 1, except for formation of the electron transport layer by use of compound 47 instead of compound 1.

Exemplary Embodiment 11

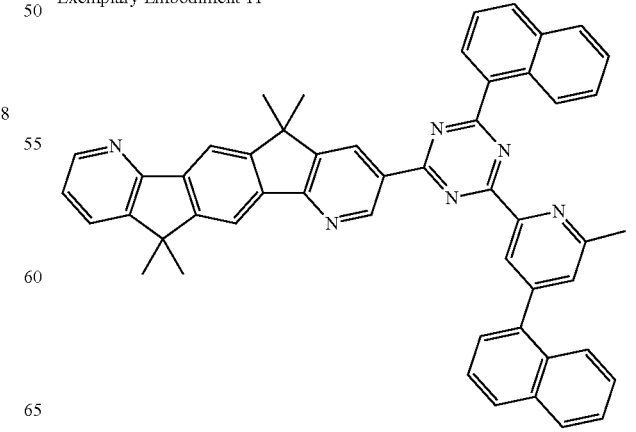

47

The organic light emitting diode device was manufactured in a like manner as exemplary embodiment 1, except for formation of the electron transport layer by use of compound 51 instead of compound 1.

Exemplary Embodiment 12

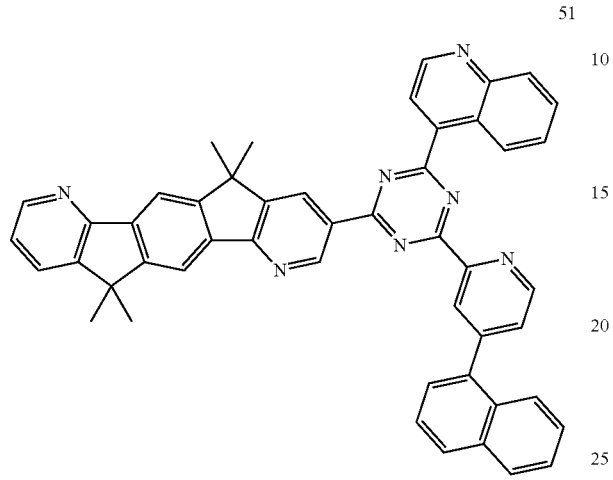

51

The organic light emitting diode device was manufactured in a like manner as exemplary embodiment 1, except for formation of the electron transport layer by use of compound 57 instead of compound 1.

Exemplary Embodiment 13

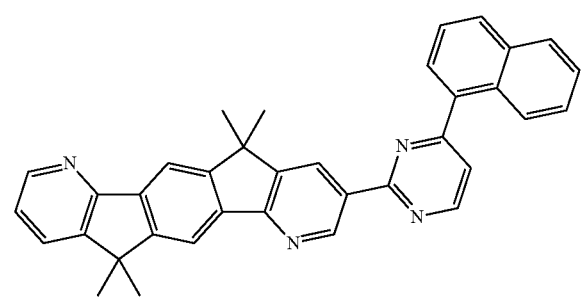

57

The organic light emitting diode device was manufactured in a like manner as exemplary embodiment 1, except for formation of the electron transport layer by use of compound 72 instead of compound 1.

Comparative Example 1

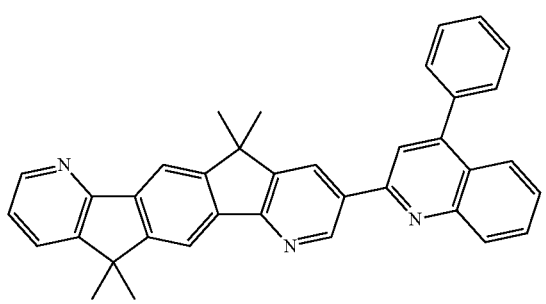

72

An organic light emitting element was manufactured in a like manner as exemplary embodiment 1, except for usage of Alq3(tris(8-hydroxy-quinolinato)aluminum) instead of compound 1 when the electron transport layer is formed.

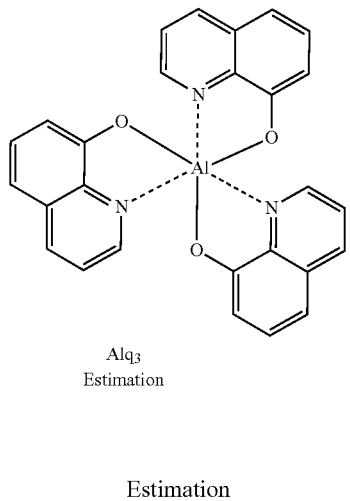

Alq3

Estimation

Estimation

Characteristics of the organic light emitting diode device according to the exemplary embodiments 1 to 18 and the comparative example 1 were estimated.

The results are expressed in Table 1.

TABLE 1

| | Electron Transport Layer | Voltage (V) | Efficiency (cd/A) | T90 (hr) |
|---|---|---|---|---|
| Exemplary Embodiment 1 | Compound 1 | 6.0 | 6.1 | 356 |
| Exemplary Embodiment 2 | Compound 4 | 5.4 | 5.9 | 268 |
| Exemplary Embodiment 3 | Compound 7 | 5.3 | 5.4 | 394 |
| Exemplary Embodiment 4 | Compound 11 | 5.1 | 6.3 | 316 |
| Exemplary Embodiment 5 | Compound 17 | 5.6 | 5.1 | 267 |
| Exemplary Embodiment 6 | Compound 22 | 4.8 | 6.1 | 316 |
| Exemplary Embodiment 7 | Compound 28 | 4.7 | 8.4 | 282 |
| Exemplary Embodiment 8 | Compound 39 | 5.3 | 5.2 | 315 |
| Exemplary Embodiment 9 | Compound 43 | 5.36 | 6.7 | 326 |
| Exemplary Embodiment 10 | Compound 47 | 5.9 | 5.4 | 293 |
| Exemplary Embodiment 11 | Compound 51 | 5.4 | 5.2 | 264 |
| Exemplary Embodiment 12 | Compound 57 | 5.3 | 4.9 | 342 |
| Exemplary Embodiment 13 | Compound 72 | 4.7 | 7.1 | 316 |
| Comparative Example 1 | Alq3 | 6.4 | 4.8 | 243 |

Referring to Table 1, when the compounds having the structures of exemplary embodiment 1 to exemplary embodiment 13 are used as an electron transport layer in the organic light emitting diode device, the driving voltage is reduced compared to Alq3, and an excellent I-V-L characteristic with improved efficiency is provided. Particularly, the exemplary embodiments 6, 7, 17, 18, and 19 reduce the driving voltage by more than 1.5 V, and the exemplary embodiments 7 and 13 provide about a 50% efficiency improvement.

By way of summation and review, embodiments provide a compound that provides an organic material with excellent optical and electrical performance. An organic electroluminescence device with a low driving voltage and improved light emission efficiency and lifespan may be manufactured by using the same.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope thereof as set forth in the following claims.

What is claimed is:

1. An organic compound represented by Formula 1:

[Formula 1]

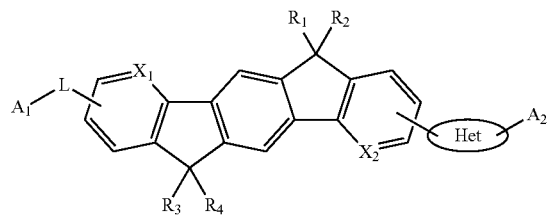

wherein the compound represented by Formula 1 includes at least one of the following Compounds 2 to 72:

2

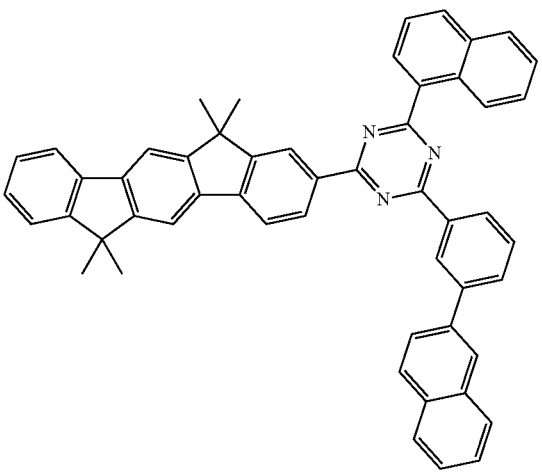

3

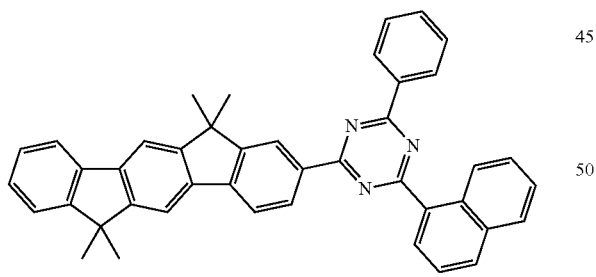

4

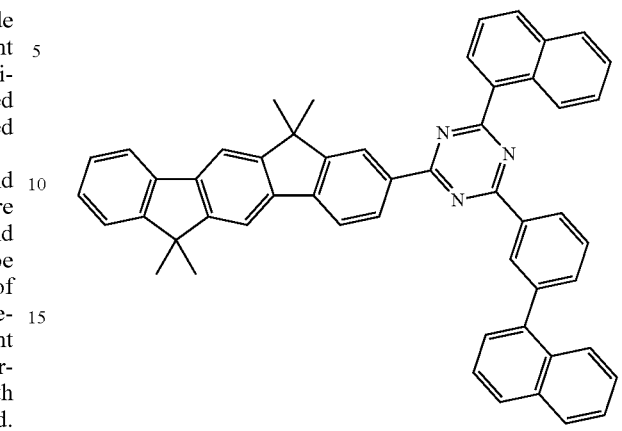

5

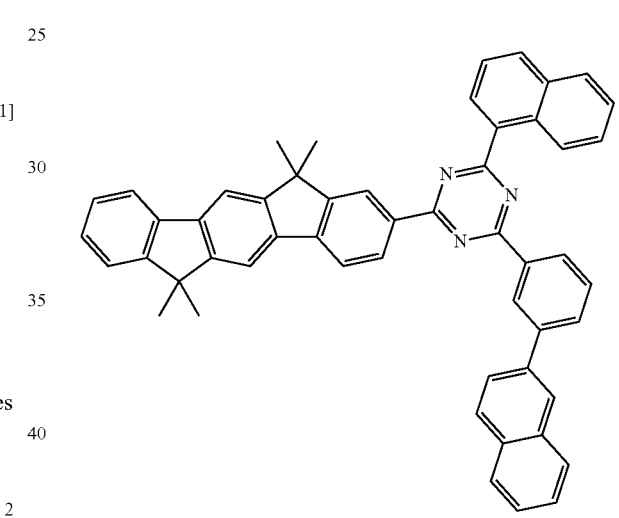

6

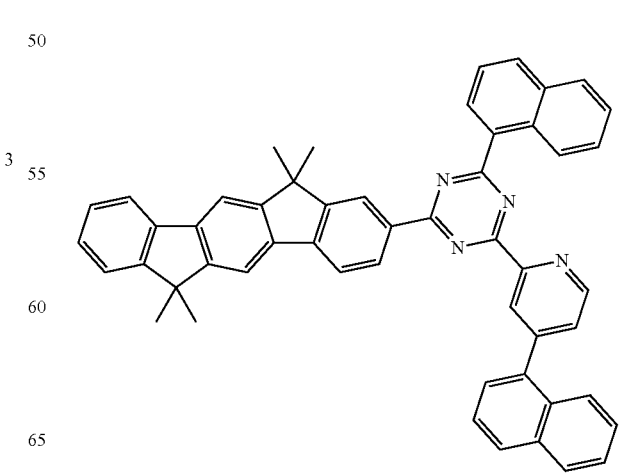

7
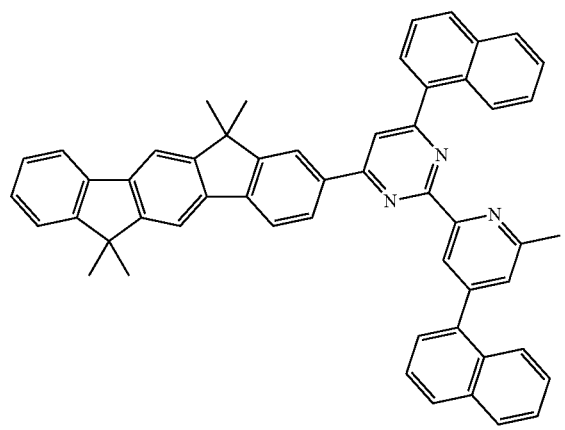
8
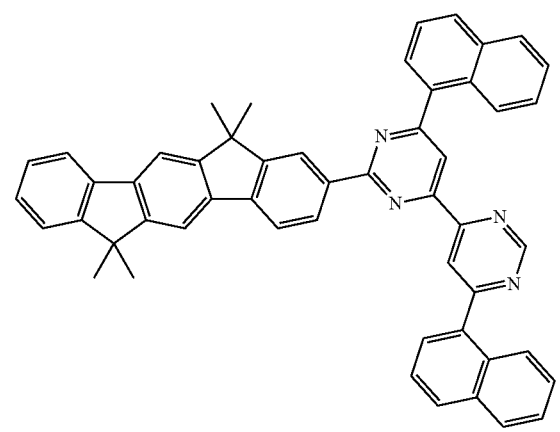
9
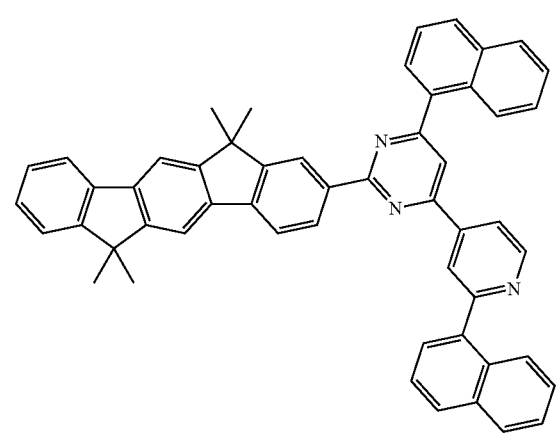
10
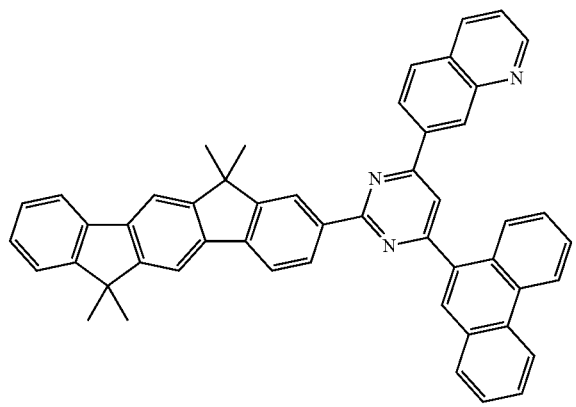
11
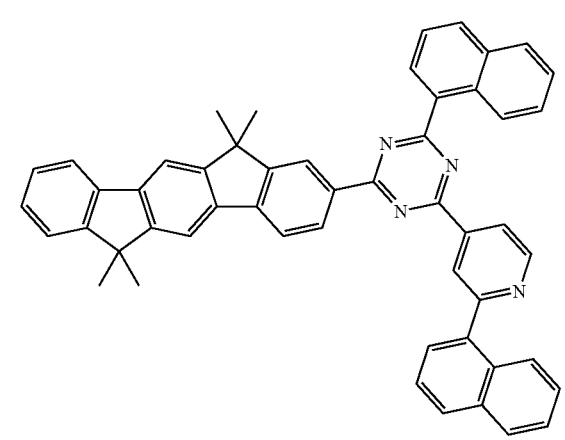
12

13
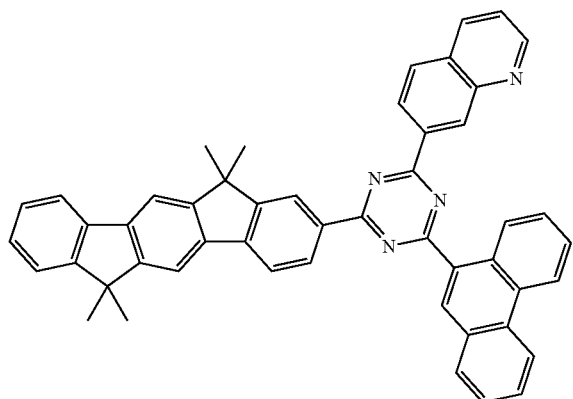
14
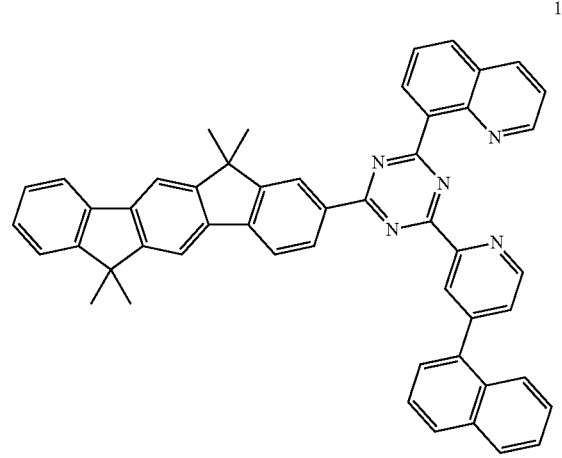
15
16
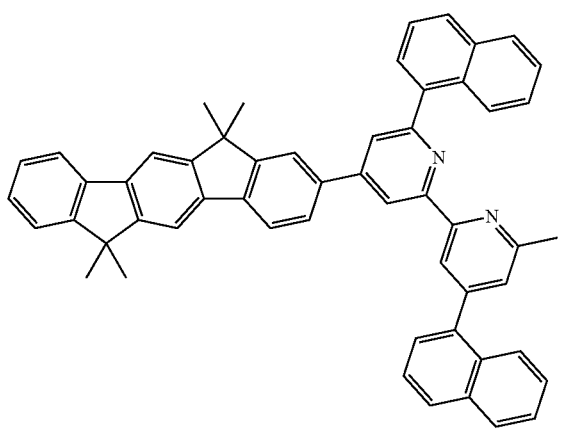
17
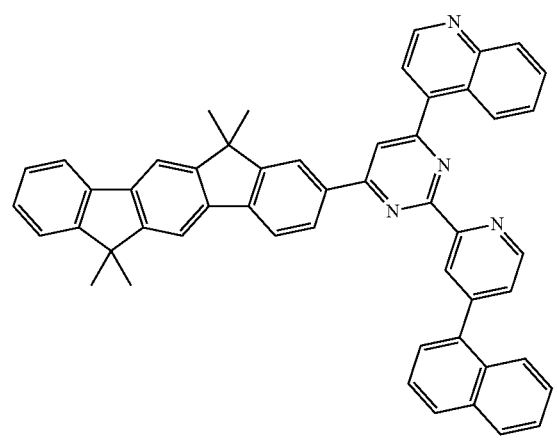
18
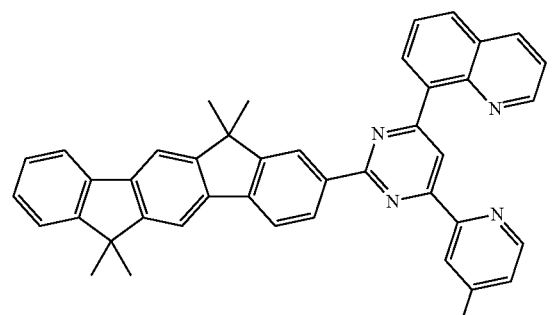
19
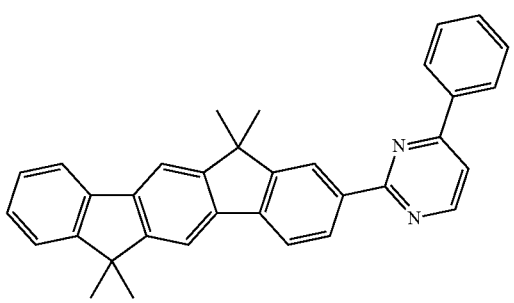

20
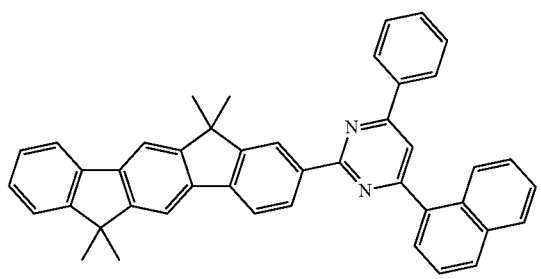
21
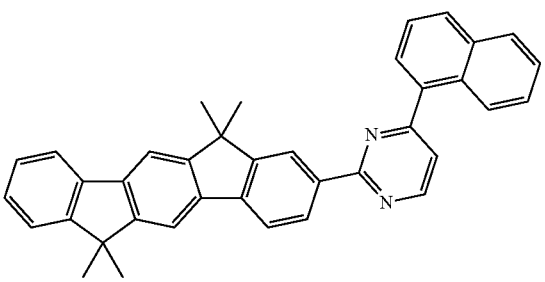
22
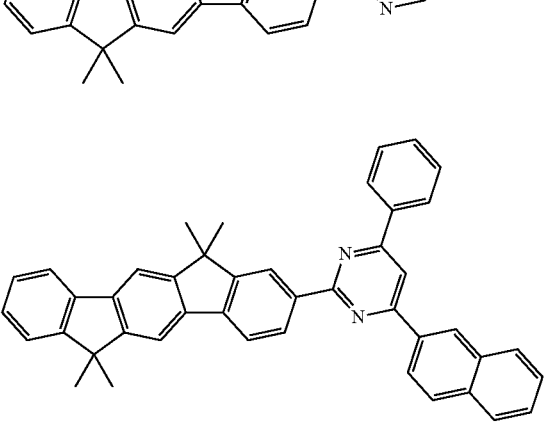
23
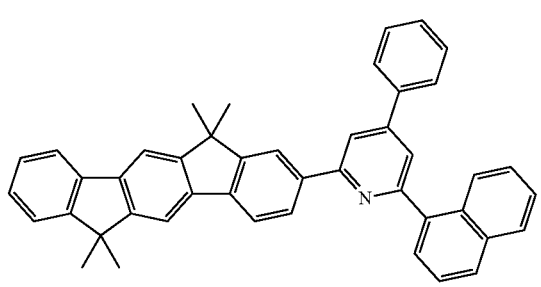
24
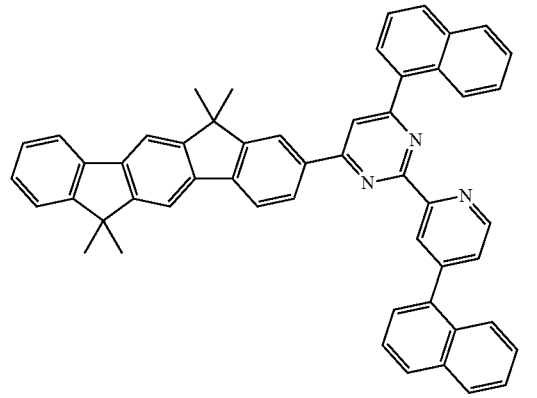
25
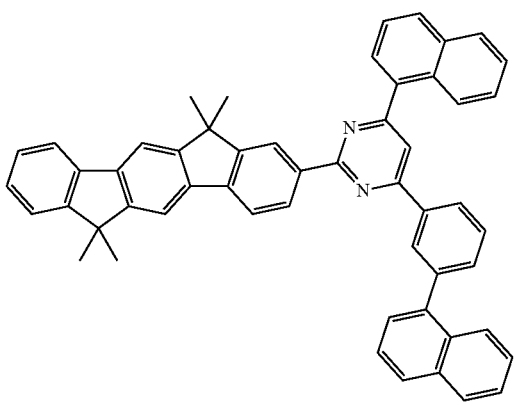
26
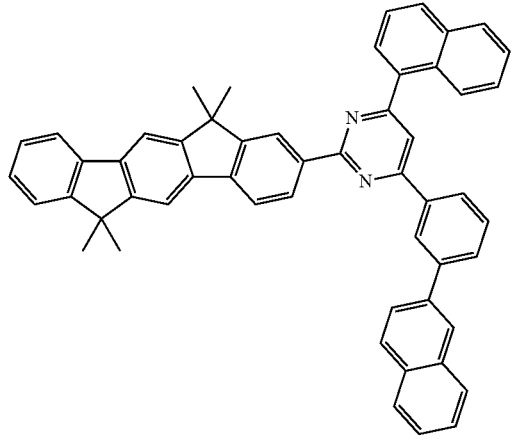
27
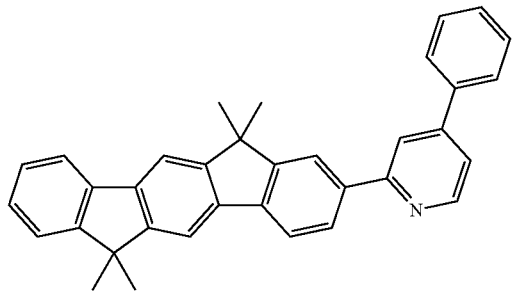
28
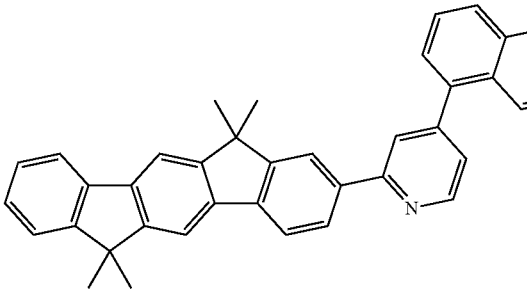

29
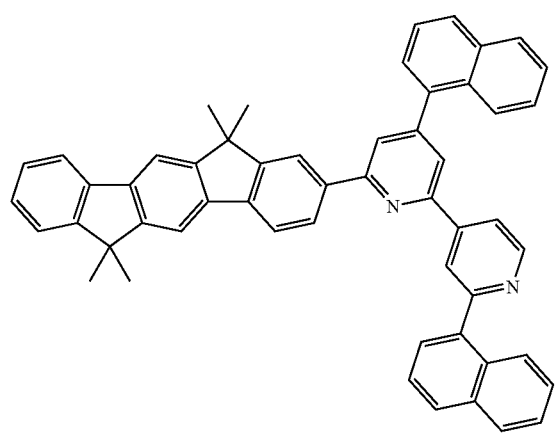
30
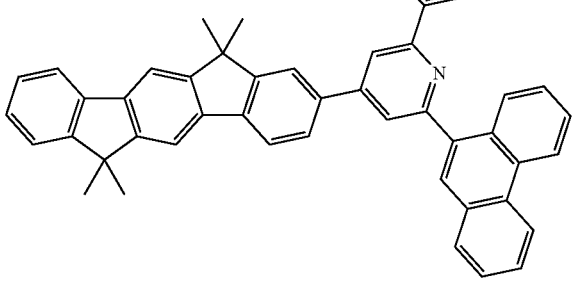
31
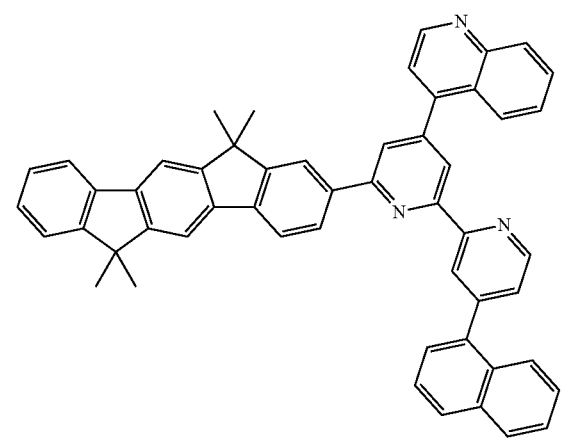
32
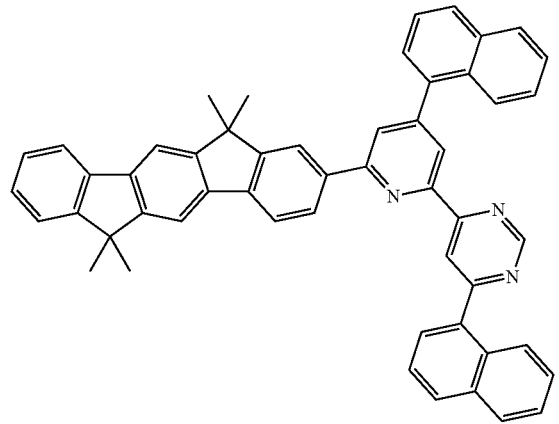
33
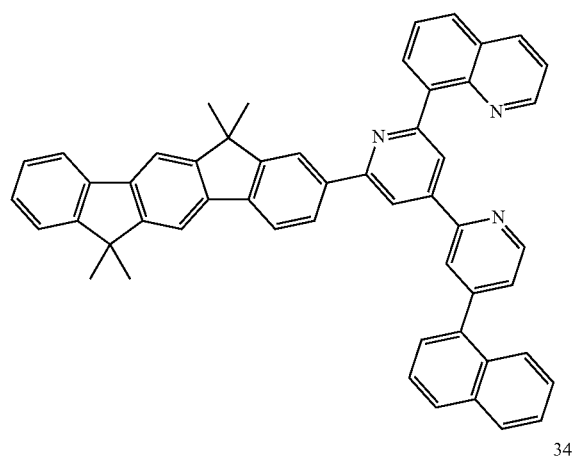
34
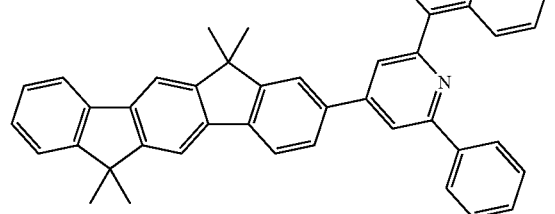
35
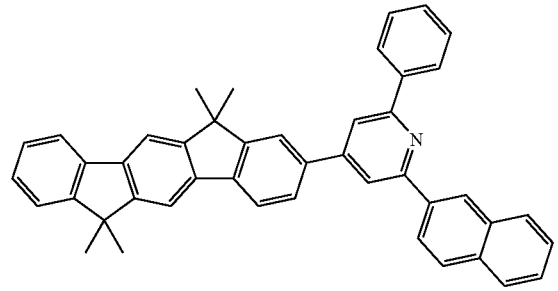

36
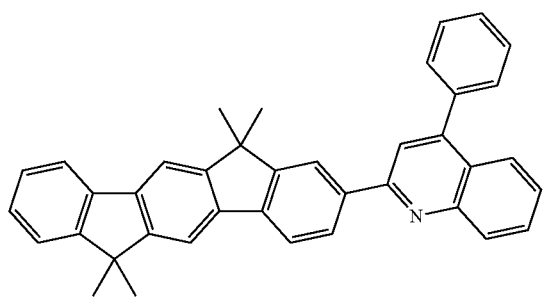
37
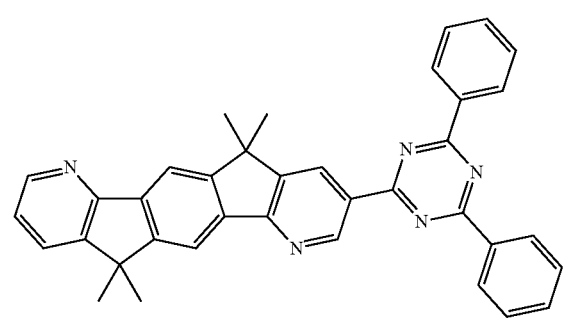
38
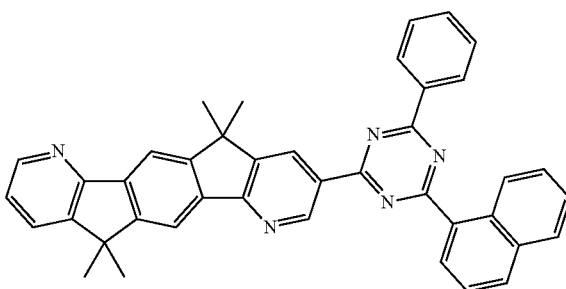
39
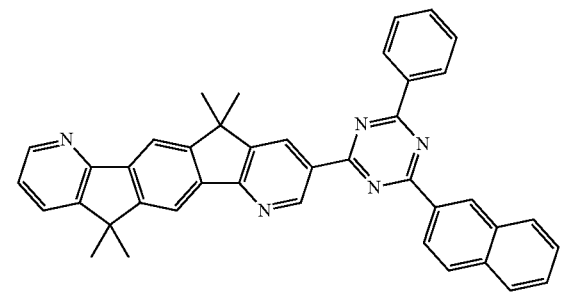
40
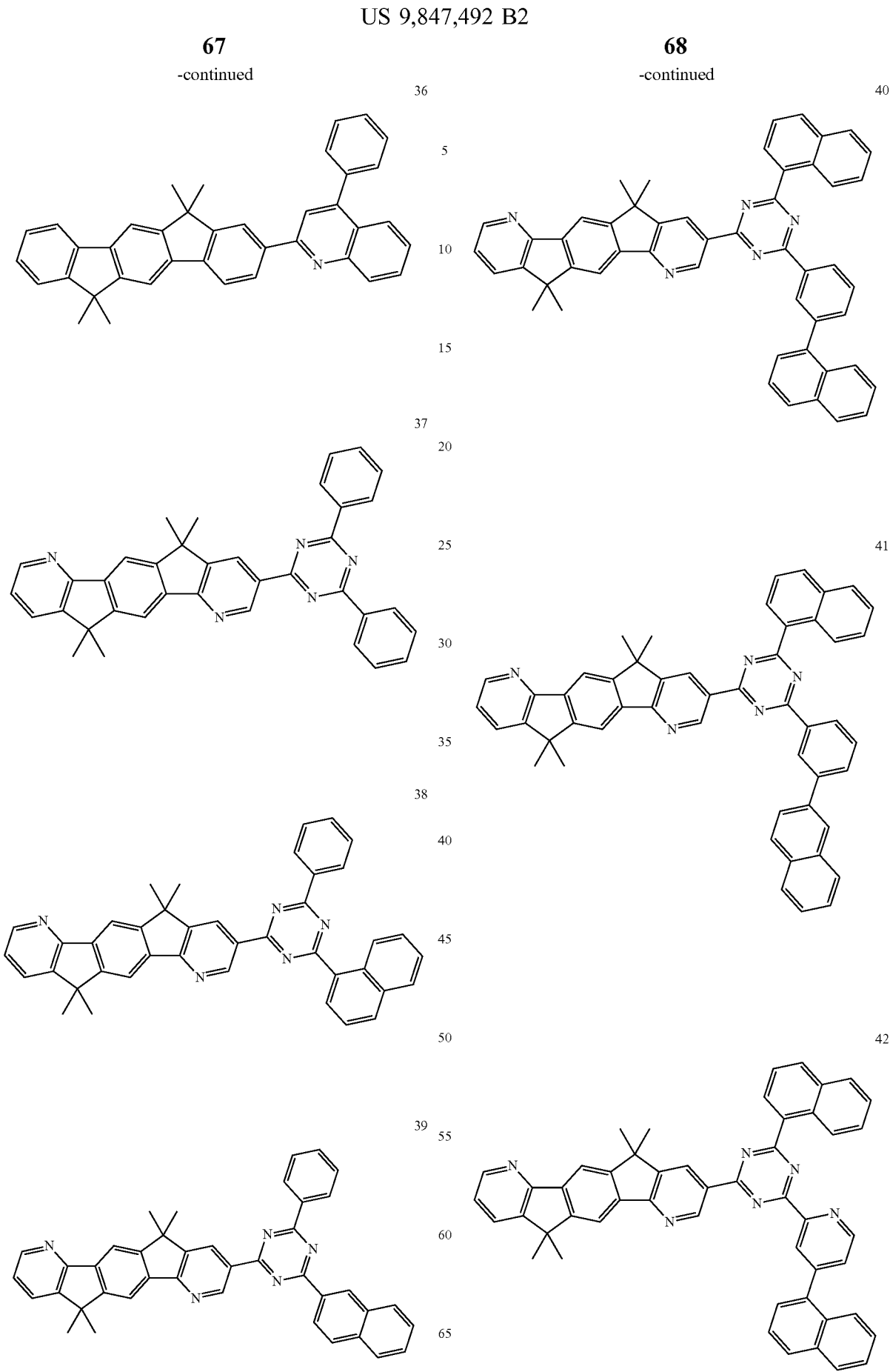

43
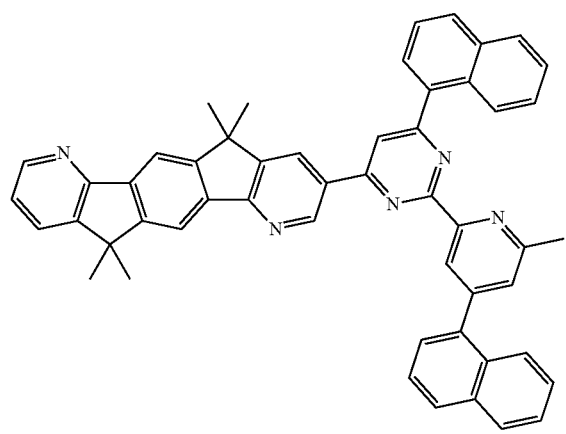
44
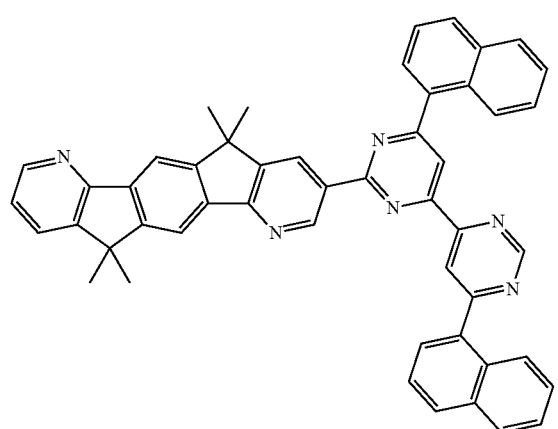
45
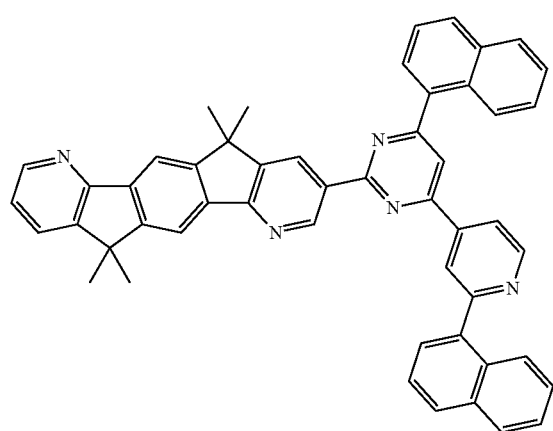
46
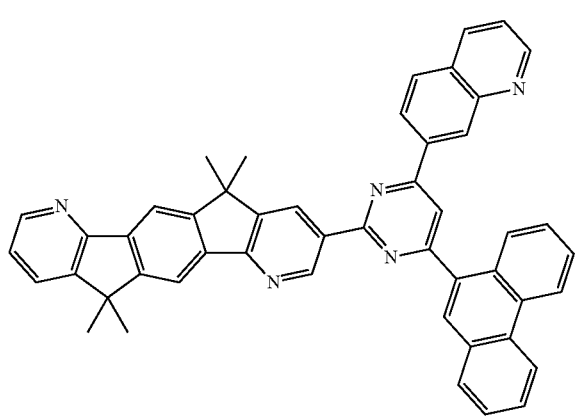
47
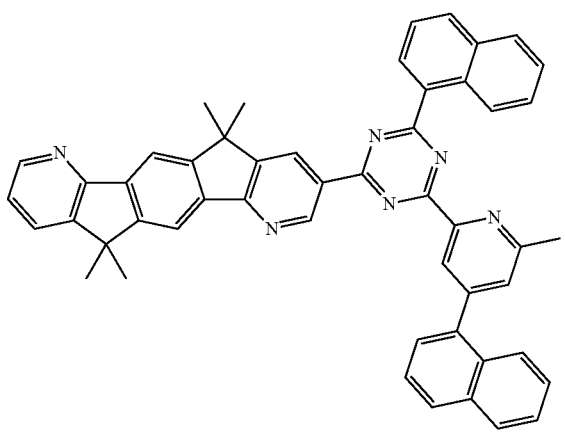
48
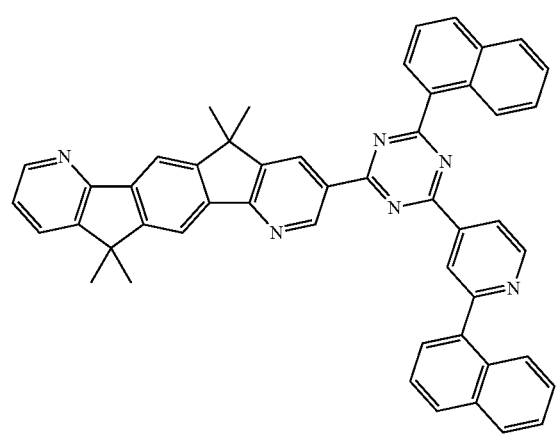

49
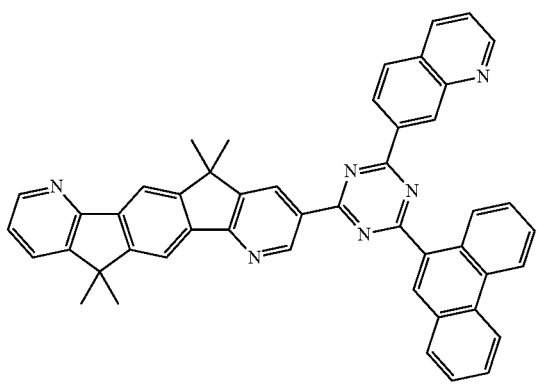
50
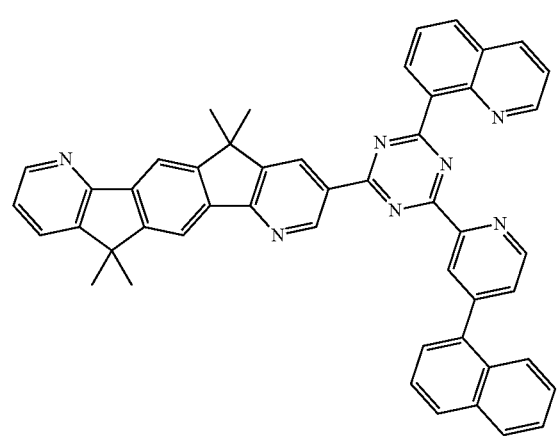
51
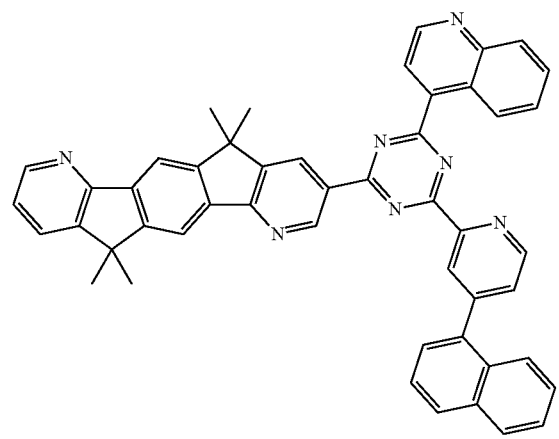
52
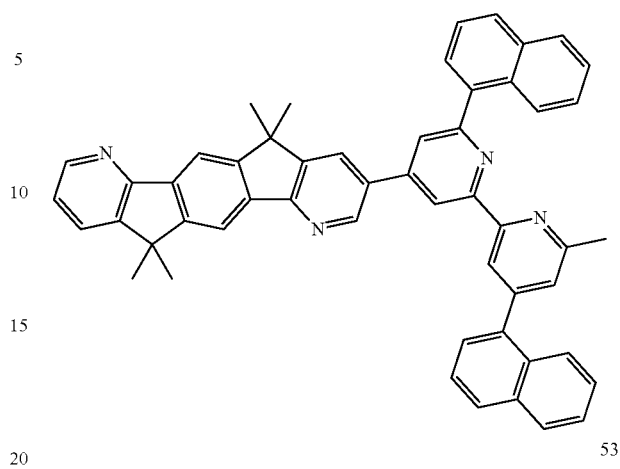
53
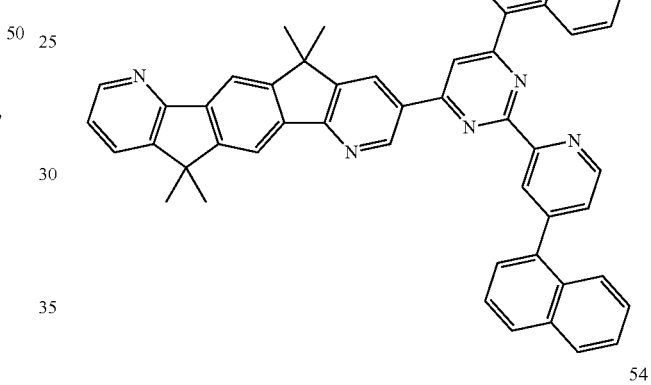
54
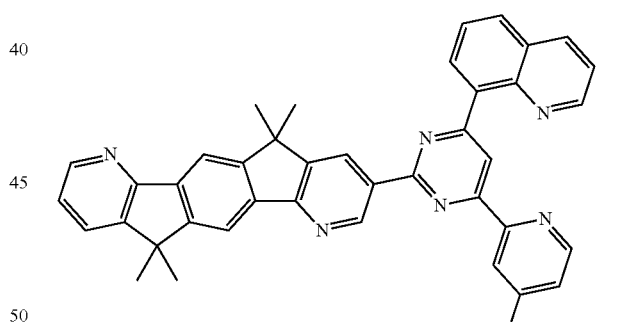
55
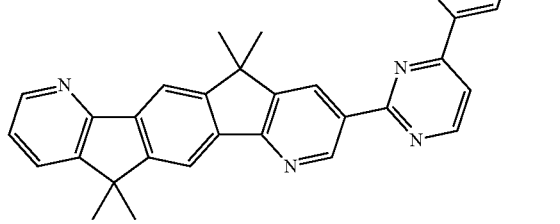

-continued
56
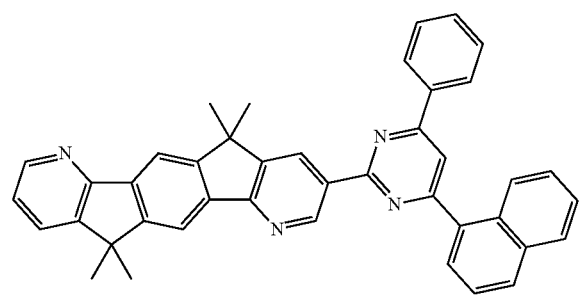
57
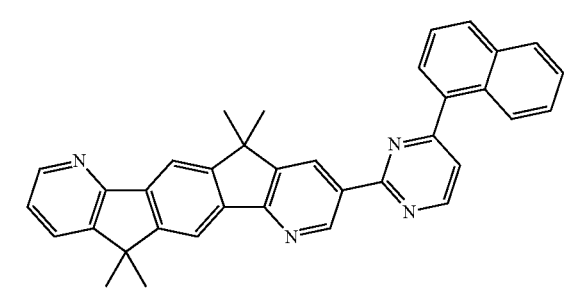
58
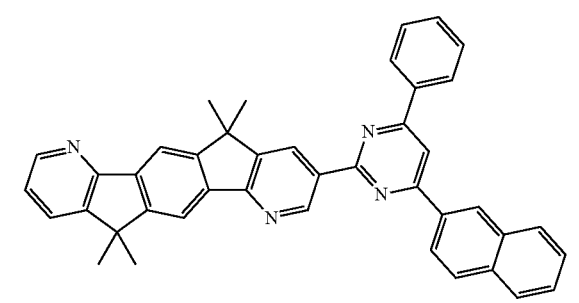
59
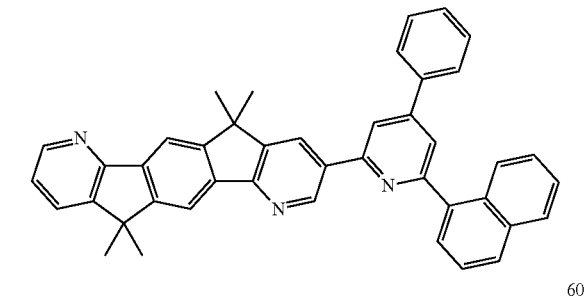
60
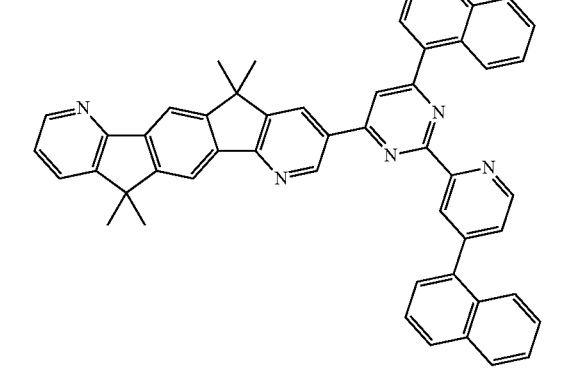
-continued
61
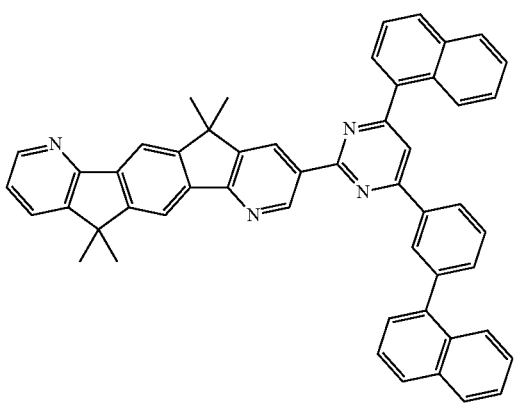
62
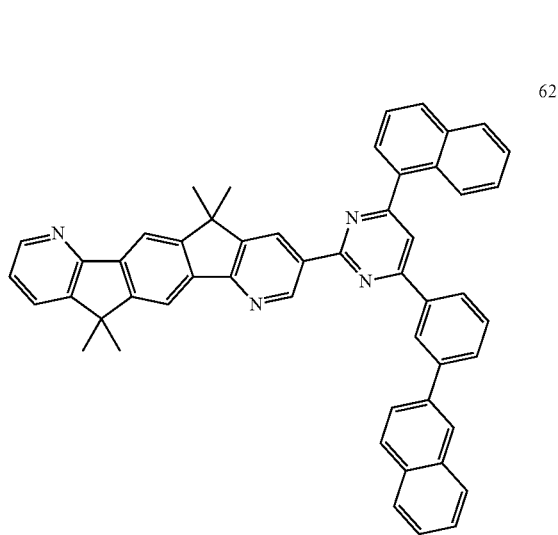
63
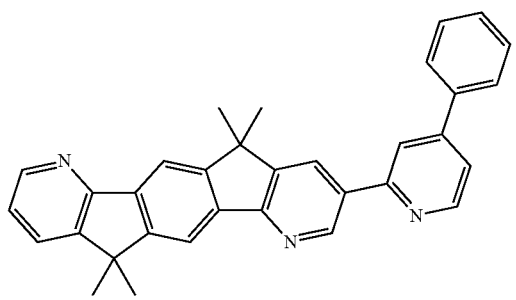
64
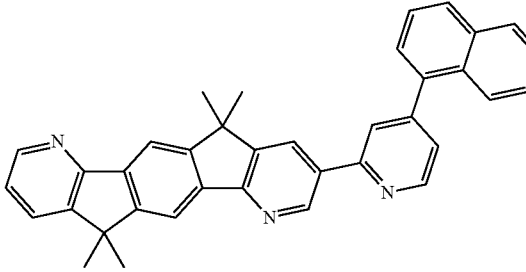

65
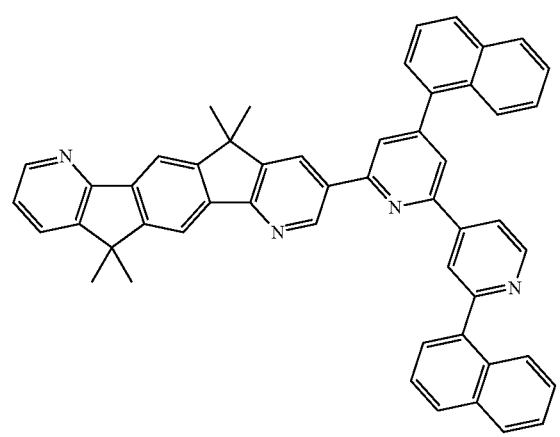
66
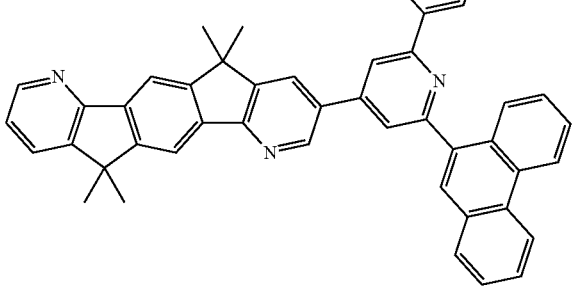
67
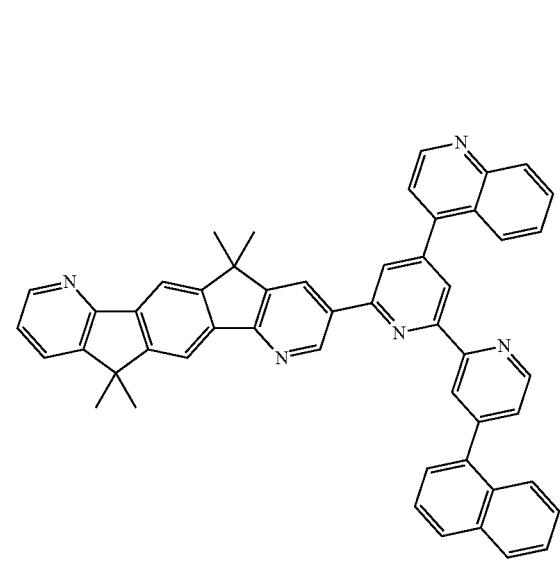
68
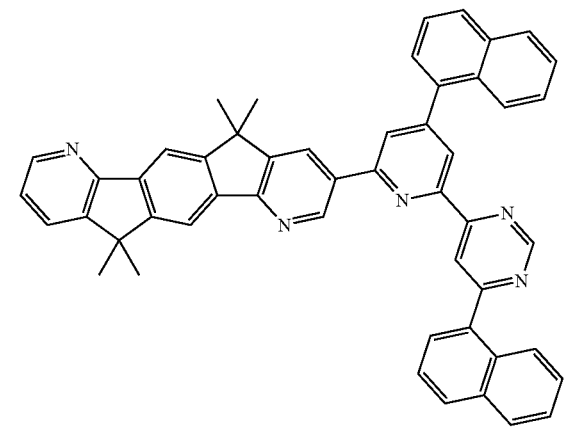
69
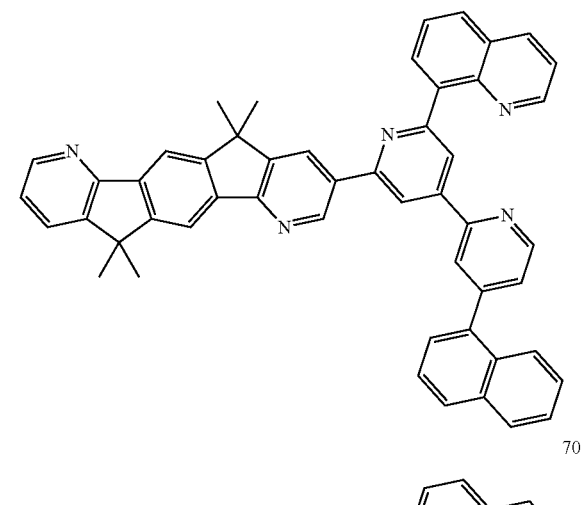
70
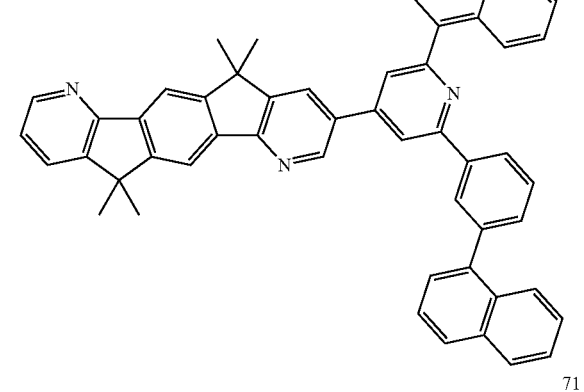
71

72

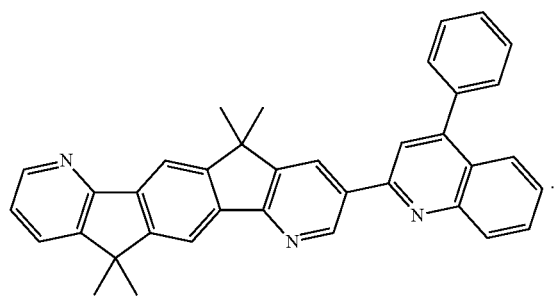

2. An organic light emitting diode device, comprising: an anode; a cathode; and an organic layer between the anode and the cathode; the organic layer includes an electron transport layer, and the organic compound is included in the electron transport layer; wherein the organic compound is represented by Formula 1:

[Formula 1]

wherein the compound represented by Formula 1 includes at least one of the following Compounds 2 to 72:

2

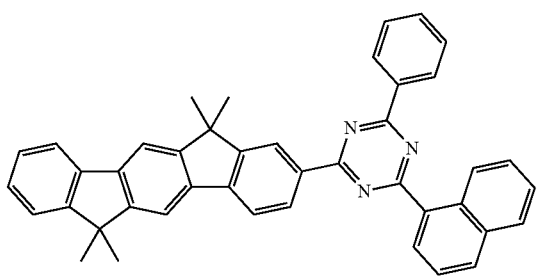

3

4

5

6

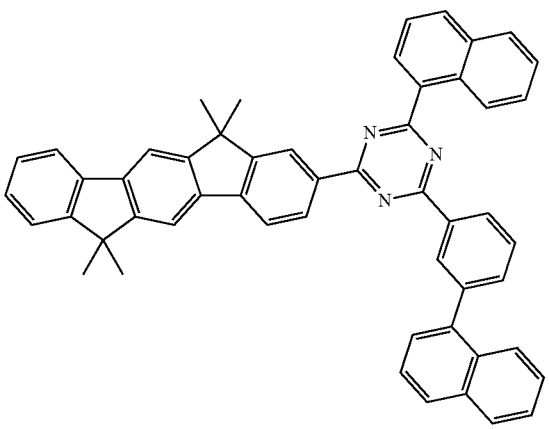

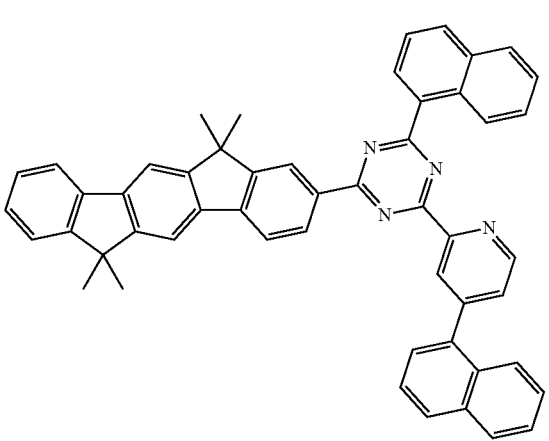

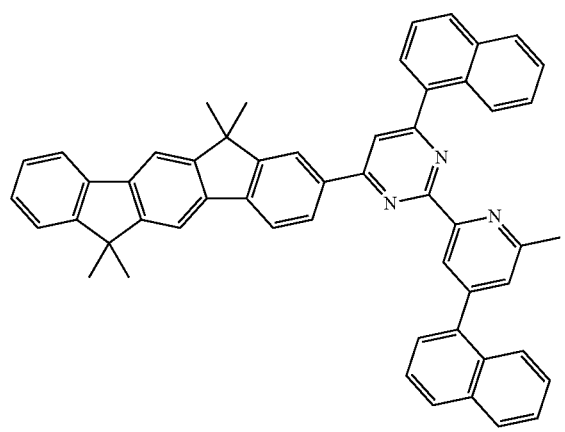
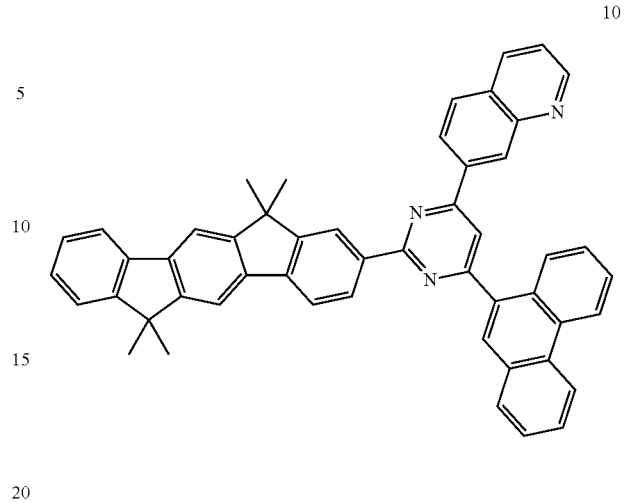
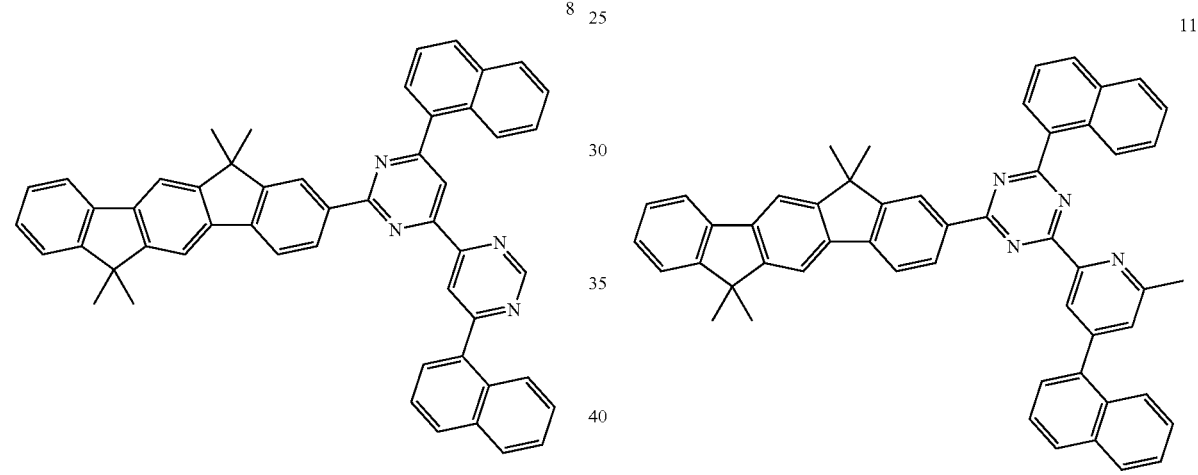
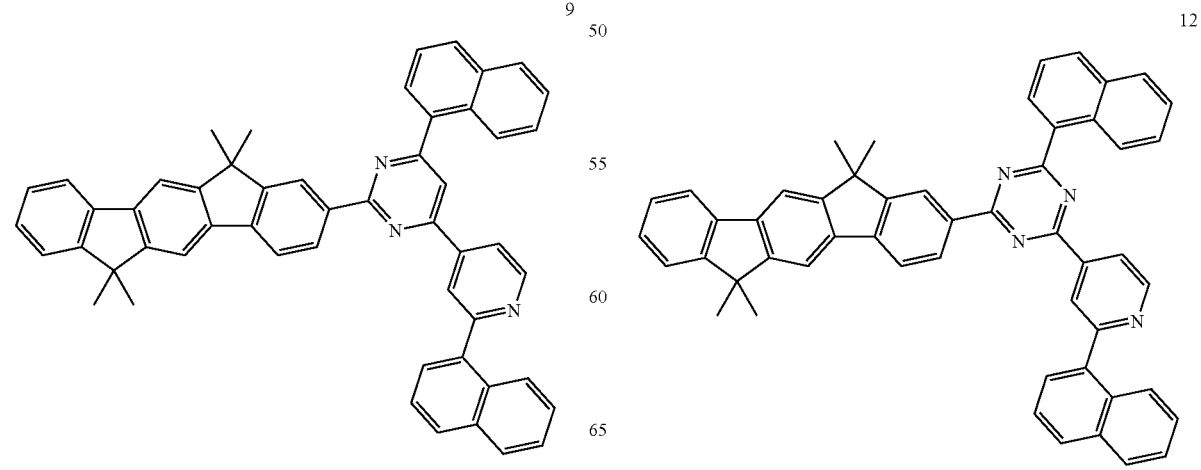

13
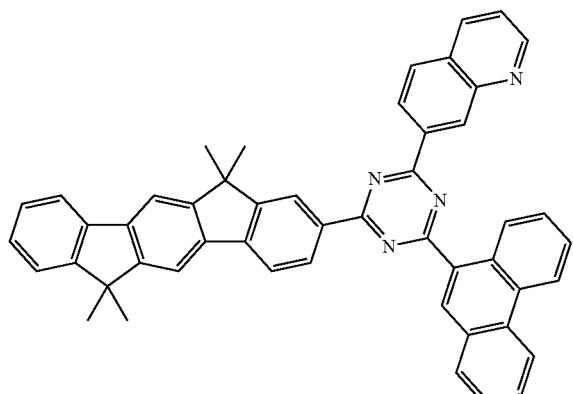
14
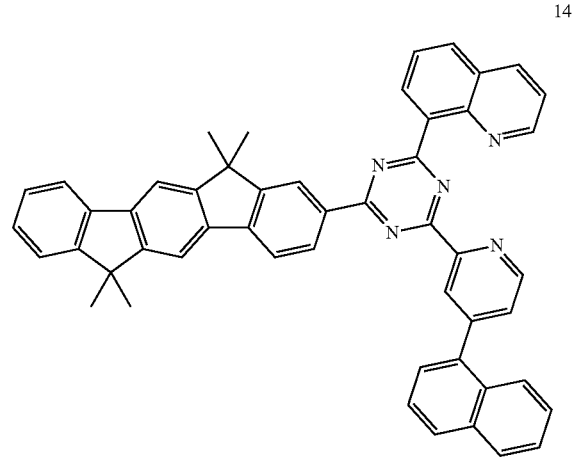
15
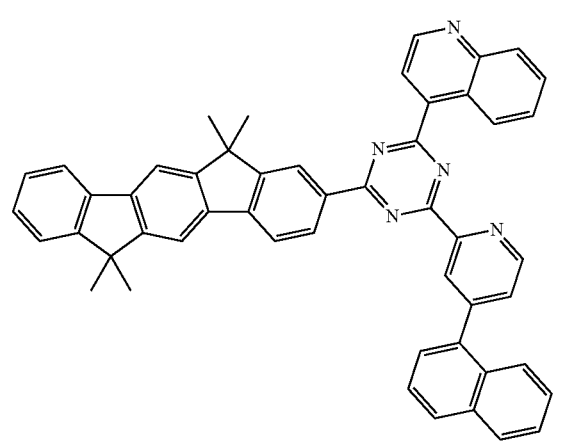
16
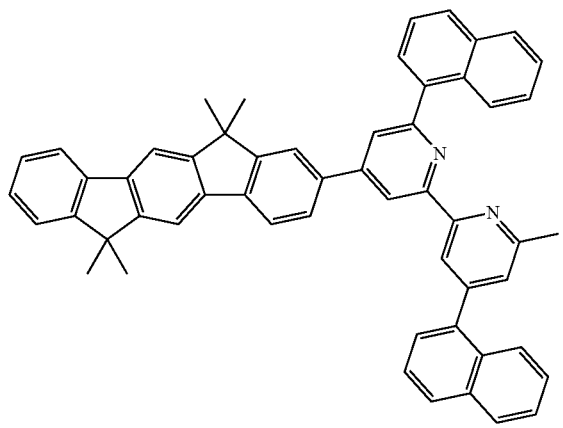
17
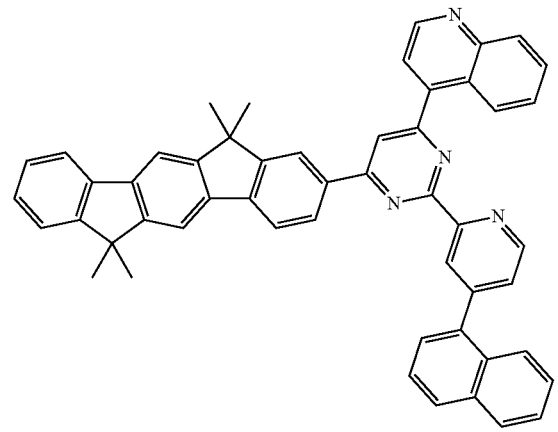
18

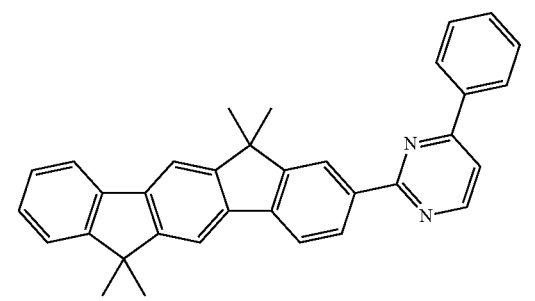
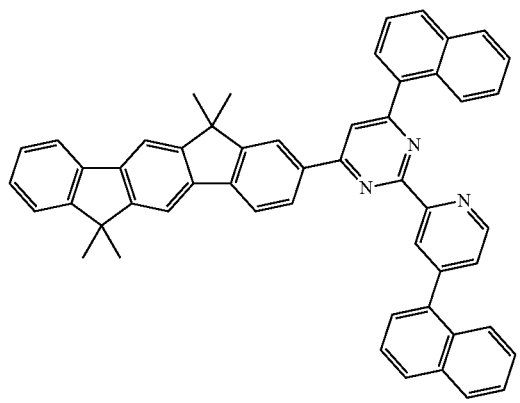

28 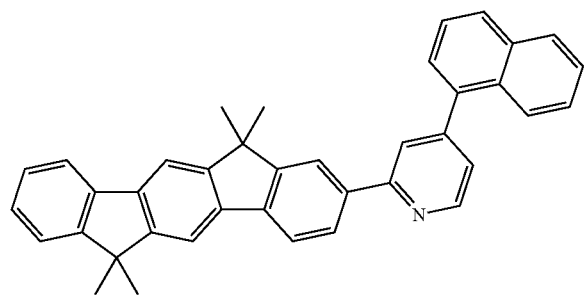
29 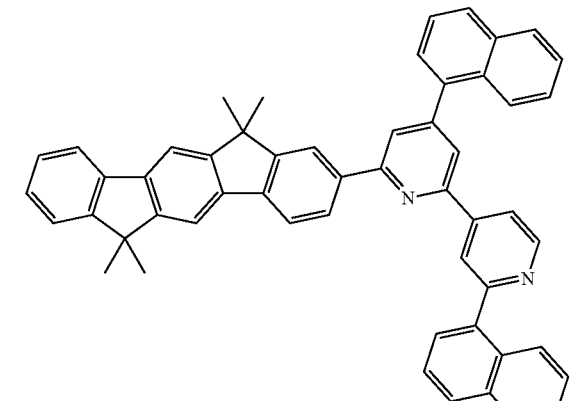
30 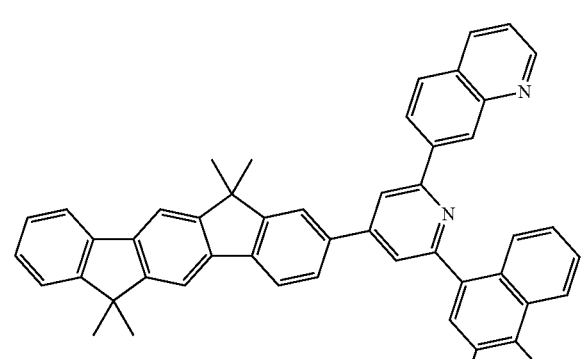
31 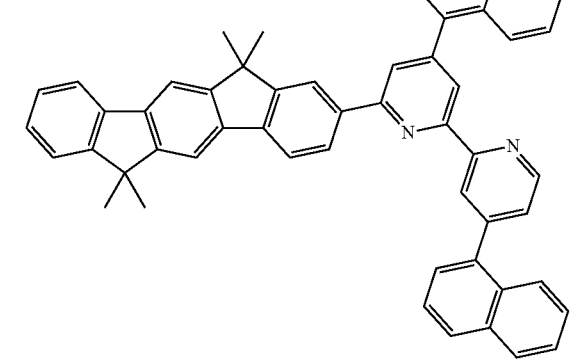
32 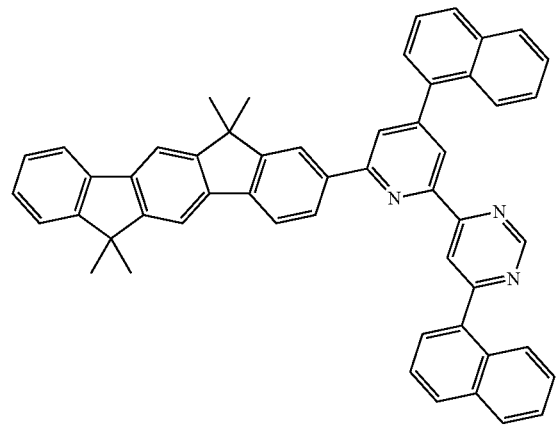
33 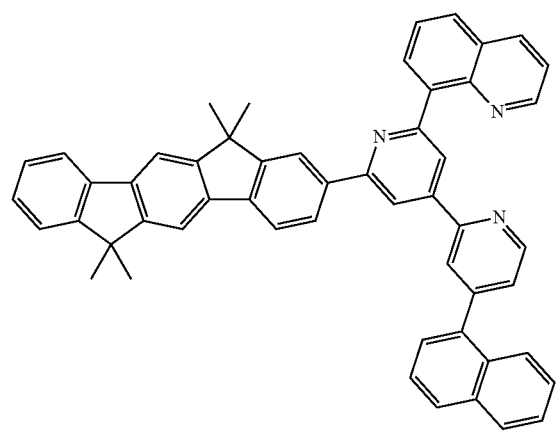
34 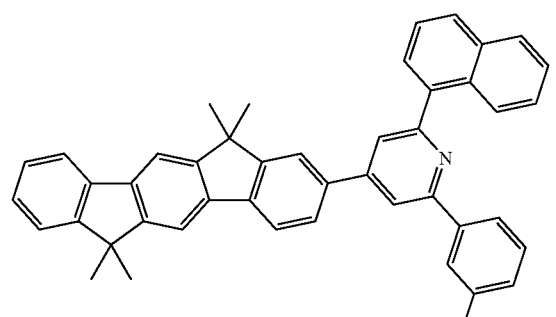
35 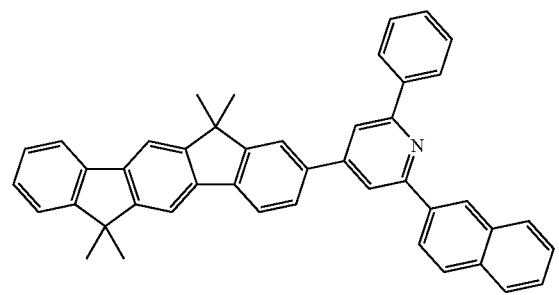

36
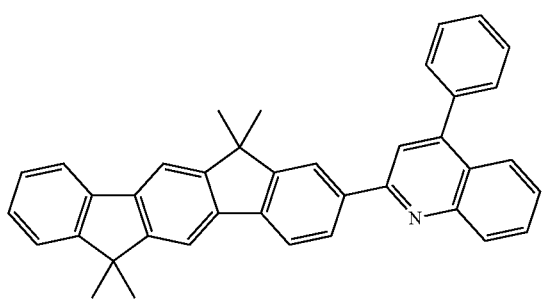
37
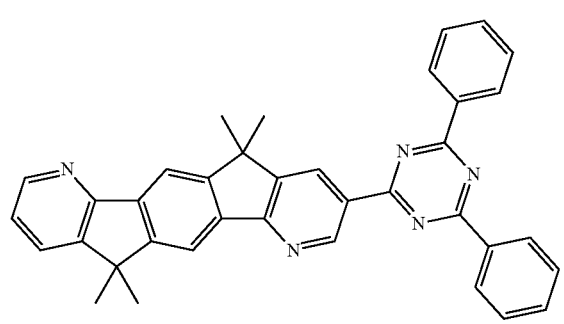
38
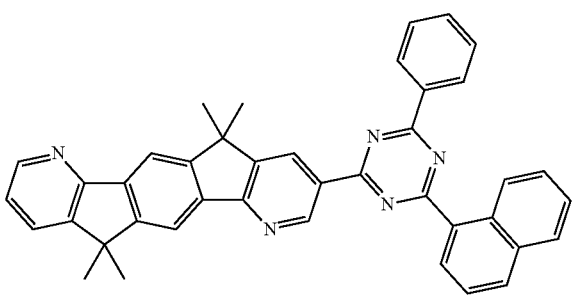
39
40
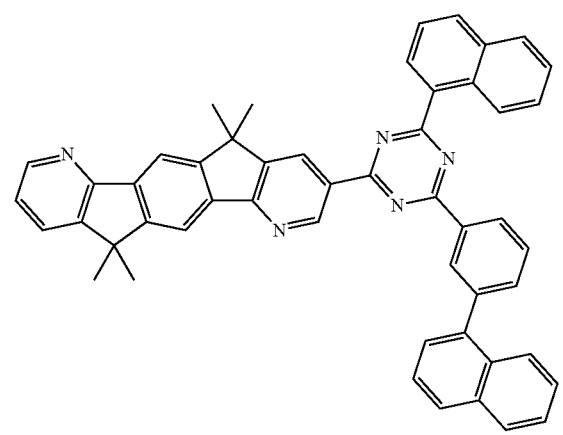
41
42
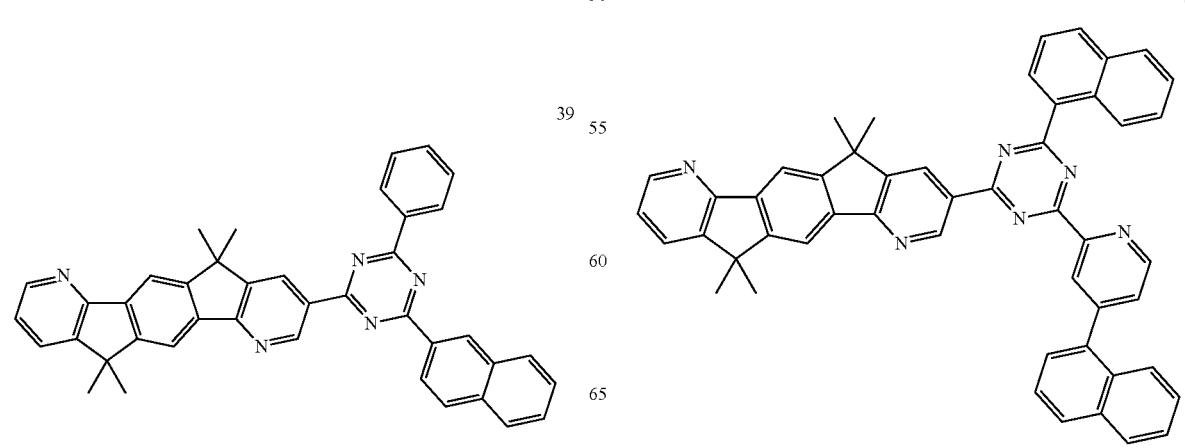

43
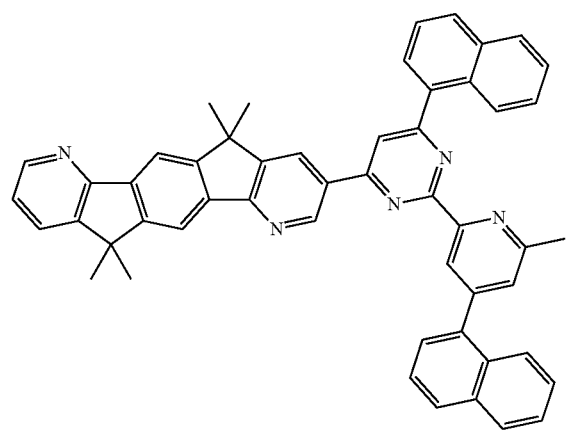
46
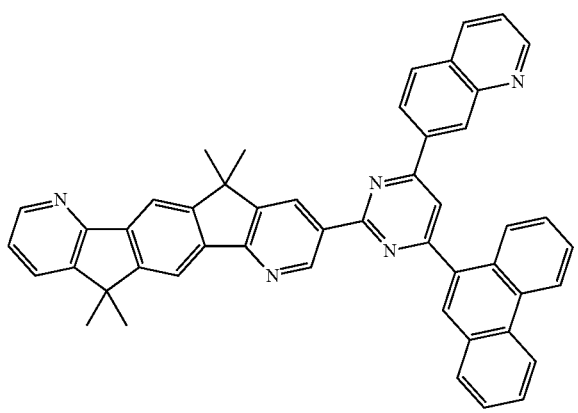
44
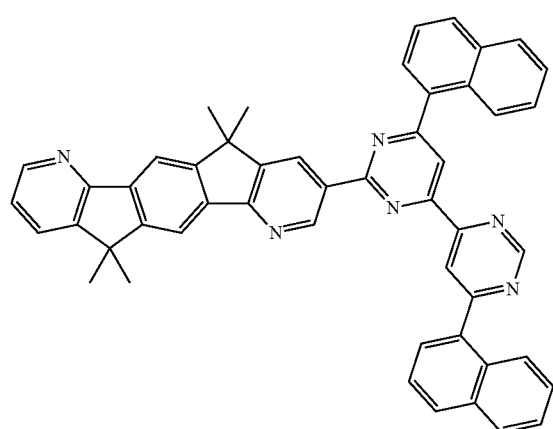
47
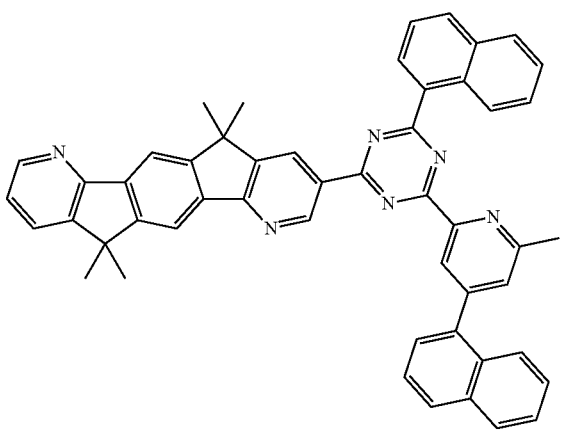
45
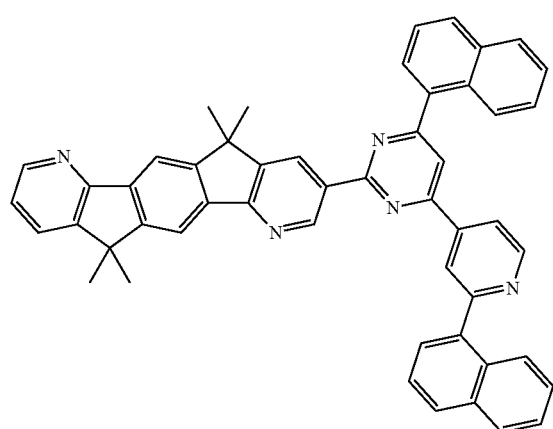
48
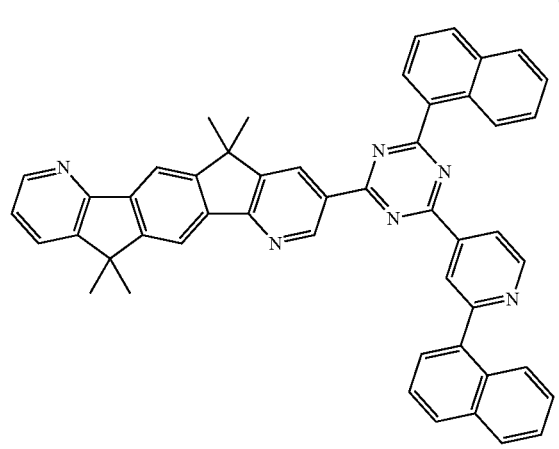

-continued
49
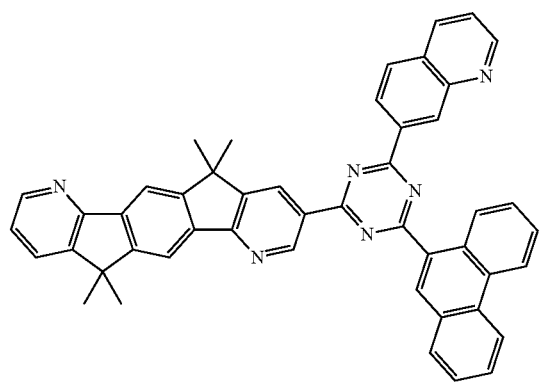
50
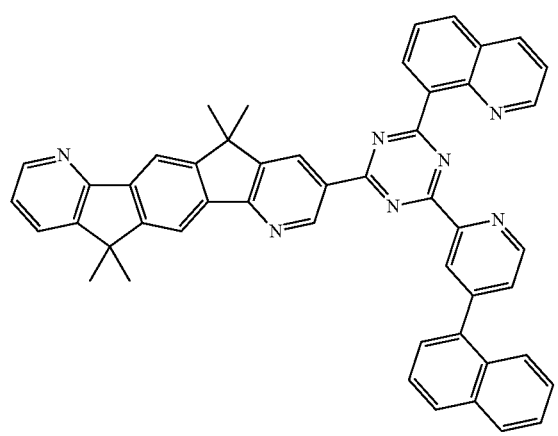
51
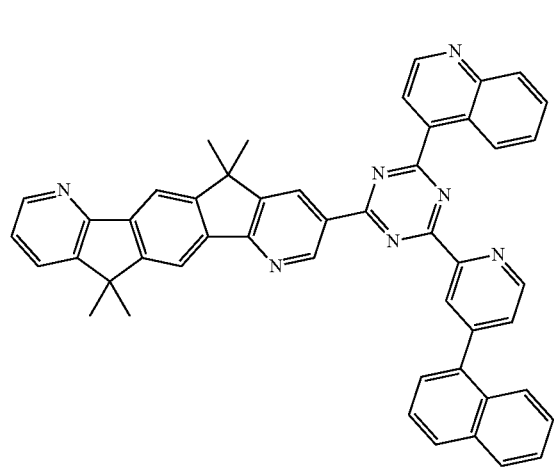
-continued
52
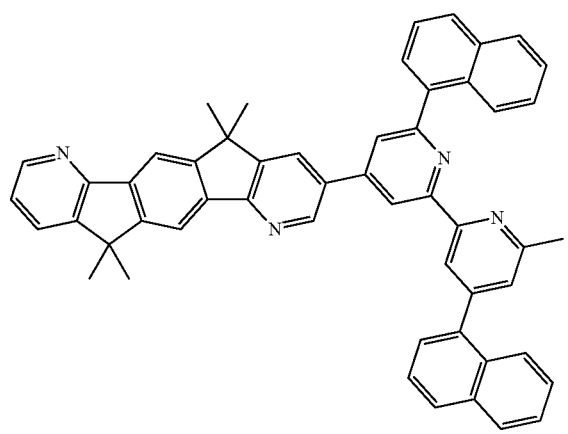
53
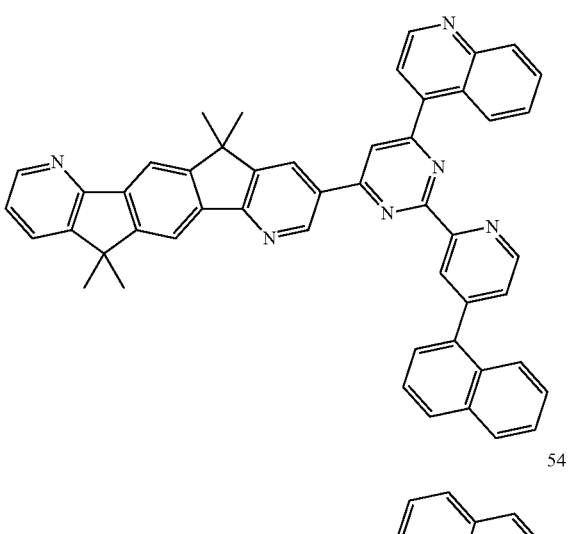
54
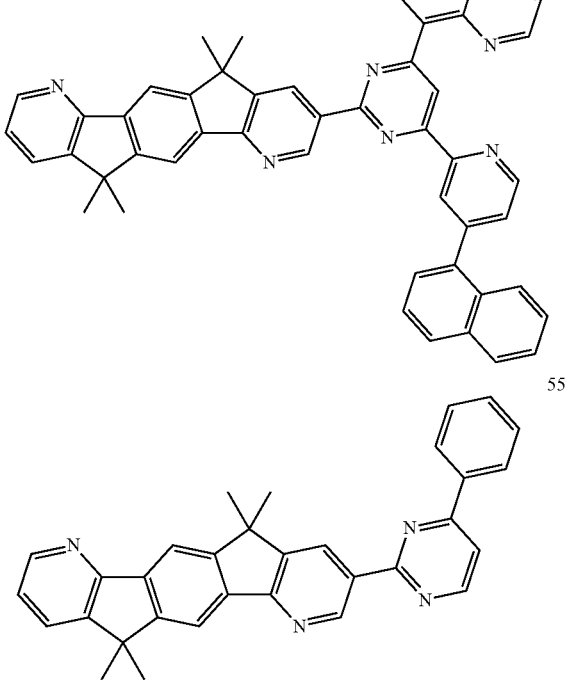
55
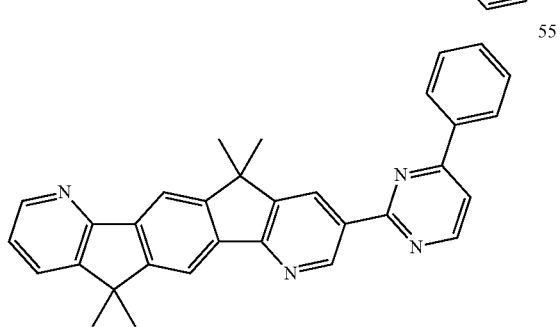

56
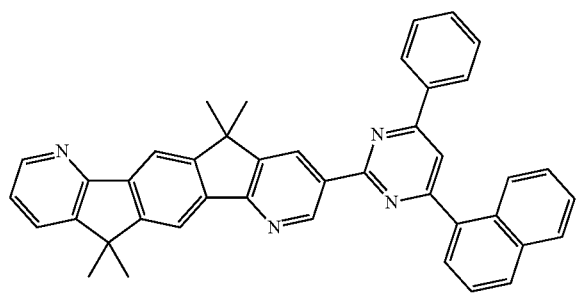
57
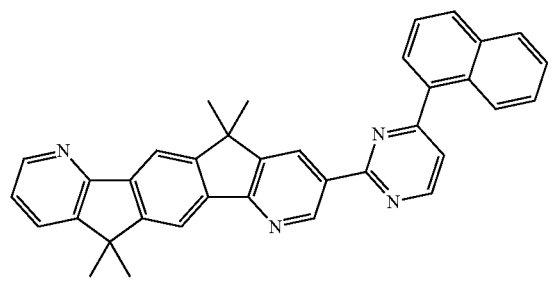
58
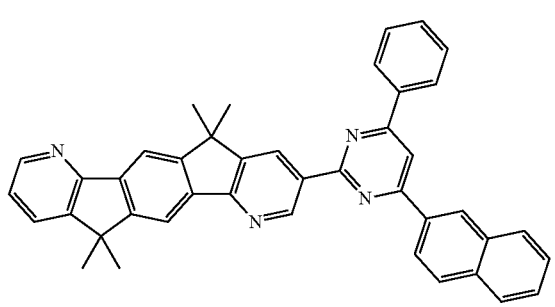
59
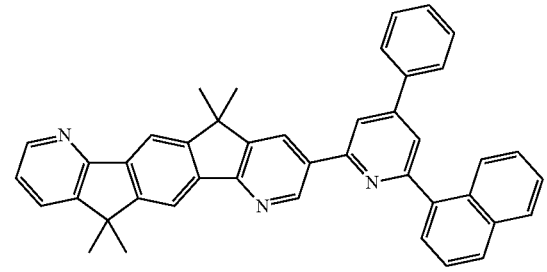
60
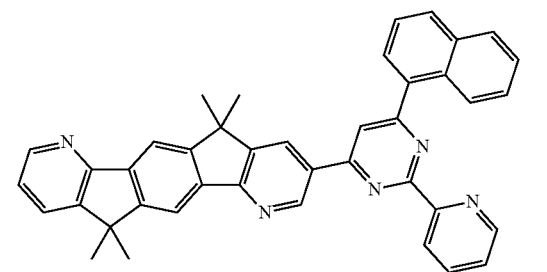
61
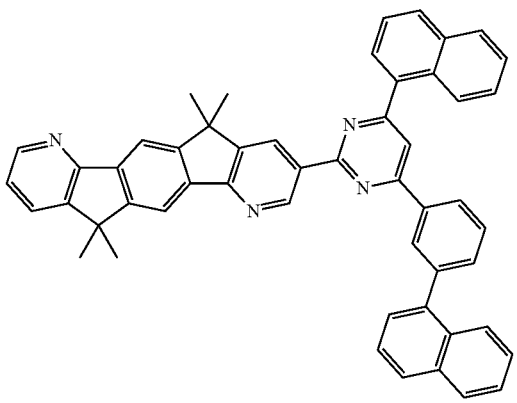
62
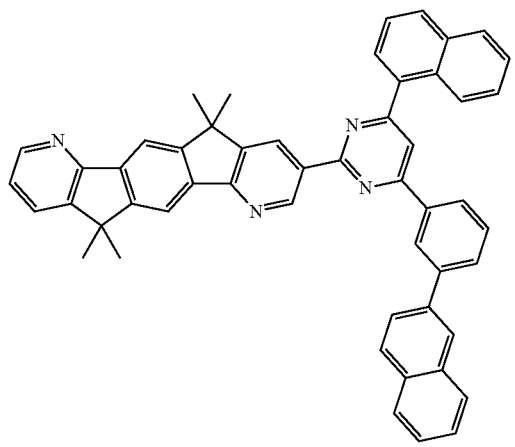
63
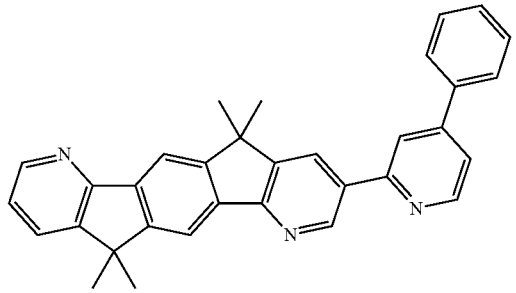
64
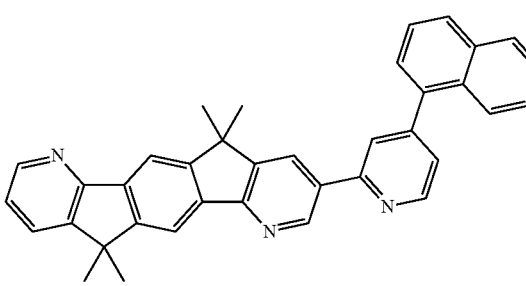

65
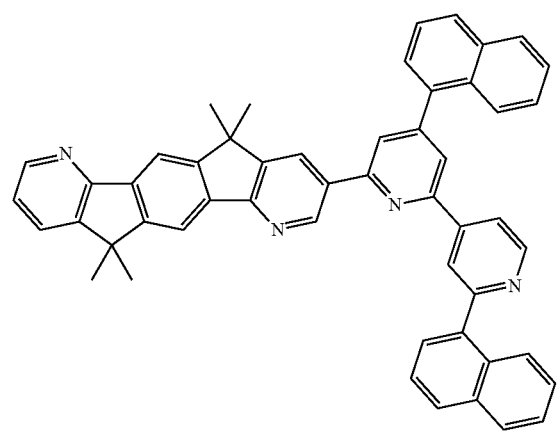
66
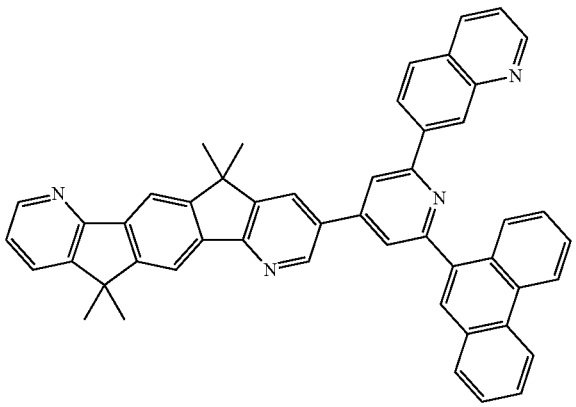
67
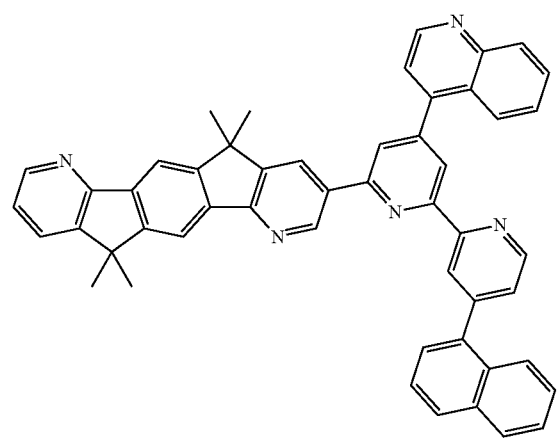
68
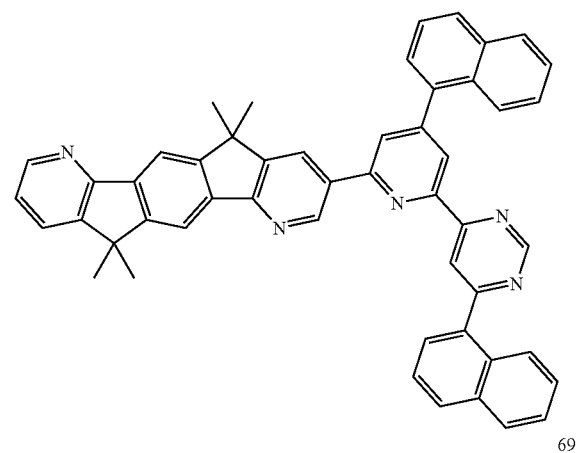
69
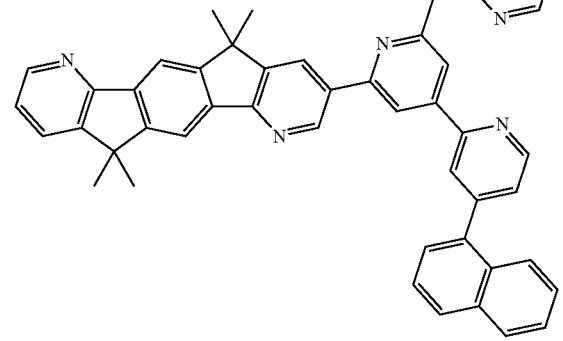
70
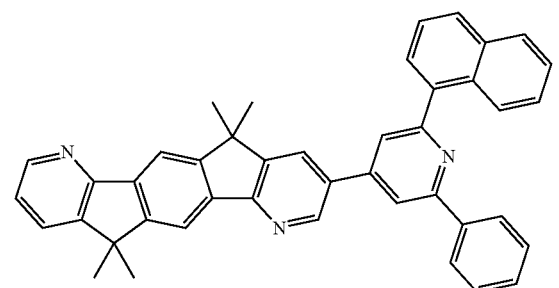
71
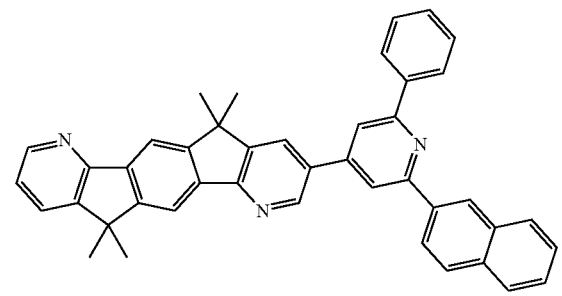

72
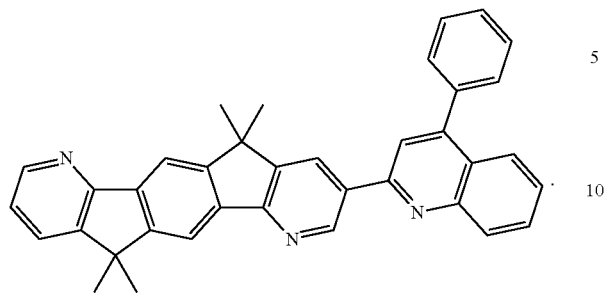
* * * * *